(12) United States Patent
Kardosh et al.

(10) Patent No.: US 9,707,414 B2
(45) Date of Patent: Jul. 18, 2017

(54) REFLECTANCE-FACILITATED ULTRASOUND TREATMENT AND MONITORING

(71) Applicant: RAINBOW MEDICAL LTD., Herzliya (IL)

(72) Inventors: Michael Kardosh, Kiriat Ono (IL); Amir Kishon, Petach Tikva (IL); Navot Rabban, Tel Aviv (IL); Gilad Magnazi, Hod Hasharon (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 111 days.

(21) Appl. No.: 14/832,346

(22) Filed: Aug. 21, 2015

(65) Prior Publication Data

US 2015/0359558 A1    Dec. 17, 2015

Related U.S. Application Data

(63) Continuation-in-part of application No. 14/378,646, filed as application No. PCT/IL2013/050134 on Feb. 13, 2013.

(Continued)

(51) Int. Cl.
 *A61B 17/32* (2006.01)
 *A61N 7/02* (2006.01)
(Continued)

(52) U.S. Cl.
 CPC .......... *A61N 7/022* (2013.01); *A61B 17/1204* (2013.01); *A61B 17/12122* (2013.01);
(Continued)

(58) Field of Classification Search
 CPC ...... A61N 7/02; A61N 1/0587; A61N 1/0563; A61B 2018/00351; A61B 2018/00577;
(Continued)

(56) References Cited

U.S. PATENT DOCUMENTS 4,619,247 A    10/1986    Inoue
5,735,280 A    4/1998    Sherman et al.
(Continued)

FOREIGN PATENT DOCUMENTS

DE    10126062    12/2001
DE    102006058447    6/2008
(Continued)

OTHER PUBLICATIONS

Di Biase L et al., "Prevention of phrenic nerve injury during epicardial ablation: Comparison of methods for separating the phrenic nerve from the epicardial surface," Heart Rhythm 2009;6:957-961.

(Continued)

*Primary Examiner* — Michael Peffley
(74) *Attorney, Agent, or Firm* — Sughrue Mion, PLLC

(57) ABSTRACT

Apparatus comprising a reflection-facilitation element, which is disposed in the pericardial cavity of a subject and on a first side of a tissue of the subject. The reflection-facilitation element comprises an inflatable member, having a first side and a second side, and configured to be inflated while disposed in the pericardial cavity, and a plurality of electrodes, comprising at least a first electrode and a second electrode, the first electrode being disposed on the first side of the inflatable member. The apparatus further comprises an ultrasound transducer placed on a second side of the tissue of the subject, and configured to apply ultrasound energy to the tissue of the subject such that at least a portion of the energy reaches the inflatable member. The inflatable mem- (Continued)

ber reflects at least a portion of the ultrasound energy that reaches the inflatable member.

18 Claims, 28 Drawing Sheets

Related U.S. Application Data

(60) Provisional application No. 62/040,011, filed on Aug. 21, 2014, provisional application No. 61/598,347, filed on Feb. 14, 2012, provisional application No. 61/602,686, filed on Feb. 24, 2012, provisional application No. 61/698,773, filed on Sep. 10, 2012.

(51) Int. Cl.
| | | |
|---|---|---|
| *A61B 17/12* | (2006.01) | |
| *A61N 1/05* | (2006.01) | |
| A61B 17/00 | (2006.01) | |
| A61B 90/00 | (2016.01) | |
| A61B 17/22 | (2006.01) | |
| A61B 18/00 | (2006.01) | |
| A61N 7/00 | (2006.01) | |

(52) U.S. Cl.
CPC ...... *A61B 17/12136* (2013.01); *A61N 1/0597* (2013.01); *A61B 90/37* (2016.02); *A61B 2017/00044* (2013.01); *A61B 2017/22058* (2013.01); *A61B 2018/00285* (2013.01); *A61B 2018/00351* (2013.01); *A61B 2018/00839* (2013.01); *A61B 2090/0472* (2016.02); *A61B 2090/08021* (2016.02); *A61N 2007/0069* (2013.01)

(58) Field of Classification Search
CPC A61B 2018/00375; A61B 2018/00357; A61B 2018/0022; A61B 5/0084; A61B 5/065; A61M 25/04; A61M 25/10
See application file for complete search history.

(56) References Cited

U.S. PATENT DOCUMENTS

| | | | |
|---|---|---|---|
| 5,776,063 A | 7/1998 | Dittrich et al. | |
| 5,817,022 A | 10/1998 | Vesely | |
| 5,827,216 A | 10/1998 | Igo et al. | |
| 5,971,911 A * | 10/1999 | Wilk | A61B 17/00234 |
| | | | 600/18 |
| 6,004,269 A | 12/1999 | Crowley et al. | |
| 6,050,943 A | 4/2000 | Slayton | |
| 6,064,902 A | 5/2000 | Haissaguerre et al. | |
| 6,083,166 A | 7/2000 | Holdaway et al. | |
| 6,128,523 A | 10/2000 | Bechtold | |
| 6,216,704 B1 | 4/2001 | Ingle et al. | |
| 6,231,518 B1 | 5/2001 | Grabek et al. | |
| 6,241,727 B1 | 6/2001 | Tu | |
| 6,425,877 B1 | 7/2002 | Edwards | |
| 6,575,969 B1 | 6/2003 | Rittman et al. | |
| 6,605,084 B2 | 8/2003 | Acker et al. | |
| 6,635,054 B2 | 10/2003 | Fjield et al. | |
| 6,641,579 B1 | 11/2003 | Bernardi et al. | |
| 6,659,950 B2 | 12/2003 | Taheri | |
| 6,685,639 B1 | 2/2004 | Wang | |
| 6,701,931 B2 | 3/2004 | Sliwa et al. | |
| 6,805,129 B1 | 10/2004 | Pless et al. | |
| 7,022,105 B1 | 4/2006 | Edwards | |
| 7,037,306 B2 | 5/2006 | Podany et al. | |
| 7,226,440 B2 | 6/2007 | Gelfand et al. | |
| 7,311,701 B2 | 12/2007 | Gifford et al. | |
| 7,326,201 B2 | 2/2008 | Fjield et al. | |
| 7,565,191 B2 | 7/2009 | Burbank et al. | |
| 7,662,099 B2 | 2/2010 | Podany et al. | |
| 8,142,493 B2 | 3/2012 | Spence et al. | |
| 8,197,409 B2 | 6/2012 | Foley | |
| 9,256,561 B2 * | 2/2016 | Shiraishi | G06F 13/385 |
| 9,526,561 B2 | 12/2016 | Garabedian et al. | |
| 2001/0003798 A1 | 6/2001 | McGovern | |
| 2002/0091427 A1 | 7/2002 | Rappaport | |
| 2003/0018256 A1 | 1/2003 | Sasaki | |
| 2003/0187460 A1 | 10/2003 | Chin et al. | |
| 2004/0034339 A1 | 2/2004 | Stoller | |
| 2004/0097788 A1 | 5/2004 | Mourlas | |
| 2004/0162507 A1 | 8/2004 | Govari et al. | |
| 2004/0162550 A1 | 8/2004 | Govari et al. | |
| 2004/0167563 A1 | 8/2004 | Fogarty et al. | |
| 2005/0020921 A1 | 1/2005 | Glassell | |
| 2005/0080469 A1 | 4/2005 | Larson et al. | |
| 2005/0154279 A1 * | 7/2005 | Li | A61B 5/06 |
| | | | 600/407 |
| 2005/0165298 A1 | 7/2005 | Larson | |
| 2005/0203410 A1 | 9/2005 | Jenkins | |
| 2005/0251125 A1 | 11/2005 | Pless | |
| 2006/0009753 A1 | 1/2006 | Fjield et al. | |
| 2006/0058711 A1 | 3/2006 | Harhen et al. | |
| 2006/0079868 A1 | 4/2006 | Makin et al. | |
| 2006/0100514 A1 | 5/2006 | Lopath | |
| 2006/0155269 A1 | 7/2006 | Warnking | |
| 2006/0184048 A1 | 8/2006 | Saadat | |
| 2006/0241523 A1 | 10/2006 | Sinelnikov et al. | |
| 2006/0253113 A1 * | 11/2006 | Arnold | A61B 18/24 |
| | | | 606/16 |
| 2007/0004984 A1 | 1/2007 | Crum et al. | |
| 2007/0093420 A1 | 4/2007 | Yeomans | |
| 2007/0129719 A1 | 6/2007 | Kendale et al. | |
| 2007/0239077 A1 | 10/2007 | Azhari et al. | |
| 2007/0265610 A1 | 11/2007 | Thapliyal et al. | |
| 2008/0015445 A1 | 1/2008 | Saadat | |
| 2008/0033415 A1 | 2/2008 | Rieker et al. | |
| 2008/0058682 A1 | 3/2008 | Azhari et al. | |
| 2008/0091109 A1 | 4/2008 | Abraham | |
| 2009/0048514 A1 | 2/2009 | Azhari | |
| 2009/0062790 A1 | 3/2009 | Malchano | |
| 2009/0137900 A1 | 5/2009 | Bonner et al. | |
| 2009/0192506 A9 | 7/2009 | Vaska et al. | |
| 2009/0209986 A1 | 8/2009 | Stewart et al. | |
| 2009/0247912 A1 | 10/2009 | Warnking | |
| 2009/0326511 A1 * | 12/2009 | Shivkumar | A61B 90/04 |
| | | | 604/506 |
| 2010/0036292 A1 | 2/2010 | Darlington et al. | |
| 2010/0125281 A1 | 5/2010 | Jacobson et al. | |
| 2010/0130836 A1 | 5/2010 | Malchano | |
| 2010/0168624 A1 | 7/2010 | Sliwa | |
| 2010/0217151 A1 | 8/2010 | Gostout et al. | |
| 2011/0009853 A1 | 1/2011 | Bertolero et al. | |
| 2011/0178541 A1 | 7/2011 | Azhari | |
| 2011/0184322 A1 | 7/2011 | Brawer | |
| 2011/0251524 A1 | 10/2011 | Azhari | |
| 2011/0282203 A1 * | 11/2011 | Tsoref | A61B 8/0841 |
| | | | 600/443 |
| 2011/0282249 A1 * | 11/2011 | Tsoref | A61N 7/022 |
| | | | 601/2 |
| 2012/0116158 A1 | 5/2012 | Hale et al. | |
| 2012/0130363 A1 | 5/2012 | Kim | |
| 2012/0296240 A1 | 11/2012 | Azhari | |
| 2013/0103028 A1 | 4/2013 | Tsoref et al. | |
| 2014/0058294 A1 | 2/2014 | Gross et al. | |
| 2015/0165244 A1 | 6/2015 | Kardosh et al. | |

FOREIGN PATENT DOCUMENTS

| | | |
|---|---|---|
| EP | 1498153 A1 | 1/2005 |
| EP | 1518498 | 3/2005 |
| JP | H11-123197 | 5/1999 |
| JP | 2011-177597 | 9/2011 |
| WO | 97/35518 A1 | 10/1997 |
| WO | 99/23812 | 5/1999 |
| WO | 99/40957 | 8/1999 |
| WO | 99/59663 | 11/1999 |
| WO | 03/097162 | 11/2003 |
| WO | 2006/072928 | 7/2006 |

(56) References Cited

FOREIGN PATENT DOCUMENTS

| WO | 2007/127664 | | 11/2007 |
|---|---|---|---|
| WO | 2007/134258 | | 11/2007 |
| WO | 2010/029556 | A1 | 3/2010 |
| WO | 2010/123895 | A2 | 10/2010 |
| WO | 2011/141918 | | 11/2011 |
| WO | 2012/120495 | | 9/2012 |
| WO | 2013/121424 | | 8/2013 |
| WO | 2014/015259 | | 1/2014 |

OTHER PUBLICATIONS

Matsuo S et al., "Novel technique to prevent left phrenic nerve injury during epicardial catheter ablation," Circulation 2008;117:e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, August Supplement 2009.

Sacher F et al., "Phrenic Nerve Injury After Catheter Ablation of Atrial Fibrillation," Indian Pacing Electrophysiol J. Jan.-Mar. 2007; 7(1): 1-6.

An International Preliminary Report on Patentability dated Nov. 20, 2012, which issued during the prosecution of Applicant's PCT/IL11/00382.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

Tearney GJ et al., "Three-Dimensional coronary artery microscopy by intracoronary optical frequency domain imaging" JACC Cardiovasc Imaging. Nov. 2008; 1(6): 752-761.

William E. Cohn, et al., "Contrast pericardiography facilitates intrapericardial navigation under fluoroscopy", Ann Thorac Surg 2010; 90: 1537-40. Accepted for publication Jun. 7, 2010.

Srijoy Mahapatra, et al., "Pressure frequency characteristics of the pericardial space and thorax during subxiphoid access for epicardial ventricular tachycardia ablation", Heart Rhythm 2010; 7:604-609.

Schuessler RB et al., "Animal studies of epicardial atrial ablation," Heart Rhythm, vol. 6, No. 12S, S41-S45, December Supplement 2009.

An International Search Report and a Written Opinion both dated Oct. 26, 2011, which issued during the prosecution of Applicant's PCT/IL11/00382.

An International Search Report and a Written Opinion both dated Sep. 17, 2012, which issued during the prosecution of Applicant's PCT/IL2012/000100.

An Office Action dated Dec. 20, 2012, which issued during the prosecution of U.S. Appl. No. 11/653,115.

An Office Action dated Feb. 19, 2013, which issued during the prosecution of U.S. Appl. No. 13/010,555.

An International Search Report and a Written Opinion both dated Sep. 18, 2015, which issued during the prosecution of Applicant's PCT/IB2015/055132.

An International Search Report and a Written Opinion both dated Aug. 12, 2013, which issued during the prosecution of Applicant's PCT/IL2013/050134.

An Invitation to pay additional fees dated Jul. 28, 2015, which issued during the prosecution of Applicant's PCT/IB2015/053280.

European Search Opinion dated Oct. 8, 2015, which issued during the prosecution of Applicant's European App No. 13749108.

Buch E et al., "Intra-pericardial balloon retraction of the left atrium: A novel method to prevent esophageal injury during catheter ablation," Heart Rhythm 2008;5:1473-1475.

Cassak D, "Endosense: Facing technology and financing challenges in AF," In-Vivo: The Business & Medicine Report, 36-44, Mar. 2010.

A Written Opinion dated Nov. 9, 2015, which issued during the prosecution of Applicant's PCT/IB2015/053280.

An Office Action dated May 8, 2014, which issued during the prosecution of U.S. Appl. No. 13/015,951.

An Office Action dated May 17, 2013, which issued during the prosecution of U.S. Appl. No. 12/780,240.

An Office Action dated Feb. 5, 2014, which issued during the prosecution of U.S. Appl. No. 13/015,951.

U.S. Appl. No. 61/598,347, filed Feb. 14, 2012.
U.S. Appl. No. 62/040,011, filed Aug. 21, 2014.
U.S. Appl. No. 61/602,686, filed Feb. 24, 2012.
U.S. Appl. No. 61/698,773, filed Sep. 10, 2012.

Extended European Search Report dated Nov. 22, 2016 issued in EP 11780309.

An Office Action dated Feb. 6, 2017 issued in U.S. Appl. No. 14/378,646.

English translation of Chinese office action dated Oct. 25, 2016 issued in CN 201380019982.2.

English translation of Chinese office action dated Mar. 29, 2017 issued in CN 201380019982.2.

* cited by examiner

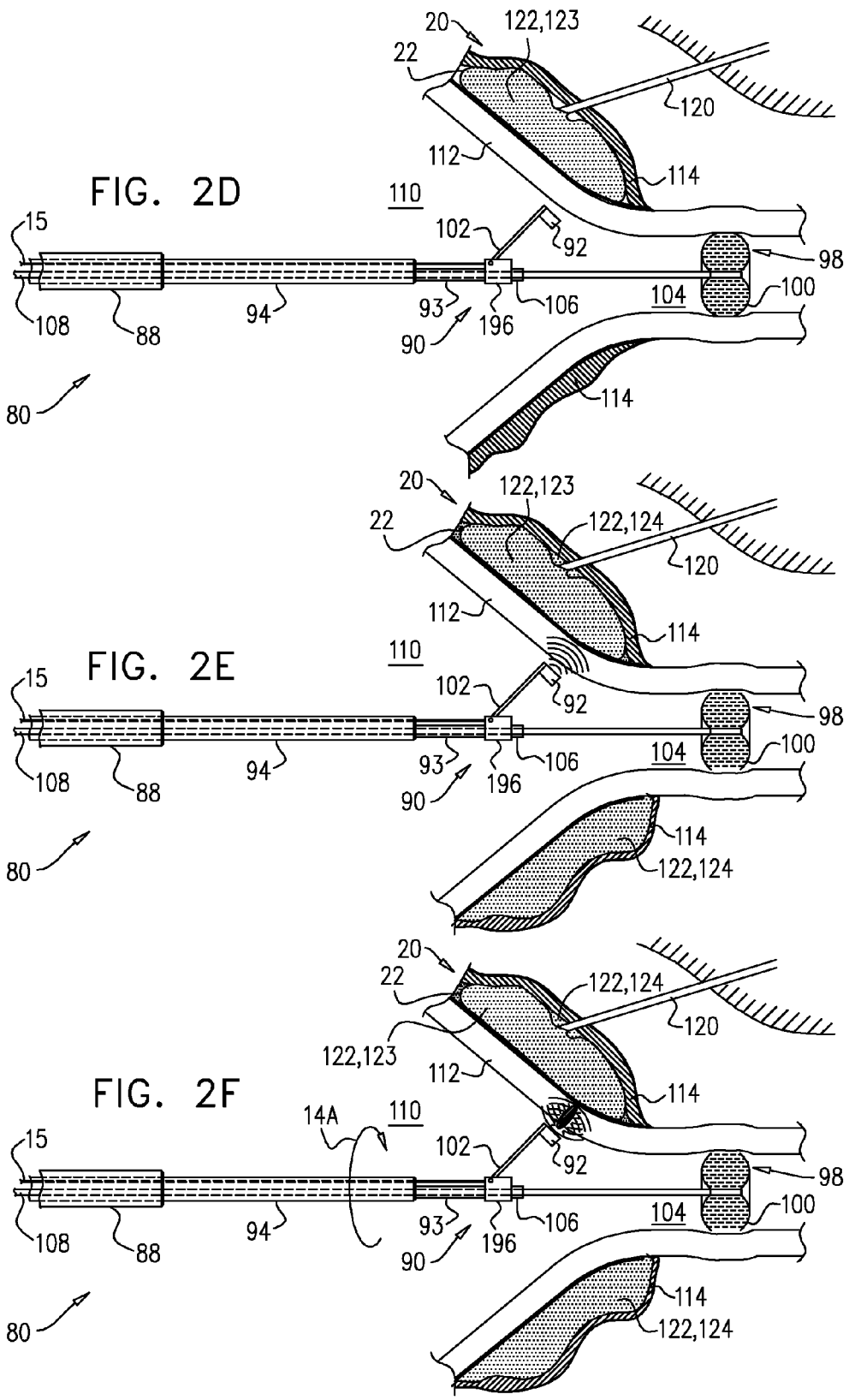

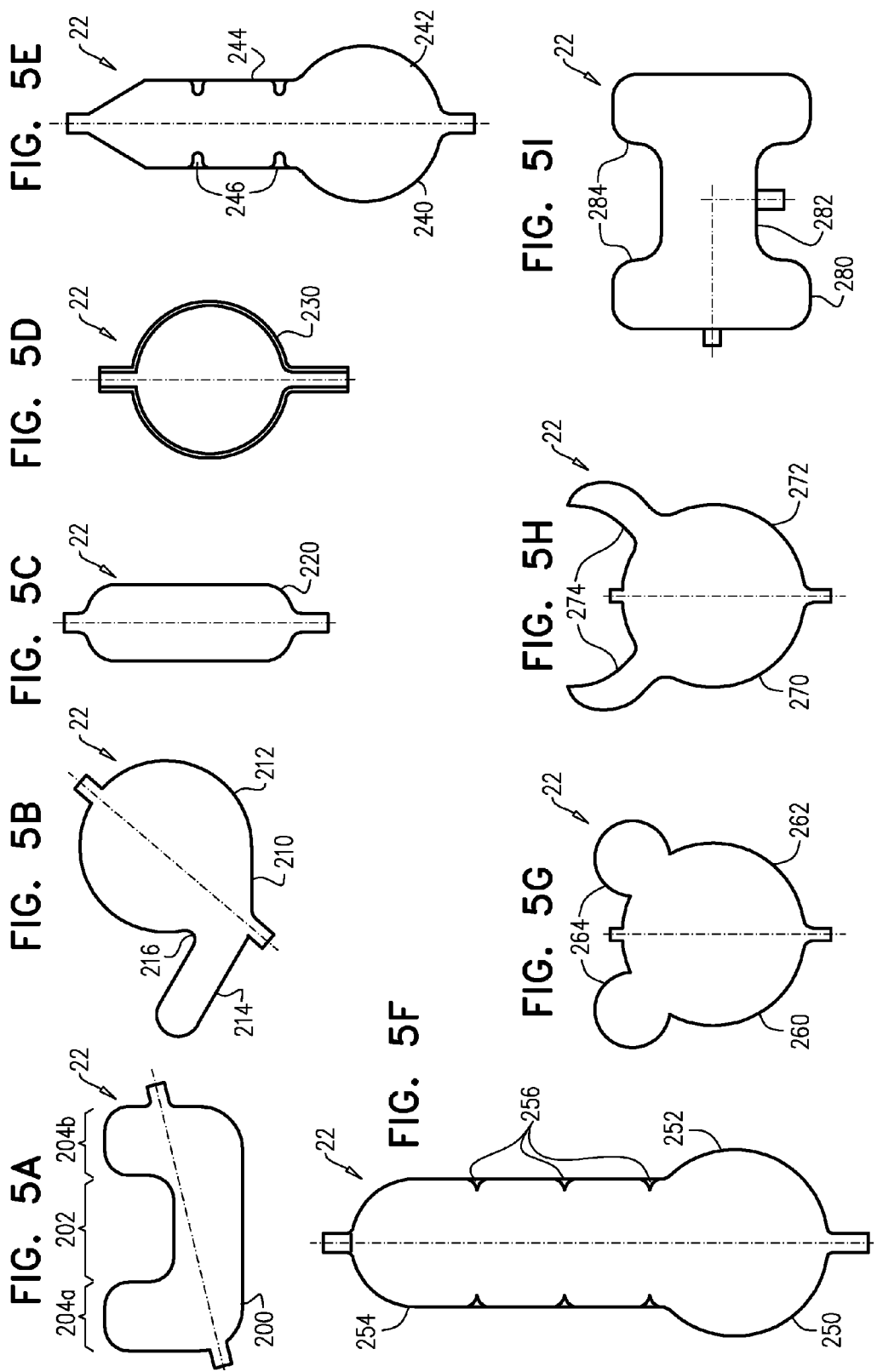

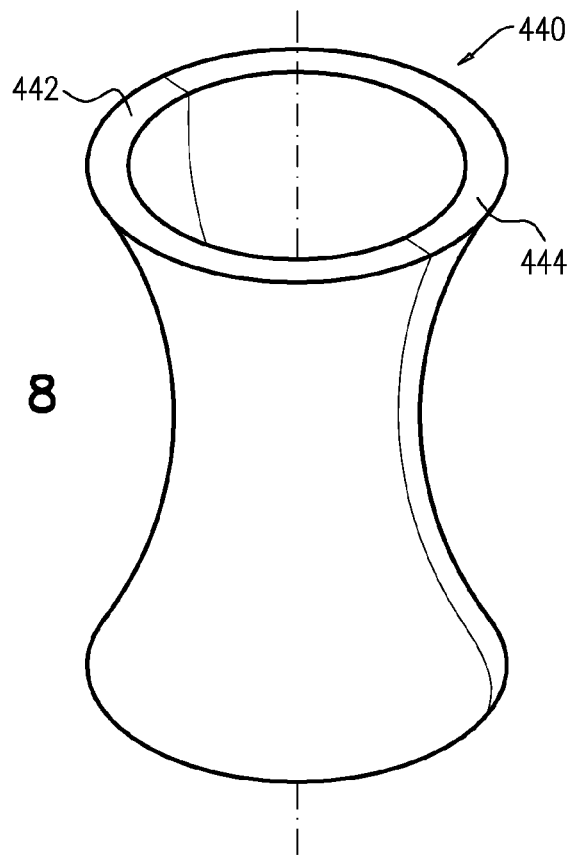
FIG. 8
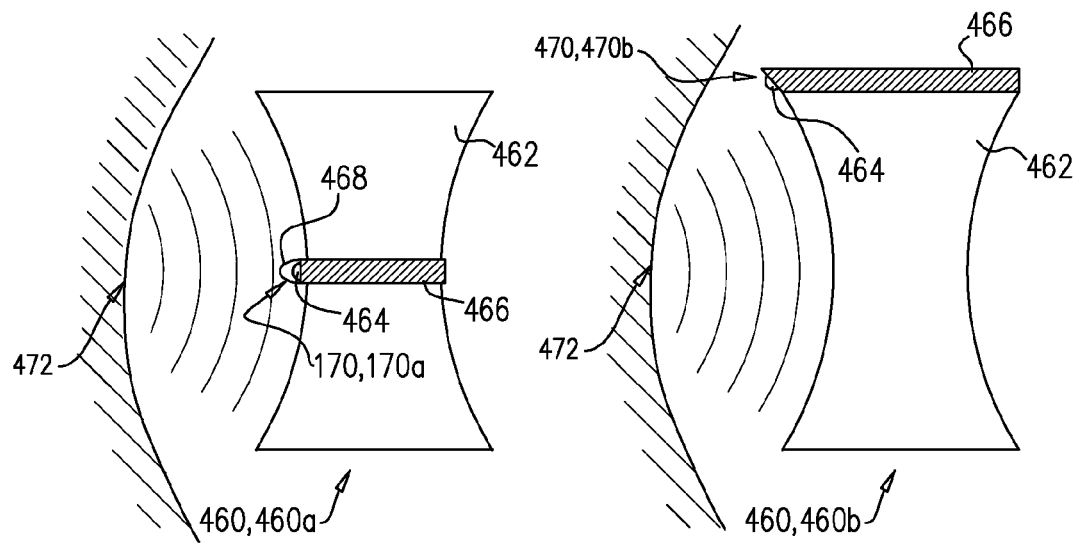
FIG. 9A
FIG. 9B

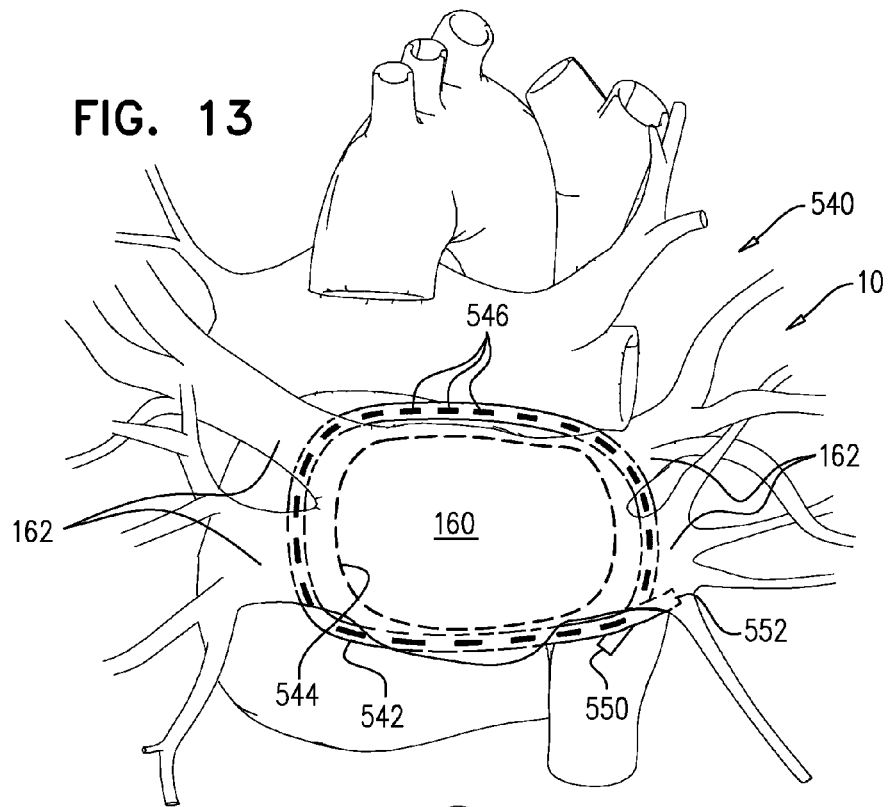
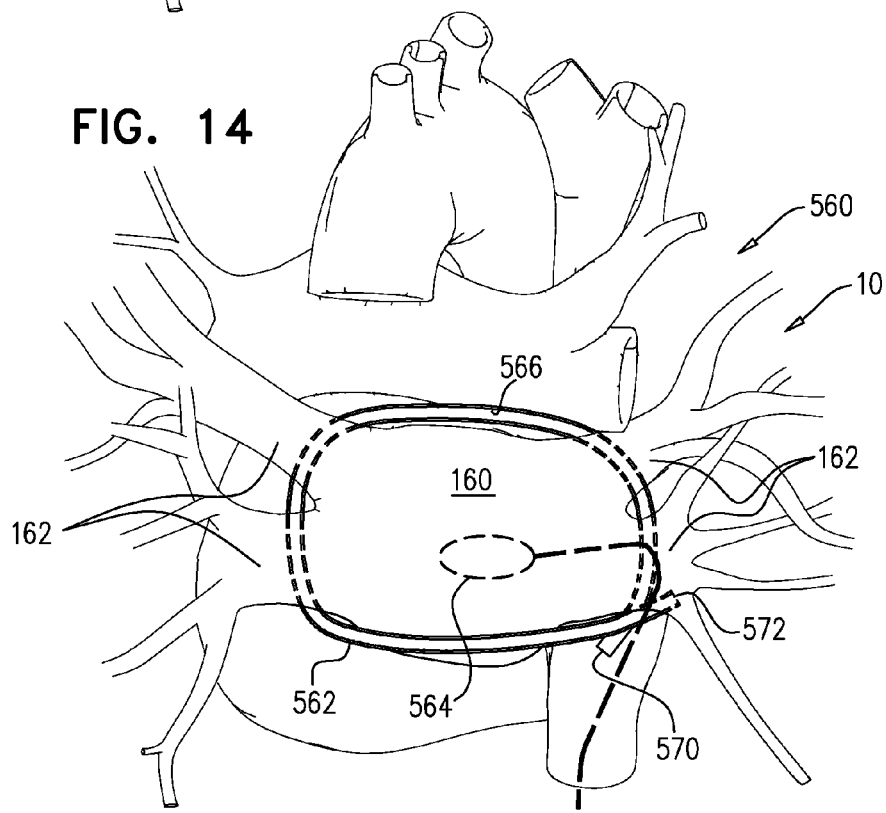

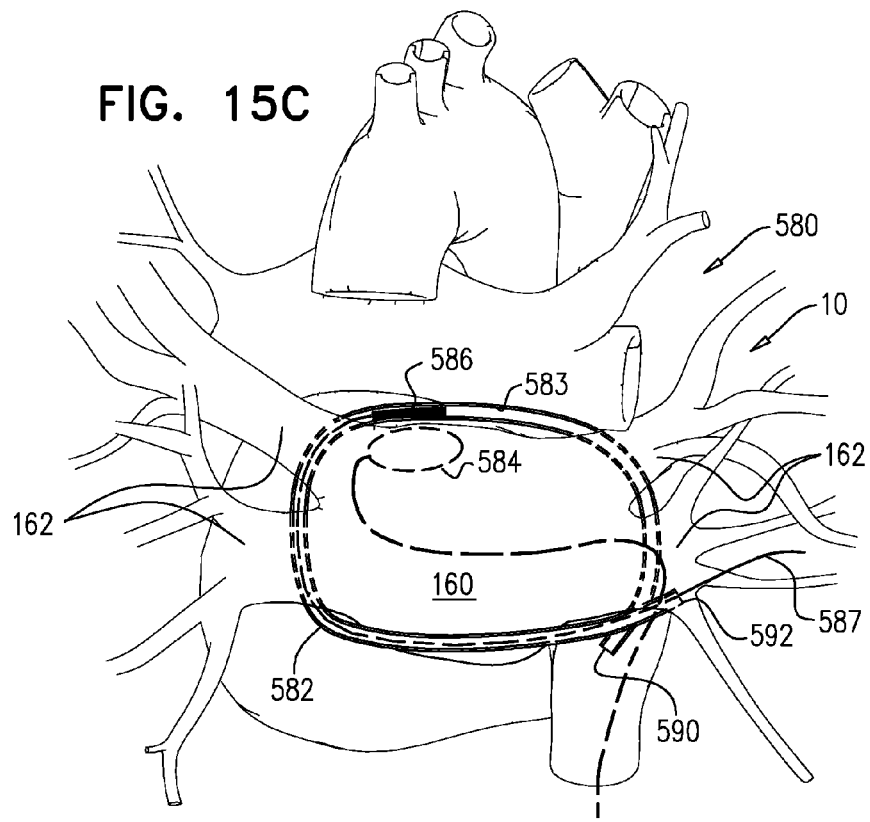
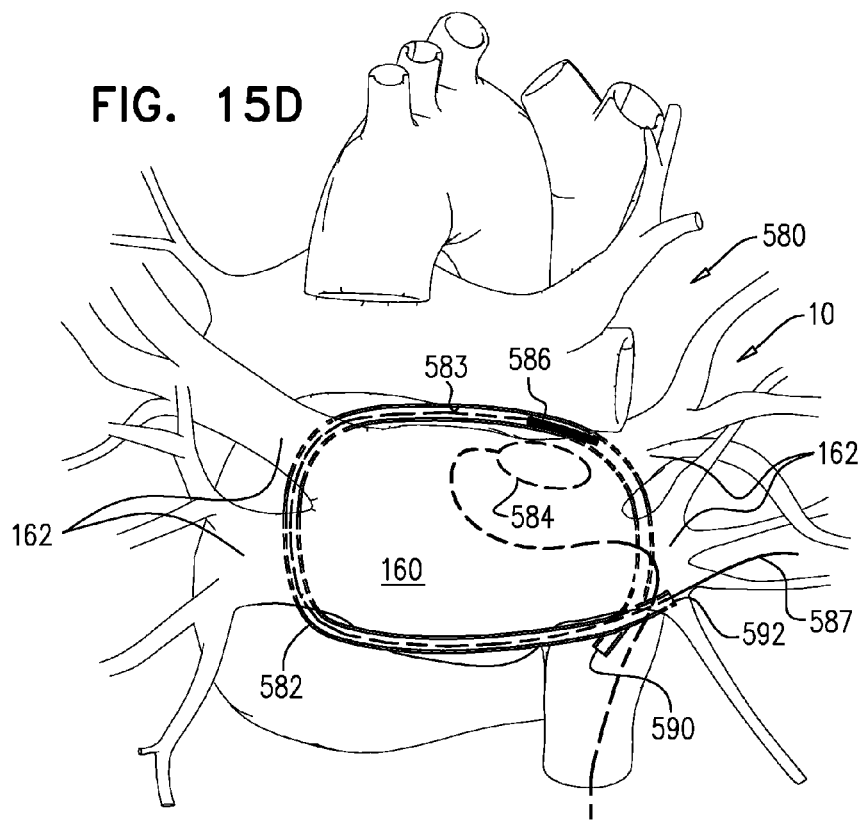

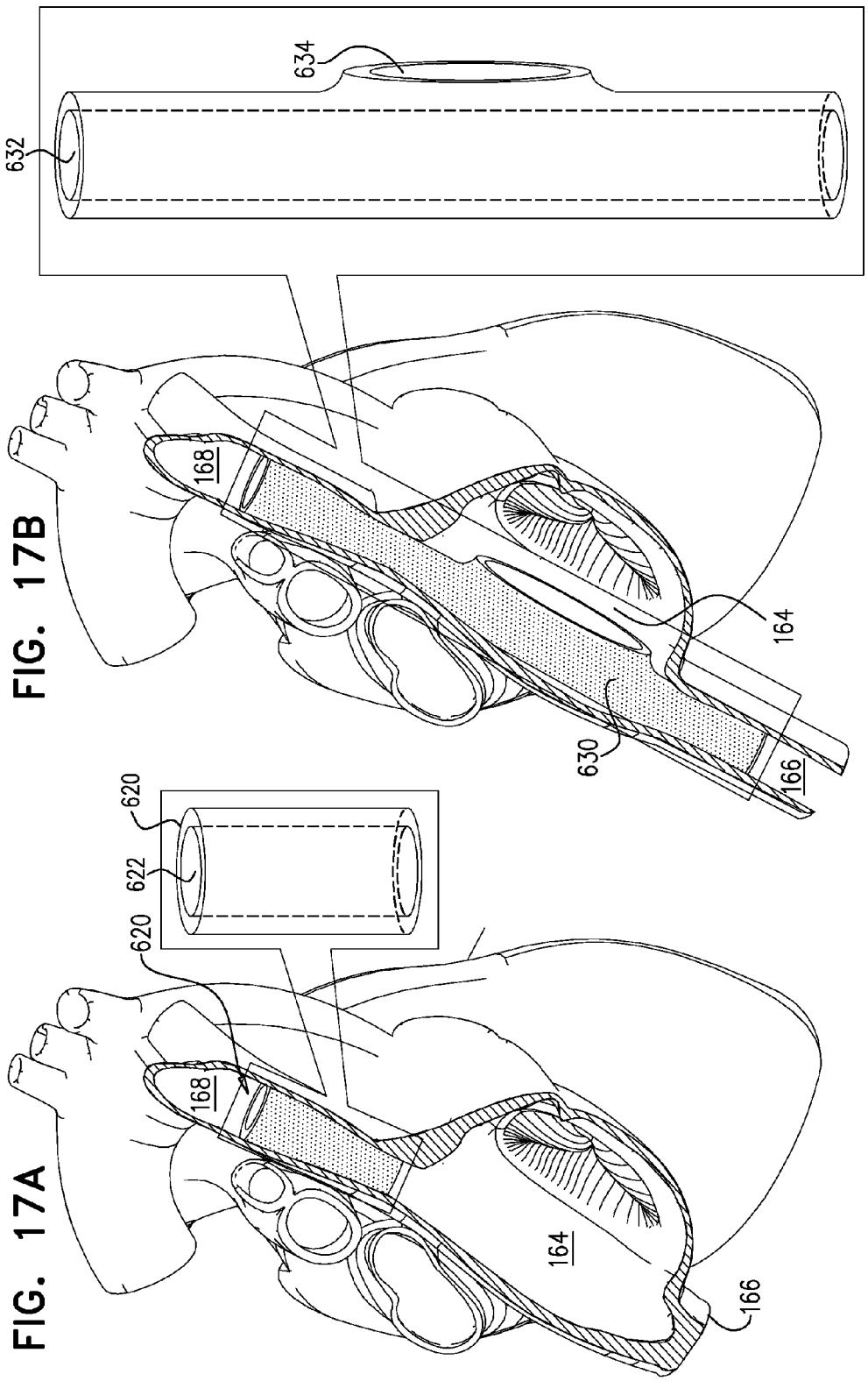

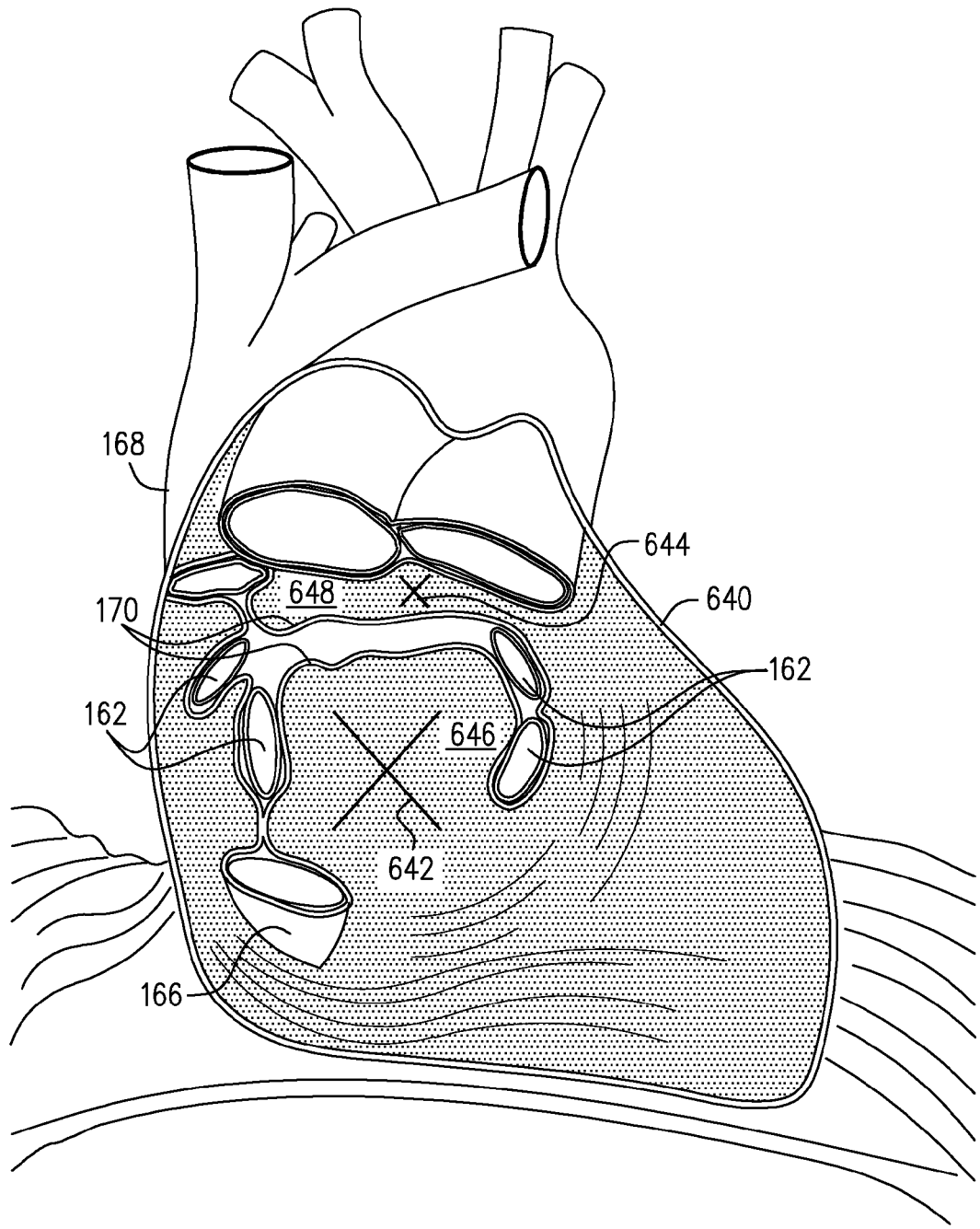

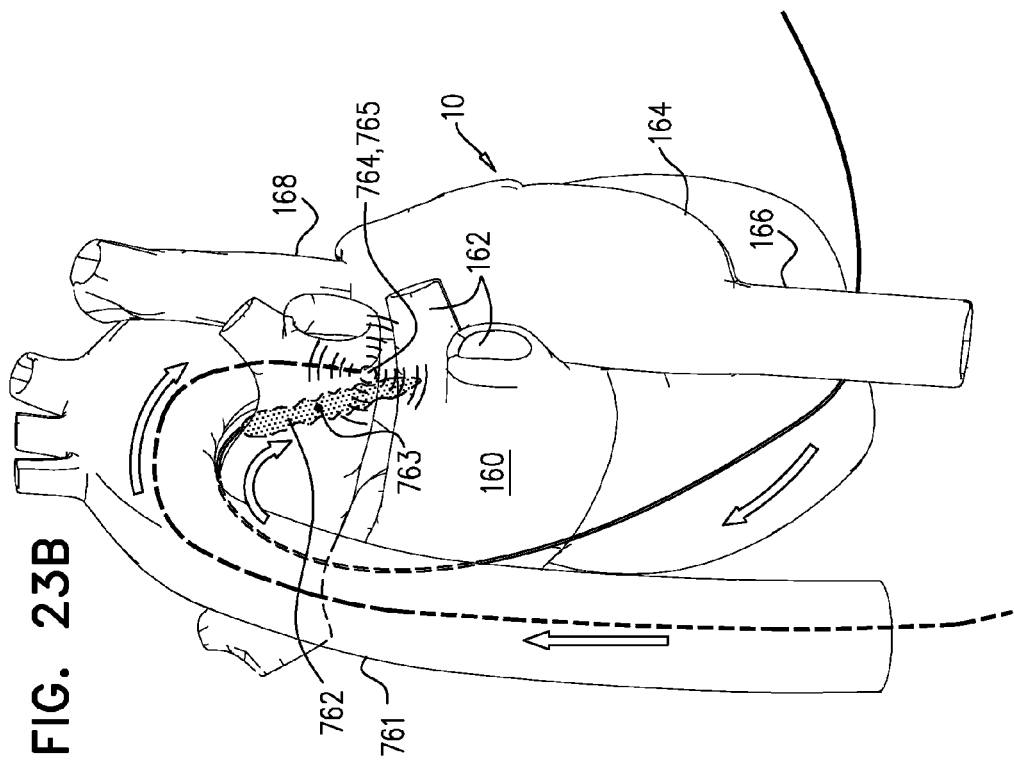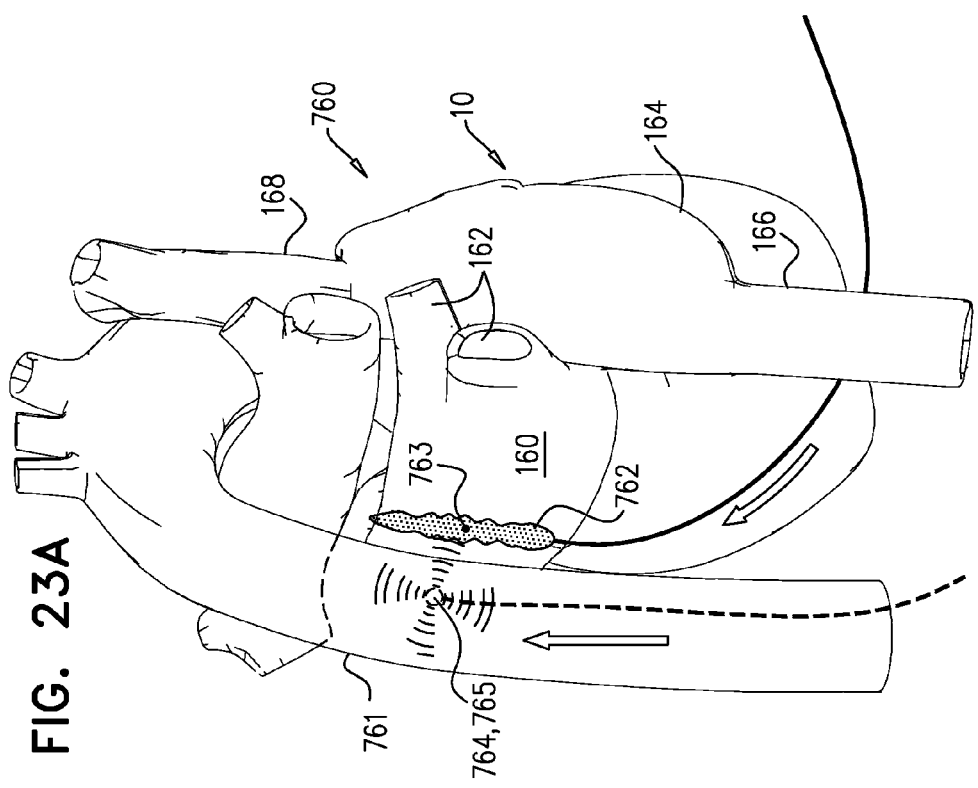

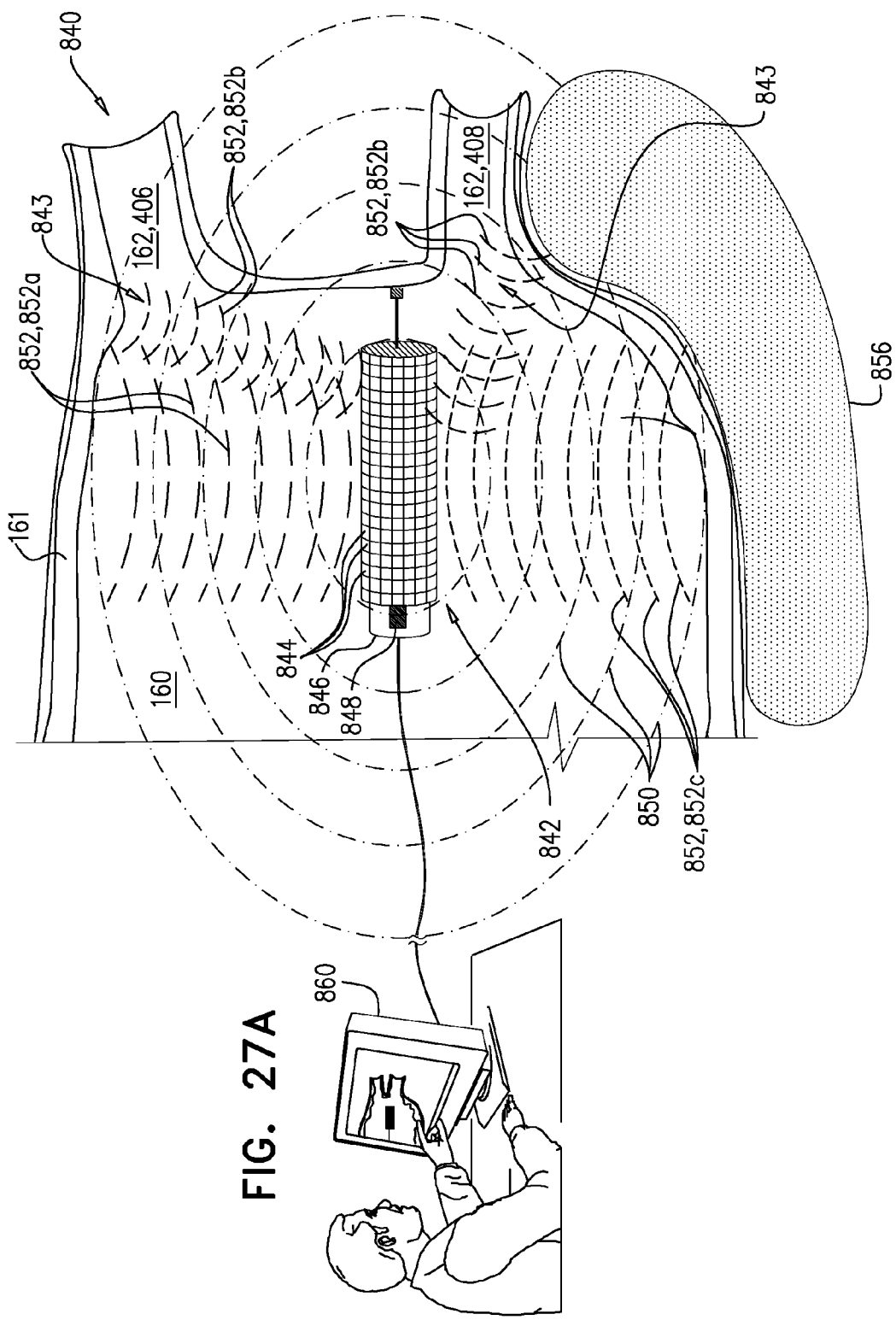

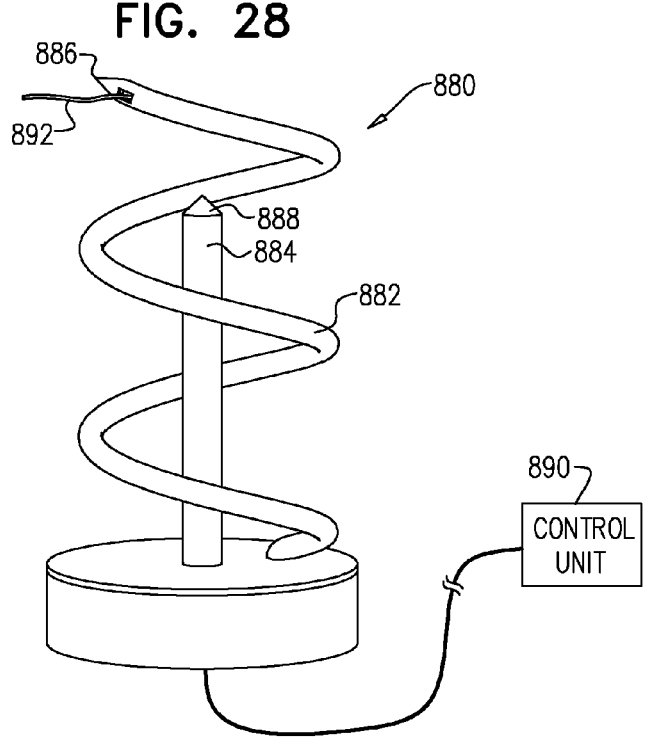
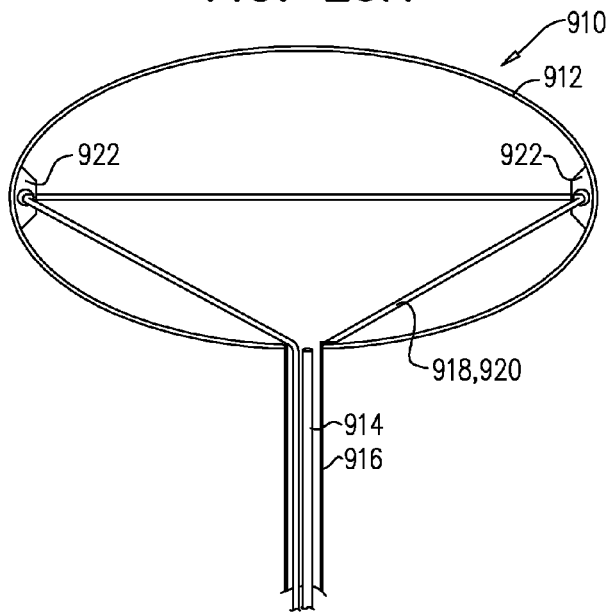
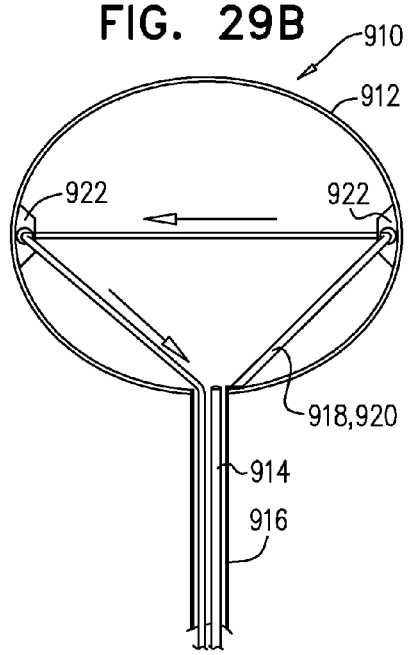

REFLECTANCE-FACILITATED ULTRASOUND TREATMENT AND MONITORING

CROSS-REFERENCES TO RELATED APPLICATIONS

The present application:

(a) claims the priority of U.S. Provisional Application No. 62/040,011, entitled "Reflectance-facilitated ultrasound treatment and monitoring," filed Aug. 21, 2014, (b) is a continuation-in-part of U.S. Ser. No. 14/378,646 (which published as US 2015-0165244) filed on Aug. 13 2014, which is the US national phase of PCT Patent Application IL2013/050134 to Kardosh et al., entitled "Reflectance-facilitated ultrasound treatment and monitoring," filed Feb. 13, 2013, which published as WO 2013/121424, and which claims priority from (i) U.S. Provisional Application 61/598,347 to Kardosh et al., entitled "Pericardium inflation device," filed Feb. 14, 2012, (ii) U.S. Provisional Application 61/602,686 to Kardosh et al., entitled "Reflectance-facilitated ultrasound treatment and monitoring," filed Feb. 24, 2012, and (iii) U.S. Provisional Application 61/698,773 to Kardosh et al., entitled "Reflectance-facilitated ultrasound treatment and monitoring," filed Sep. 10, 2012, all of which are incorporated herein by reference, (c) is related to U.S. patent application Ser. No. 12/780,240 to Tsoref et al., filed on May 14, 2010 and published on Nov. 17, 2011 as US 2011-0282249 and issued on Dec. 31, 2013 as U.S. Pat. No. 8,617,150 to Tsoref et al., (d) is related to U.S. patent application Ser. No. 13/015,951 to Tsoref et al., filed on Jan. 28, 2011 and published as US 2011-0282203 and issued on Feb. 17, 2015 as U.S. Pat. No. 8,956,346 to Tsoref et al., and (e) is related to PCT application IL2011/000382 to Tsoref et al., filed on May 12, 2011 and published as WO 2011-141918.

Each of the above applications is incorporated herein by reference.

FIELD OF THE INVENTION

Embodiments of the present invention relate generally to treatment of tissue by application of energy thereto, and particularly to ablation of cardiac or other tissue by application of ultrasound energy.

BACKGROUND

Atrial fibrillation is a common cardiac arrhythmia involving the atria of the heart. During atrial fibrillation, the atria beat irregularly and out of coordination with the ventricles of the heart. Atrial fibrillation disrupts efficient beating of the heart and may result in blood clotting in the atrium leading to serious medical conditions such as strokes.

Atrial fibrillation is generally caused by abnormal electrical activity in the heart. During atrial fibrillation, electrical discharges may be generated by parts of the atria which do not normally generate electrical discharges, such as pulmonary vein ostia in the atrium. Pulmonary vein isolation is a common medical procedure for treatment of atrial fibrillation.

Ablation technologies currently include unipolar and bipolar techniques. The unipolar techniques employ various energy sources, including radiofrequency (RF), microwave, high intensity focused ultrasound (HIFU), laser, and cryogenic energy sources. The bipolar techniques employ RF energy.

SUMMARY OF THE INVENTION

For some applications, an ultrasound transducer is placed on a first side of the target tissue and applies the ultrasound energy to the target tissue. Typically, at least part of the ultrasound energy passes entirely through the target tissue. A reflective region is provided on a second side of the target tissue from the transducer, by a reflection-facilitation element. The reflective region reflects at least part of ultrasound energy that passes through the target tissue, and thereby protects proximate tissues on the second side of the target tissue by inhibiting the energy from continuing into those tissues.

The target tissue absorbs at least part of the energy that arrives directly from the transducer, and at least part of the energy that is reflected by the reflective region. Thereby, as well as protecting proximate tissues on the second side of the target tissue, the presence of the reflective region increases the amount of energy available to be absorbed by the target tissue, resulting in temperature elevation and enhanced ablation of the target tissue. Reflection of the ultrasound energy such that it passes through the tissue for a second time achieves what may be considered a bipolar effect.

Thereby, providing a reflective region (e.g., by using a reflection-facilitation element) on the other side of the target tissue to an ultrasound transducer, typically increases the efficacy and/or safety of ultrasound-based ablation. For some applications of the invention, the target tissue includes cardiac tissue, the transducer is disposed in a chamber of the heart, and the reflective region is provided in the pericardial cavity (or vice versa).

For some applications of the invention, the reflection-facilitation element comprises an inflatable reflection-facilitation element, configured to provide the reflective region by being inflated with a fluid (typically a gas) that has an acoustic impedance that is different from that of the target tissue, and thereby reflects ultrasound that arrives at the gas via the target tissue. For some applications, the reflection-facilitation element comprises an introducer, configured to provide the reflective region by delivering free gas to the second side of the target tissue (e.g., to the pericardial cavity). For some applications, more than one reflective region is provided, and/or more than one reflection-facilitation element is used. For example, two inflatable reflection-facilitation elements may be used (e.g., one in the pericardial cavity, and one in a heart chamber), or free gas may be used in addition to an inflatable reflection-facilitation element.

For some applications, an inflatable reflection-facilitation element is configured to facilitate delivery and/or control of the free gas. For example, the inflatable reflection-facilitation element may be disposed in the pericardial cavity, in and/or around a portion of the heart, and configured to trap the free gas, and/or to inhibit displacement of the free gas. For some applications, an inflatable reflection-facilitation element comprises an outlet, configured to facilitate delivery of free gas, such as to a site distal to the inflatable reflection-facilitation element.

For some applications, one or more restricting elements (e.g., adjustable restricting elements) are provided to limit and/or control expansion of an inflatable reflection-facilitation element, or a portion thereof, in one or more respective given dimensions.

For some applications, a transducer is provided that is configured to apply ultrasound energy in a non-circular 360-degree focal pattern. For some such applications, the transducer is configured, and used, to generate an annular lesion while the transducer is disposed at a site that is not at the center of the lesion. For example, an annular lesion that circumscribes two pulmonary vein ostia, may be made in a left atrial wall while the transducer is disposed in the vicinity of one of the pulmonary vein ostia.

For some applications, magnetic coupling between the ultrasound transducer and a reflection-facilitation element is used to facilitate ablation, e.g., to facilitate positioning of the reflection-facilitation element with respect to the ultrasound transducer. For some applications, magnetic coupling is used between the reflection-facilitation element and a guiding member, e.g., to facilitate positioning of the reflection-facilitation element.

For some applications, a ultrasound transducer unit is configured (1) to detect anatomy and/or a reflection-facilitation element, and (2) to subsequently ablate tissue at least in part responsively to the detected anatomy and/or reflection-facilitation element.

For some applications, an ultrasound transducer unit comprises first and second ultrasound transducers, each configured to apply ultrasound energy radially in 180 degrees, and fixedly coupled to each other such that the transducer unit is configured to apply ultrasound energy radially in 360 degrees.

For some applications, an inflatable element is provided, that is configured to conduct ultrasound energy from the ultrasound transducer to the target tissue.

For some applications, a camera is used to facilitate ablation of the target tissue, by facilitating navigation, and/or by detecting changes in the tissue indicative of a degree of ablation.

For some applications, an inflatable, tissue-separating element is provided, to facilitate blunt dissection.

For some applications, a pericardial access tool is provided, comprising a helical needle, and a sensor, configured to sense the location of the tool with respect to tissue being penetrated.

For some applications, techniques described herein are practiced in combination with techniques described in one or more of the references cited in the Cross-references section of the present patent application.

There is therefore provided in accordance with some applications of the present invention, apparatus for use in a pericardial cavity proximate to a heart of a subject, the apparatus including:

a reflection-facilitation element, configured to be disposed in the pericardial cavity and on a first side of a tissue of the subject, and including:

an inflatable member, having a first side and a second side, and configured to be inflated while disposed in the pericardial cavity; and a plurality of electrodes, including at least a first electrode and a second electrode, the first electrode being disposed on the first side of the inflatable member; and an ultrasound transducer, configured to be placed on a second side of the tissue of the subject, and to apply ultrasound energy to the tissue of the subject such that at least a portion of the energy reaches the inflatable member, the inflatable member being configured to reflect at least a portion of the ultrasound energy that reaches the inflatable member.

For some applications, the second electrode is disposed on the second side of the inflatable member, and is electrically coupled to the first electrode via a wire configured to conduct electricity from the first side to the second side of the inflatable member.

For some applications, the plurality of electrodes are configured to facilitate navigation of the inflatable member towards the heart of the subject.

For some applications, the plurality of electrodes are disposed in two dimensions on a plane defined by a surface of the reflection-facilitating element.

For some applications, the apparatus includes a control unit, electrically coupled to the plurality of electrodes.

For some applications, each one of the plurality of electrodes is independently electrically coupled to the control unit.

For some applications, the control unit is configured to drive the plurality of electrodes to apply a defibrillating current to the heart of the subject.

For some applications, the plurality of electrodes includes at least 16 electrodes.

For some applications, the control unit includes a monitor, configured to detect, via the electrodes, an electrical signal of the heart of the subject.

For some applications, the control unit includes an extracorporeal display, configured to provide information relating to a position of the inflatable member with respect to anatomy of the subject, based on the detected electrical signal of the heart.

For some applications, the display is configured to display a graphical representation of the position of the inflatable member with respect to anatomy of the subject.

For some applications, the display is configured to display a graphical representation of anatomy of the subject.

For some applications, the control unit is configured to identify a target for ablation in the tissue of the subject, by detecting an electrical abnormality in the electrical signal of the heart of the subject.

There is further provided in accordance with some applications of the present invention, apparatus for use in a pericardial cavity proximate to a heart of a subject, the apparatus including an inflatable member, the inflatable member (a) being flattened and round when inflated and not externally constrained, (b) having a thickness that is less than 20% of a width of the inflatable member, when inflated and not externally constrained, (c) having a first side and a second side, and (d) configured to be inflated while the inflatable member is disposed in the pericardial cavity of the subject.

For some applications, the thickness of the inflatable member is less than 20 mm.

For some applications, the width of the inflatable member is between 20 and 100 mm.

For some applications, the apparatus includes a plurality of electrodes, including at least a first electrode and a second electrode, the first electrode being disposed on the first side of the inflatable member.

For some applications, the second electrode is disposed on the second side of the inflatable member, and is electrically coupled to the first electrode via a wire configured to conduct electricity from the first side to the second side of the inflatable member.

There is further provided in accordance with some applications of the present invention a method for use with a subject, the method including:

delivering a reflection-facilitation element to a pericardial cavity of the subject, the reflection-facilitation element having (a) an inflatable member, having a first side and a second side, and (b) a plurality of electrodes, having at least a first electrode and a second electrode, the first electrode being disposed on the first side of the inflatable member;

while the inflatable member is disposed in the pericardial cavity of the subject, inflating the inflatable member by delivering a fluid to the inflatable member;

placing an ultrasound transducer in a chamber of a heart of the subject;

ablating cardiac tissue by activating the ultrasound transducer to apply ultrasound energy, such that at least part of the ultrasound energy is reflected by the inflatable member; and providing an extracorporeal monitor electrically coupled to the plurality of electrodes, and facilitating detecting, via the electrodes, of an electrical signal of the heart of the subject.

For some applications, detecting includes detecting timing of the electrical signal.

For some applications, detecting includes detecting a magnitude of the electrical signal.

For some applications, the method includes monitoring the progression of the ablation of the cardiac tissue by the detecting of the electrical signal of the heart of the subject.

For some applications, monitoring the progression of the ablation of the cardiac tissue includes monitoring the progression of the ablation of the cardiac tissue by detecting a reduction of an electrical abnormality in the electrical signal.

For some applications, the method includes identifying the cardiac tissue for ablation by the detecting of an electrical abnormality in the electrical signal of the heart of the subject.

For some applications, the extracorporeal monitor includes an extracorporeal display, and the method further includes displaying on the extracorporeal display a graphical representation of a position of the inflatable member with respect to anatomy of the subject, based on detecting the electrical signal of the heart.

For some applications, the extracorporeal monitor includes an extracorporeal display, and the method further includes displaying on the extracorporeal display a graphical representation of an anatomy of the subject, based on detecting the electrical signal of the heart.

There is further provided in accordance with some applications of the present invention a method for use with a subject, the method including:

delivering a reflection-facilitation element to a pericardial cavity of the subject, the reflection-facilitation element having an inflatable member;

while the inflatable member is disposed in the pericardial cavity of the subject, inflating the inflatable member by delivering a gas to the inflatable member;

placing an ultrasound transducer in a chamber of a heart of the subject;

ablating cardiac tissue by activating the ultrasound transducer to apply ultrasound energy, such that at least part of the ultrasound energy is reflected by the inflatable member; and protecting nearby tissue by reducing heating of the nearby tissue by cooling the gas.

For some applications, reducing heating of the nearby tissue includes reducing heating of a coronary artery.

For some applications, delivering the gas to the inflatable member includes delivering the gas under high pressure, and cooling the gas includes inflating the inflatable member by expanding the gas.

The present invention will be more fully understood from the following detailed description of applications thereof, taken together with the drawings, in which:

BRIEF DESCRIPTION OF THE DRAWINGS

FIGS. 2A-F are schematic illustrations of a system for application of ultrasound energy to tissue within a body of a subject, in accordance with some applications of the invention;

FIGS. 5A-I are schematic illustrations of the inflatable element in accordance with respective applications of the invention;

FIG. 8 is a schematic illustration of a transducer unit, in accordance with some applications of the invention;

FIGS. 9A-B are schematic illustrations of a transducer unit, in accordance with some applications of the invention;

FIG. 13 is a schematic illustration of a system for ablating a circumferential lesion in cardiac tissue, in accordance with some applications of the invention;

FIG. 14 is a schematic illustration of a system for ablating a circumferential lesion in cardiac tissue, in accordance with some applications of the invention;

FIGS. 15A-D are schematic illustrations of a system for ablating a circumferential lesion in cardiac tissue, in accordance with some applications of the invention;

FIGS. 17A-B are schematic illustrations of respective intravascular inflatable reflection-facilitation elements, in accordance with some applications of the invention;

FIG. 18 is a schematic illustration of an anterior view of pericardium that surrounds the heart of the subject, showing placement sites for inflatable reflection-facilitation elements, in accordance with some applications of the invention;

FIGS. 23A-B are schematic illustrations of systems and techniques for magnetically facilitating delivery of a reflection-facilitation element, in accordance with some applications of the invention;

FIGS. 27A-B are schematic illustrations of a system for facilitating ablation of heart tissue, in accordance with some applications of the invention;

FIG. 28 is a schematic illustration of a pericardial access tool, comprising a helical needle and a sensor, in accordance with some applications of the invention;

FIGS. 29A-B are schematic illustrations of an inflatable reflection-facilitation element, in accordance with some applications of the invention.

DETAILED DESCRIPTION OF EMBODIMENTS

Figure 1A:
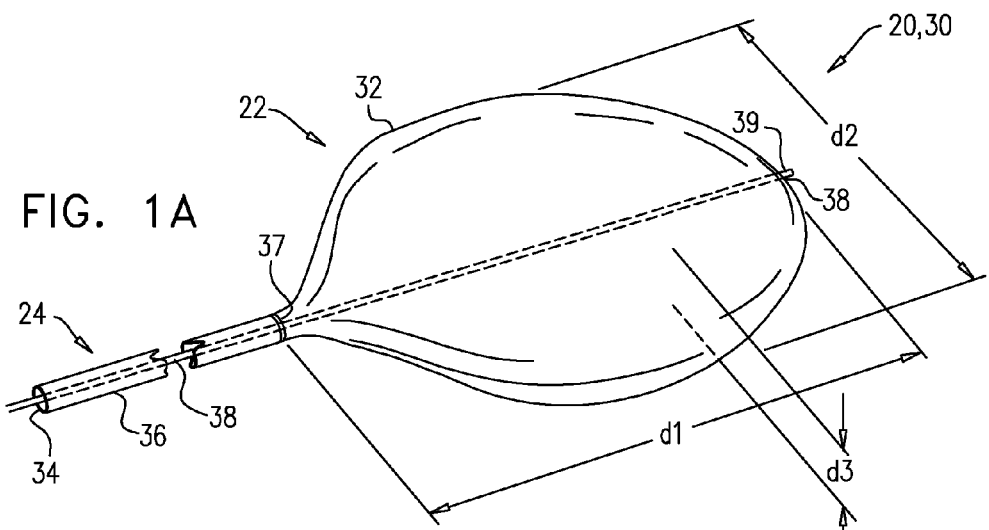
FIGS. 1A-C are schematic illustrations of a reflection-facilitation element, comprising an inflatable element and an introducer, for facilitating tissue ablation in a subject, in accordance with some applications of the invention.

Ultrasound ablation of tissue involves delivering ultrasound energy that directly heats the tissue in the acoustic focal volume (e.g., the target tissue). As with other ablation techniques, it is important to avoid inadvertently damaging other tissues, such as those adjacent to the target tissue. For example, when ablating tissue of the left atrium of a subject (e.g., to treat atrial fibrillation), it is important to avoid inadvertently damaging the nearby esophagus, as well as other adjacent tissues.

An ultrasound transducer is placed on a first side of the target tissue and applies the ultrasound energy to the target tissue. Typically, at least part of the ultrasound energy passes entirely through the target tissue. A reflective region is provided on a second side of the target tissue from the transducer, by a reflection-facilitation element. The reflective region reflects at least part of ultrasound energy that passes through the target tissue, and thereby protects proximate tissues on the second side of the target tissue by inhibiting the energy from continuing into those tissues.

The target tissue absorbs at least part of the energy that arrives directly from the transducer, and at least part of the energy that is reflected by the reflective region. Thereby, as well as protecting proximate tissues on the second side of the target tissue, the presence of the reflective region increases the amount of energy available to be absorbed by the target tissue, resulting in temperature elevation and enhanced ablation of the target tissue. Reflection of the ultrasound energy such that it passes through the tissue for a second time achieves what may be considered a bipolar effect.

For some of the applications described herein, a reflection-facilitation element is used to provide a reflective region by delivering free gas to the second side of the target tissue. For example, the reflection-facilitation element comprises an introducer, such as a needle and/or a tube. The free gas has an acoustic impedance that is different to that of the surrounding tissue (e.g., the target tissue), and thereby reflects at least some of the ultrasound energy that passes through the target tissue, back through the target tissue.

For some of the applications described herein, a reflection-facilitation element is used to provide a reflective region by being reflective itself. For some such applications, the reflection-facilitation element is inflatable with a gas that has an acoustic impedance that is different to that of the target tissue, and thereby reflects at least some of the ultrasound energy that passes through the target tissue, back through the target tissue. Inflatable reflection-facilitation elements may further protect proximate tissues on the second side of the target tissue by increasing a distance between the target tissue and the proximate tissues.

For some applications, the reflective region and/or the reflection-facilitation element facilitates the use of higher energy (e.g., higher intensity and/or density) ultrasound, due to the protective effect. For some applications, the reflective region and/or the reflection-facilitation element facilitates the use of lower energy (e.g., lower intensity and/or density) ultrasound, due to the enhanced ablation effect. For some applications, a focal point of the ultrasound transducer is located in the target tissue, and the ultrasound energy applied is generally capable of ablating the cardiac tissue. For other applications, the ultrasound transducer transmits non-focused ultrasound waves. Additionally or alternatively, the ultrasound transducer transmits low intensity focused or non-focused ultrasound waves.

Thereby, providing a reflective region (e.g., by using a reflection-facilitation element) on the other side of the target tissue to an ultrasound transducer, typically increases the efficacy and/or safety of ultrasound-based ablation.

Figure 1B:
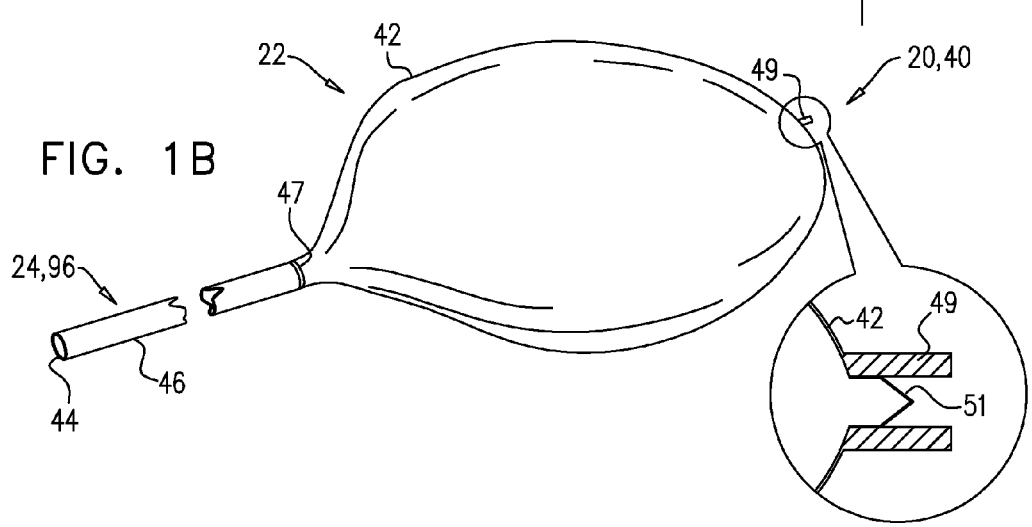
Figure 1C:
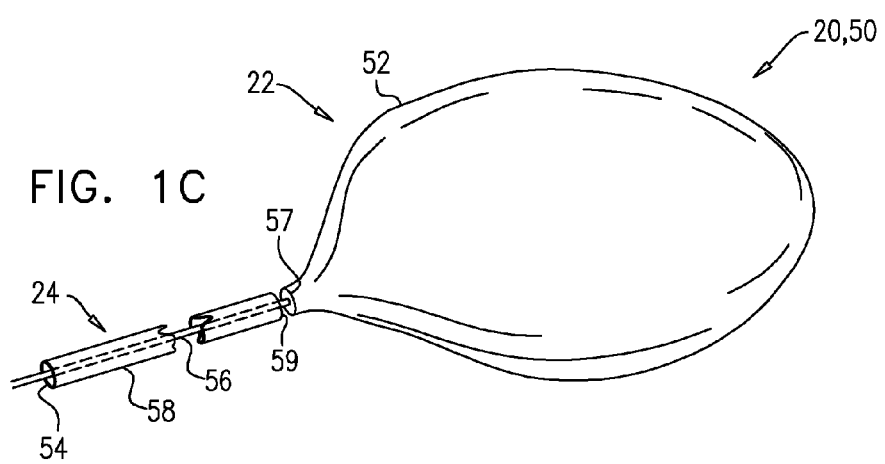

Reference is made to FIGS. 1A-C, which are schematic illustrations of a reflection-facilitation element 20, comprising an inflatable element 22 and an introducer 24 (e.g., a fluid-delivery element), for facilitating tissue ablation in a subject by reflecting ultrasound, in accordance with some applications of the invention. Inflatable element 22 is typically inflatable by delivering an inflation fluid to the inflatable element via introducer 24. Typically, the inflation fluid comprises a gas, but may alternatively comprise a liquid, or a mixture of a gas and a liquid, such as a foam. Introducer 24 is coupled to inflatable element 22, and typically comprises at least one tubular element that is in fluid communication with inflatable element 22.

Introducer 24 is configured to deliver the inflation fluid (1) to the interior of inflatable element 22 (i.e., so as to inflate the inflatable element), and (2) to a site exterior to the inflatable element (e.g., immediately outside of the inflatable element). That is, introducer 24 is configured to deliver a first portion of the inflation fluid to the interior of inflatable element 22, and a second portion of the inflation fluid to the exterior of the inflatable element. For some applications, the first and second portions of the inflation fluid provide distinct reflective regions (e.g., first and second reflective regions, such as reflective regions with a non-reflective region inbetween). For some applications, the first and second portions of the inflation fluid provide a generally continuous reflective region (e.g., the second portion being disposed outside the inflatable element, immediately opposite the first portion).

For some applications, introducer 24 is configured such that the inflation fluid is independently deliverable to the interior and exterior of inflatable element 22 (e.g., such that a user may select respective amounts (e.g., volumes or pressures) of the inflation fluid to be delivered to the interior and exterior of the inflatable element). For some applications, the introducer is configured such that the amount of inflation fluid delivered to the interior of the inflatable element varies with (e.g., is proportionally related to) the amount of inflation fluid delivered to the exterior of the inflatable element.

Reflection-facilitation element 20 (e.g., the inflatable element thereof and/or the introducer thereof) defines (1) an inlet, via which the inflatable element is inflated, and (2) an outlet, via which the inflation fluid is delivered to the exterior of the inflation element (e.g., as described hereinbelow for reflection-facilitation elements 30, 40 and 50).

Typically, inflatable element 22 is configured to be placed in the pericardial cavity of the subject, such that the inflation fluid delivered to the interior and/or exterior of the inflatable element is thereby disposed in the pericardial cavity. That is, (1) the portion of the inflation fluid that is delivered to the interior of the inflatable element is disposed within the inflatable element, within the pericardial cavity, and (2) the portion of the inflation fluid delivered to the exterior of the inflatable element (e.g., via an outlet as described hereinbelow with reference to FIGS. 1A-C) is free within the pericardial cavity. Typically, inflation of inflatable element 22 increases a distance between layers of the pericardium (e.g., between the parietal pericardium and the visceral pericardium).

For some applications of the invention, inflatable element 22 comprises an anti-inflammatory substance. For example, inflatable element 22 may be coated in an immobilized and/or biosorbent anti-inflammatory drug.

In FIGS. 1A-C, inflatable element 22 is shown as having a somewhat oval shape, but element 22 may have a different shape (e.g., as described with reference to FIGS. 5A-I, mutatis mutandis), and/or may have an adjustable shape (e.g., as described with reference to FIGS. 29A-B, mutatis mutandis). For some applications, when inflated and not externally constrained (e.g., if element 22 is inflated while sitting on a table), inflatable element 22 has a flattened shape. That is, for some applications, element 22 has a thickness d3 that is smaller than a length d1 or a width d2 thereof.

FIG. 1A shows reflection-facilitation element 20, embodied as a reflection-facilitation element 30. Element 30 comprises inflatable element 22, embodied as an inflatable element 32, and introducer 24, embodied as an introducer 34. Introducer 34 comprises two or more tubular elements, such as a first tubular element 36 and a second tubular element 38, each tubular element shaped to define a respective lumen. FIG. 1A shows tubular elements 36 and 38 as coaxial. However, it is to be noted that elements 36 and 38 may be arranged differently, such as parallel to each other.

Tubular element 36 is in fluid communication with inflatable element 32. For example, an end (e.g., a distal end) of element 36 may open into a proximal side of element 32, the opening into element 32 defining a port (e.g., an inlet 37). Tubular element 38 is typically not in fluid communication with element 32, but extends through element 32 so as to be in fluid communication with a site external to element 32 that is on a distal side of element 32. The distal end of tubular element 38 thereby defines a port (e.g., an outlet 39). Thereby, introducer 34 is configured to deliver inflation fluid (1) to the interior of inflatable element 32 via tubular element 36, and (2) to a site exterior to the inflatable element via tubular element 38.

FIG. 1B shows reflection-facilitation element 20, embodied as a reflection-facilitation element 40. Element 40 comprises inflatable element 22, embodied as an inflatable element 42, and introducer 24, embodied as an introducer 96. Introducer 96 comprises at least one tubular element 46, shaped to define a lumen, and an outlet 49.

Tubular element 46 is in fluid communication with inflatable element 42. For example, an end (e.g., a distal end) of element 46 may open into a proximal side of element 42, the opening into element 42 defining a port (e.g., an inlet 47). Outlet 49 is typically not directly coupled to element 42, but is disposed at a distal side of element 42 so as to provide fluid communication between the interior of element 42 and a site external to element 42 that is on a distal side of element 42. Thereby, outlet 49 typically provides fluid communication between tubular element 46 and the site external to element 42 that is on a distal side of element 42. Thereby, introducer 96 is configured to deliver inflation fluid (1) to the interior of inflatable element 42 via tubular element 46, and (2) to a site exterior to the inflatable element via outlet 49. Alternatively, outlet 49 is disposed at a different site on the inflatable element, e.g., near inlet 47, between inlet 47 and outlet 49.

Typically, outlet 49 comprises a fluid-control device, such as a valve 51. For some applications, the valve is configured to allow the inflation fluid to flow from inflatable element 42 to the site exterior to the inflatable element (i.e., through outlet 49) only when a pressure at the site exterior to the inflatable element is lower than a threshold value. For some applications, the valve is configured to allow the inflation fluid to flow through outlet 49 only when a pressure within inflatable element 42 is greater than a threshold value. For some applications, the threshold values are absolute values (e.g., pressures). For some applications, the threshold values are relative values (e.g., relative to each other). For example, the valve may be in an open state if the difference in pressure between the inside of inflatable element 42 and the site exterior to the inflatable element is greater than a threshold value.

FIG. 1C shows reflection-facilitation element 20, embodied as a reflection-facilitation element 50. Element 50 comprises inflatable element 22, embodied as an inflatable element 52, and introducer 24, embodied as an introducer 54. Introducer 54 comprises two or more tubular elements, such as a first tubular element 56 and a second tubular element 58, each tubular element shaped to define a respective lumen. FIG. 1A shows tubular elements 56 and 58 as coaxial. However, it is to be noted that elements 56 and 58 may be arranged differently, such as parallel to each other.

Tubular element 56 is in fluid communication with inflatable element 52. For example, an end (e.g., a distal end) of element 56 may open into a proximal side of element 52, the opening into element 52 defining a port (e.g., an inlet 57). Tubular element 58 is typically not in fluid communication with element 52, but is in fluid communication with a site external to element 52 that is on a proximal side of element 52. For example, and as shown in FIG. 1C, tubular element 58 may define a distal opening (i.e., tubular element 58 may end proximal to inflatable element 52). Alternatively, element 58 may define a lateral opening close to the distal end thereof. The distal end of tubular element 58 thereby defines a port (e.g., an outlet 59). Thereby, introducer 54 is configured to deliver inflation fluid (1) to the interior of inflatable element 52 via tubular element 56, and (2) to a site exterior to the inflatable element via tubular element 58.

It is noted that the position of the inlets and outlets described with reference to FIGS. 1A-C are for illustration, and are not limiting. For example, although outlets 39 and 49 are described as being at a distal side of inflatable elements 32 and 42, respectively, the outlets may be disposed at other sites with respect to the inflatable elements (e.g., according to the procedure being performed and/or the placement of the reflection-facilitation apparatus with respect to the anatomy of the subject).

For some applications of the invention, reflection-facilitation element 20 (e.g., inflatable element 22 and/or introducer 24) defines one or more lumens configured to be slidable over a guidewire, for facilitating delivery of the inflatable element to the desired location.

Reference is made to FIGS. 2A-F, which are schematic illustrations of a system 80 for application of ultrasound energy to tissue within a body of a subject, in accordance with some applications of the present invention. System 80 comprises an ultrasound tool 90 and reflection-facilitation element 20. Ultrasound tool 90 comprises at least one ultrasound transducer 92, and is typically delivered via a catheter 88. For some applications, and as shown in FIGS. 2A-F, ultrasound tool 90 comprises a rotatable ultrasound tool, as described in the subsequent paragraph. Alternatively, ultrasound tool may comprise another ultrasound tool, such as an ultrasound tool that is configured to apply ultrasound energy in 360 degrees (e.g., in an annular focal pattern), e.g., due to its shape (e.g., as described with reference to FIGS. 7-8 and 10A-B, mutatis mutandis), or by using phased array techniques (e.g., as described with reference to FIGS. 27A-B, mutatis mutandis).

As shown in FIGS. 2A-F, for applications in which ultrasound tool 90 comprises a rotatable ultrasound tool, the ultrasound tool typically comprises a proximal shaft 94, which may house a distal shaft 93, which comprises a hinge 196. The hinge connects the proximal and distal portions, and facilitates rotation and/or deflection of different elements of the ultrasound tool, such as lateral deflection of arm 102 with respect to distal shaft 93. (In this context, in the specification and in the claims, "proximal" means closer to the orifice through which the tool is originally placed into the body, and "distal" means further from this orifice.) For some applications, distal shaft 93 comprises a telescopically collapsible and extendable element 106, which facilitates the telescopic extension and collapse of the distal shaft. For some such applications, distal shaft 93 comprises an arm 102 that is coupled to hinge 196. Arm 102 typically comprises, at a distal end thereof, the at least one ultrasound transducer 92. For some applications, ultrasound tool 90 further comprises an anchoring element 98, which is configured to temporarily stabilize the tool during application of the ultrasound energy, e.g., by temporarily anchoring the distal end of tool 90 in a blood vessel 104, such as a pulmonary vein. For some applications, as shown in the figures, anchoring element 98 comprises an inflatable element 100 (shown in FIGS. 2C-F in its inflated state), inflatable via a conduit 108. It is to be noted that anchoring element 98 may alternatively comprise another anchoring element known in the art, including a guidewire.

Ultrasound tool 90 is introduced into a chamber 110 of the heart (e.g., a left atrium of the heart) (FIG. 2A), and is positioned for use and optionally anchored (FIGS. 2B-C) For example, tool 90 may (1) be disposed in an area that is adjacent to an orifice of blood vessel 104, e.g., adjacent to a pulmonary vein ostium in the left atrium of the heart (e.g., as described with reference to FIGS. 3A-4B, 7, and/or 27A-B, mutatis mutandis), and (2) configured to ablate tissue in a vicinity of the orifice of the blood vessel in order to electrically isolate the blood vessel. It is to be understood that the scope of the present invention includes disposing tool 90 in any chamber of the heart, including the right atrium, or the left or right ventricle, for treatment of tissue thereof. For example, system 80 and/or components thereof may be used to ablate tissue in a ventricle for treatment of ventricular tachycardia.

Figure 2A:
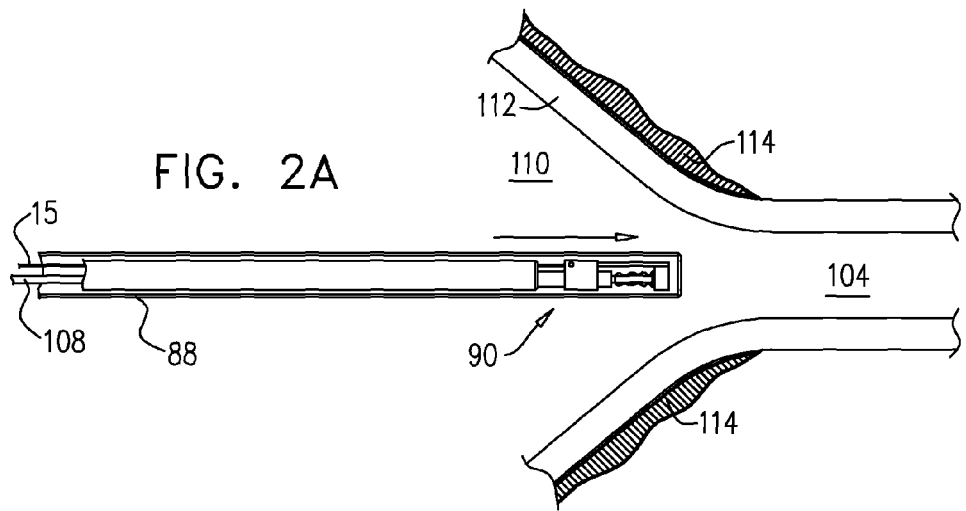
Figure 2B:
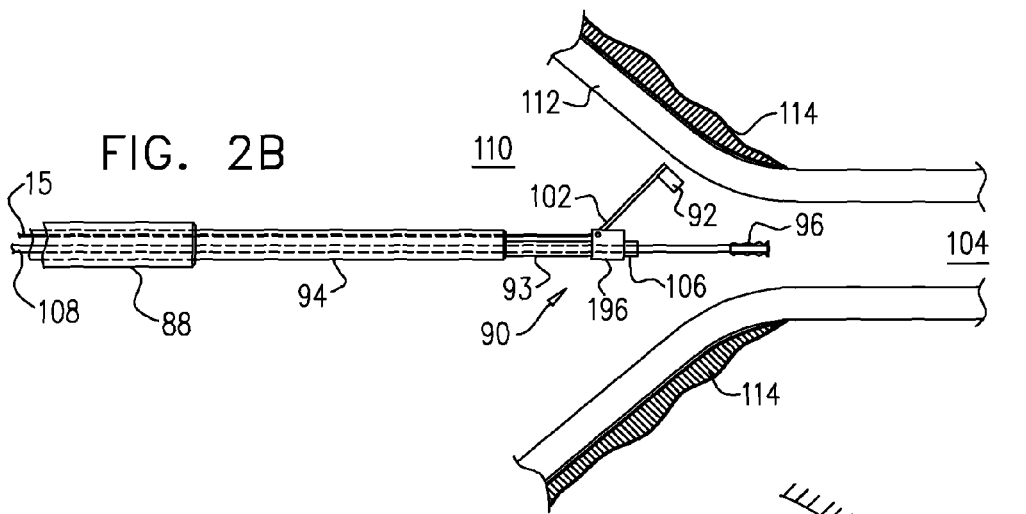
Figure 2C:
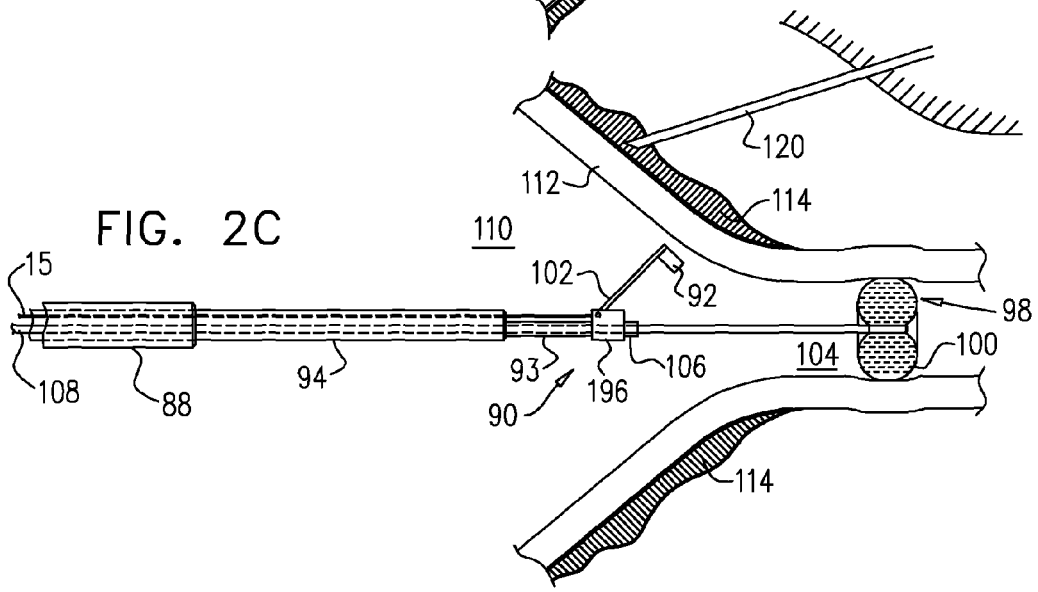

FIG. 2C schematically shows a distal end of a catheter 120, having been delivered to the pericardial cavity 114 of the subject, so as to facilitate delivery of reflection-facilitation element 20 thereto. Typically, element 20 (e.g., inflatable element 22 thereof) is delivered intracatheterally, such as, but not limited to, via a subxiphoid approach or via the central port, under the collarbone. Optionally, a small camera is inserted with element 20 to provide image guidance during the insertion procedure. Any approach suitable to obtain pericardial access may typically be used. Typically, an approach is selected according to the site in the pericardial cavity at which inflatable element 22 is to be placed. Non-limiting examples of positions within the pericardial cavity in which inflatable element 22 may be placed, are described hereinbelow, such as with reference to FIGS. 3A-5I, 18, and 22A-24B, mutatis mutandis.

FIG. 2D shows inflatable element 22 having been delivered from the distal end of catheter 120 into pericardial cavity 114, and inflated with a portion 123 (e.g., a first portion) of an inflation fluid 122. In this application of the invention, introducer 24 (FIGS. 1A-C) remains within catheter 120, and is not shown. Typically, inflation fluid 122 comprises a gas. Inflation of inflation element 22 typically increases a distance between layers of the pericardium (e.g., between the parietal pericardium and the visceral pericardium) at least in the vicinity of the inflation element (i.e., increasing the volume of pericardial cavity 114 in that vicinity).

FIG. 2E shows a portion 124 (e.g., a second portion) of inflation fluid 122 having been delivered to the exterior of inflatable element 22, such that the portion of the inflation fluid is free within pericardial cavity 114. Typically, portion 124 is thereby in contact with the outer surface of element 22. Typically, portion 124 comprises the same fluid as does portion 123. For some applications, portion 124 comprises a different fluid than does portion 123. Delivery of portion 124 to the pericardial cavity typically increases a distance between layers of the pericardium (e.g., between the parietal pericardium and the visceral pericardium) at least in the vicinity of the inflation fluid (i.e., increasing the volume of pericardial cavity 114 in that vicinity).

Inflation fluid 122 has an acoustic impedance that is different to that of the surrounding tissue. Typically, the inflation fluid comprises a gas of lower density than the surrounding tissue. Delivery of inflation fluid 122 to the interior and exterior of inflatable element 22 (i.e., inflating inflatable element 22 and delivering inflation fluid free into the pericardial cavity) thereby provides at least one reflective region on the other side of cardiac tissue 112 from tool 90). For example, portion 123 may provide one reflective region and portion 124 may provide another reflective region, or portions 123 and 124 may provide one continuous reflective region.

Ultrasound energy is applied to tissue 112 using tool 90 (e.g., transducer 92 thereof), directly heating the tissue in the acoustic focal volume (FIG. 2E). At least part of the ultrasound energy passes entirely through the tissue and at least part of that energy is reflected by inflation fluid 122 (e.g., portions 123 and 124 thereof), back through the tissue (FIG. 2F). The reflective region(s) provided by the reflection-facilitation element thereby typically increases efficacy and/or safety of the ultrasound-based ablation, as described hereinabove.

For some applications of the invention, transducer 92 is configured to generate ultrasound energy at more than one frequency and/or with more than one focal point. For example, transducer 92 may generate (1) first ultrasound energy, e.g., at a frequency of greater than 7 MHz and/or less than 11 MHz (e.g., 9 MHz), and that has a focal point within the tissue of the target site, and (2) second ultrasound energy at a frequency lower than the frequency of the first ultrasound energy (e.g., of greater than 2 MHz and/or less than 6 MHz (e.g., 4 MHz)), that has a focal point on the other side of the tissue of the target site. The second ultrasound energy is thereby typically reflected by the reflective region (e.g., by inflation fluid 122), such that it too focuses on the tissue of the target site.

For applications in which tool 90 comprises a rotatable ultrasound tool, the tool is rotated (e.g., as indicated by arrow 14A and/or in the opposite direction), such that ultrasound transducer 92 can be aimed at any desired location around an orifice of blood vessel 104. Rotation of tool 90 allows circumferential ablation surrounding the orifice of blood vessel 104, e.g., a pulmonary vein ostium, such that blood vessel 104 is electrically isolated from other areas of the heart, thereby blocking conduction of undesired electrical signals from blood vessel 104 into the heart, such as for treatment of atrial fibrillation. Thus, tool 90 or an element thereof is typically rotated a full 360 degrees around a longitudinal axis of tool 90.

Alternatively, and as described above, for some applications, tool 90 is configured to apply ultrasound energy in 360 degrees, such as in an annular focal pattern (e.g., as described with reference to FIGS. 7-8, 10A-B, and/or 27A-B, mutatis mutandis). For such applications, tool 90 is not typically rotated.

Reference is again made to FIGS. 1A-2F. Typically, inflatable element 22 functions to facilitate retention of inflation fluid 122 at a site in the pericardial cavity from which, in the absence of the inflatable element, the inflation fluid would be displaced. In other words, based on the anatomy of the patient, the position of the patient, and other factors, if the pericardial cavity were directly inflated without using the inflatable element, it may be that some or all of the inflation fluid would be displaced from the desired location (e.g., as described with reference to FIG. 25, mutatis mutandis). For some such applications, inflatable element 22 facilitates retention of the inflation fluid by virtue of inflation fluid 122 (e.g., portion 123 thereof) being held within the inflatable element. For some such applications, inflatable element 22 additionally facilitates retention of the inflation fluid by increasing a distance between layers of the pericardium, and thereby retaining a space in which inflation fluid 122 (e.g., portion 124 thereof) may be disposed. For some applications of the invention, inflatable element 22 is inflated with a fluid that may or may not provide a reflective region, but functions solely to increase the distance between layers of the pericardium.

Reference is again made to FIGS. 2A-F. Although tool 90 is shown to be delivered to the heart chamber before inflation element 22 is delivered to the pericardial cavity and/or inflated, it is to be noted that tool 90 may be delivered subsequent to, and/or simultaneously with, the delivery and/or inflation of inflation element 22.

Reference is again made to FIGS. 2A-F. For some applications, system 80 is configured to sense a temperature of the target site (e.g., to determine when ablation has been achieved, such as by sensing that a desired temperature of 60 to 80 degrees has been obtained). For such applications, tool 90 typically comprises an ultrasound detector (which may comprise transducer 92, or may comprise a distinct detector). For such applications, transducer 92 applies (e.g., transmits) one or more pulses of ultrasound energy (e.g., non-ablating pulses of ultrasound energy), which are reflected by the reflective region and subsequently detected by the ultrasound detector. The temperature of the target site is determined at least in part responsively to the time between transmission and detection of the ultrasound energy, known as time of flight (TOF).

For example, the speed of sound in the target site generally varies with the temperature of the target tissue. Typically, the speed of sound in cardiac muscle increases as the temperature of the cardiac muscle increases. A first pulse of ultrasound energy is transmitted by transducer 92, reflected, and detected by the ultrasound detector, and the TOF is determined. The TOF of the first pulse is dependent on the temperature of the target site (i.e., the tissue thereof) and the distance to the reflective region. The TOF of a second pulse of ultrasound energy is determined, and the difference between the TOF of the first and second pulses is used to determine a the temperature of the target site and/or a temperature change of the target site. Typically, the distance between tool 90 (i.e., the transducer and the ultrasound detector) and the reflective region is maintained between the two pulses.

Typically, the first pulse is transmitted before an ablative pulse of ultrasound energy is transmitted, and the second pulse is transmitted after the ablative pulse of ultrasound energy is transmitted.

Figure 3A:
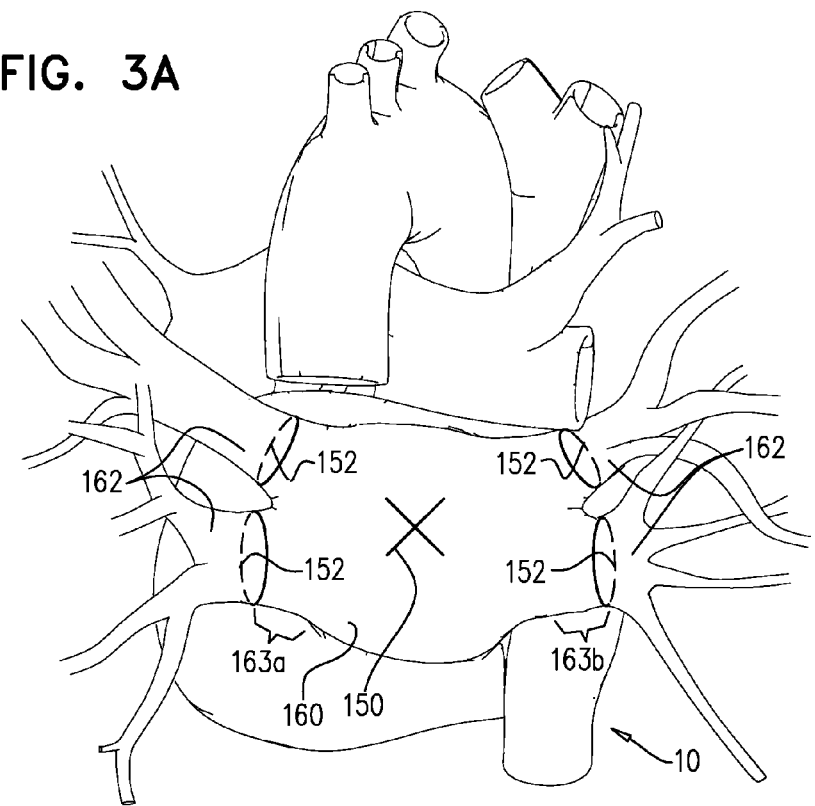
FIGS. 3A-B are schematic illustrations of ablation sites and a placement site for the inflatable element, in accordance with some applications of the invention.
Figure 3B:
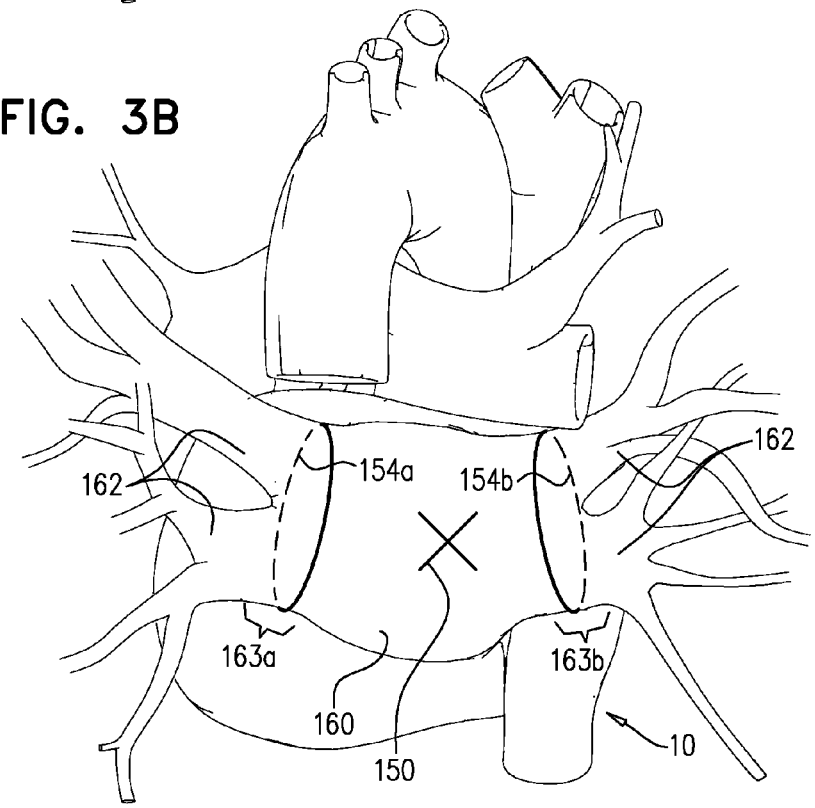

Reference is made to FIGS. 3A-B, which are schematic illustrations of ablation sites (e.g., ablation patterns) and a placement site 150 for inflatable element 22, in accordance with some applications of the invention. FIGS. 3A-B show the posterior side of heart 10 of the subject. For clarity, the pericardium is not shown in FIGS. 3A-B. So as to electrically isolate left atrium 160 of heart 10 from pulmonary veins 162, cardiac tissue adjacent to one or more pulmonary vein ostia is ablated. For some applications of the invention, one or more ablation sites 152 are generated that circumscribe the tissue adjacent to respective ostia, such as shown in FIG. 3A. Thereby, to isolate all four pulmonary veins, four circumscribing ablation sites 152 are generated.

For some applications of the invention, one or more ablation sites 154 (e.g., ablation sites 154a and 154b) are generated that circumscribe the tissue adjacent to and/or within respective common ostia 163a and 163b, such as shown in FIG. 3B. Thereby, to isolate all four pulmonary veins, two circumscribing ablation sites are generated; one ablation site that isolates the left superior and inferior pulmonary veins, and another ablation site that isolates the right superior and inferior pulmonary veins.

It is typically desirable to provide the reflective region adjacent to as much as possible of the tissue to be ablated (e.g., to provide the reflective region adjacent to most of the tissue, for example all of the tissue to be ablated). For applications of the invention in which the ablation site(s) are at or near the left atrium, it is thereby desirable to provide the reflective region at least in a posterior region of the pericardial cavity (i.e., posterior to the heart, adjacent to the left atrium). During a typical cardiac tissue ablation procedure, the subject is in a supine position, and the weight of the heart rests on the posterior portion of the pericardium, thereby typically displacing (e.g., squeezing out) at least part of the pericardial fluid disposed in this portion of the pericardium, e.g., into an anterior portion of the pericardium. Similarly, for some applications in which only free fluid (e.g., gas) is introduced to the pericardial cavity so as to provide the reflective region, the introduced fluid is displaced.

Typically, inflatable element 22 (e.g., a part thereof) is placed within the pericardial cavity at placement site 150, which is posterior to the heart, and thereby below the heart when the subject is in the supine position. It is hypothesized that the placement of inflatable element 22 at placement site 150, reduces the displacement of inflation fluid 122 (i.e., portion 124 thereof) from the posterior region of the pericardium, that would otherwise occur if portion 124 were delivered in the absence of inflatable element 22.

It is further hypothesized that the placement of inflatable element 22 at placement site 150 increases a distance between the ablation site and other tissue. For example, the esophagus is generally immediately posterior to the heart, and esophageal injury is an established risk in ablation treatments for atrial fibrillation. For some applications, when placed at placement site 150, inflatable element 22 increases a distance between left atrium 160 (and thereby the ablation site) and the esophagus, thereby reducing the risk of esophageal injury.

At sites at which inflatable element 22 contacts the tissue (e.g., the visceral pericardium) close to the ablation site (e.g., when the inflatable element is opposite transducer 92), the inflatable element 22 (and/or portion 123 of inflation fluid 122 therein) typically provides (e.g., acts as) the reflective region. At sites at which portion 124 of inflation fluid 122 contacts the tissue (e.g., the visceral pericardium) close to the ablation site (e.g., when the free inflation fluid is opposite transducer 92), portion 124 of the inflation fluid typically provides (e.g., acts as) the reflective region.

Figure 4A:
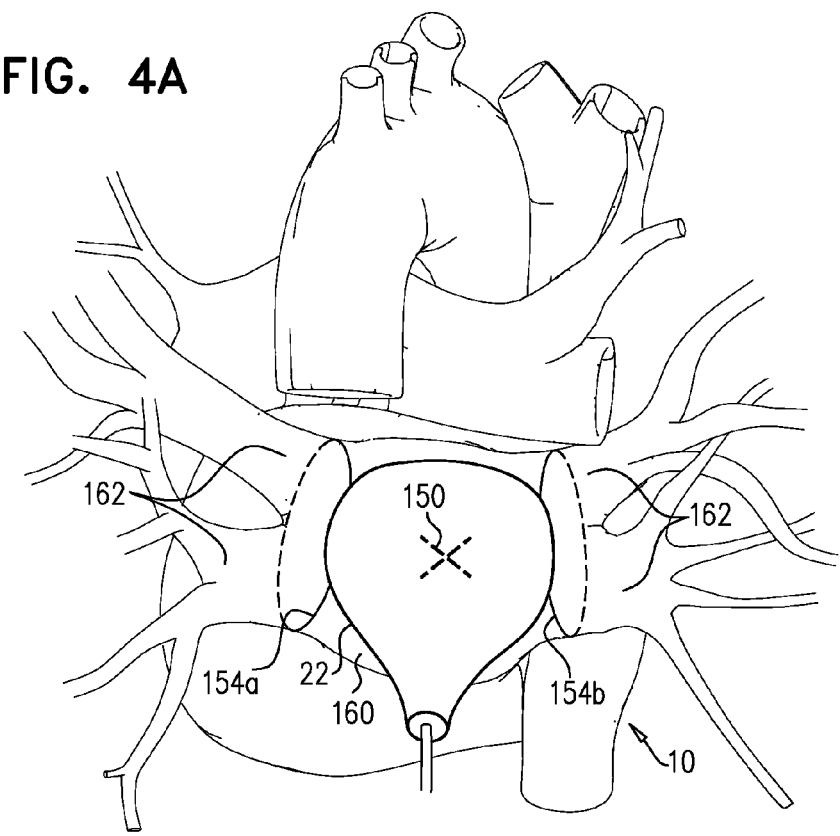
FIGS. 4A-B are schematic illustrations of the inflatable element of the reflection-facilitation element having been placed at the placement site, in accordance with some applications of the invention.
Figure 4B:
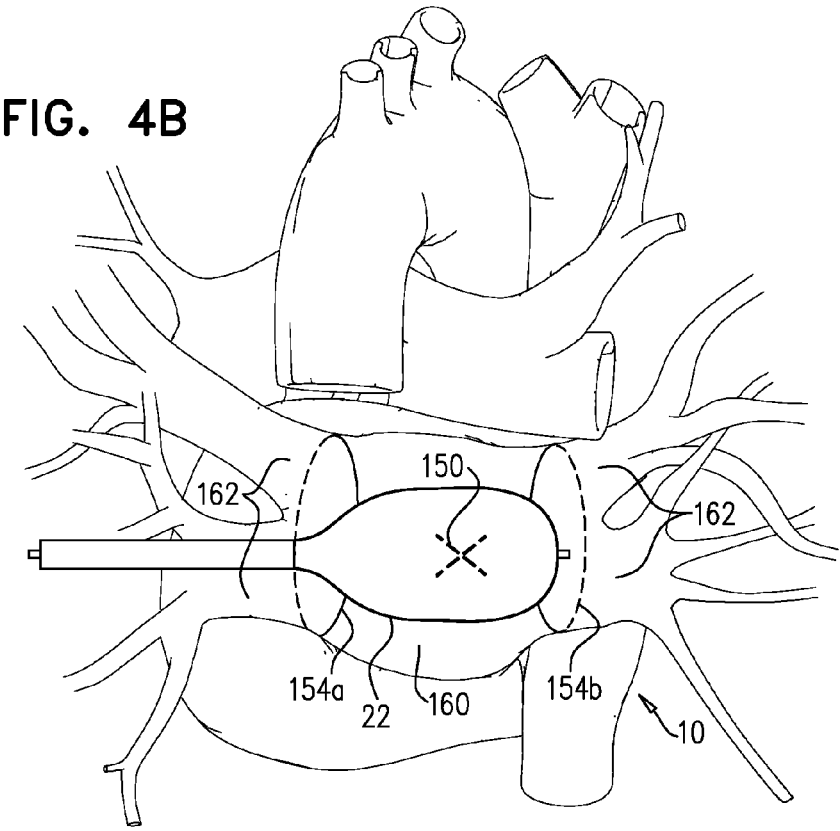

Reference is made to FIGS. 4A-B, which are schematic illustrations of inflatable element 22 of reflection-facilitation element 20, having been placed at placement site 150, in accordance with some applications of the invention. FIGS. 4A-B show the posterior side of heart 10 of the subject. For clarity, the pericardium is not shown in FIGS. 4A-B. FIGS. 4A-B show reflection-facilitation element 20 as similar to reflection-facilitation element 30, described with reference to FIG. 1A, but it should be noted that the invention includes any embodiment of reflection-facilitation element 20 being placed at placement site 150. FIGS. 4A-B show ablation sites 154 as an example, and it should be noted that other ablation sites (e.g., ablation sites 152, described with reference to FIG. 3A) may also be used.

FIG. 4A shows element 20 having been delivered to placement site 150 via the inferior side of the heart. FIG. 4B shows element 20 having been delivered to placement site 150 via the left side of the heart. Typically, delivery is achieved via a subxiphoid approach, as is known in the art. For some applications of the invention, delivery is achieved via an intercostal approach.

Element 20 is typically delivered in a deflated state thereof. Further typically, element 20 is delivered intracatheterally. For some applications, element 20 is coupled to a semi-rigid spine that facilitates steering of element 20. For some applications in which element 20 is coupled to a semi-rigid spine, element 20 is delivered without a catheter (e.g., element 20 is delivered exposed). For some applications, element 20 comprises a miniature forceps (e.g., coupled to a distal part of inflatable element 22 or a delivery catheter), which facilitate separation (e.g., blunt dissection) of tissues, and thereby delivery of element 20. For some applications, inflatable element 22 is inflated during delivery so as to facilitate separation of tissues (e.g., blunt dissection), and thereby delivery of element 20. For some applications, this inflation of element 22 comprises inflation of a compartment (e.g., a sub-compartment) of element 22, e.g., with a liquid.

Typically, element 20, element 22, introducer 24, and or the delivery catheter thereof, comprise one or more radiopaque markers, to facilitate location of the apparatus during delivery. The radiopaque markers may also be used to indicate a degree of inflation of inflatable element 22, and to facilitate location of the apparatus during removal from the body of the subject.

Following delivery and inflation of inflatable element 22, portion 124 of inflation fluid 122 is delivered to the pericardial cavity (i.e., free), so as to provide at least part of the reflective region. Portion 124 is not shown in FIGS. 4A-B. As described hereinabove, the presence of inflated inflatable element 22 reduces the displacement of portion 124 from the posterior region of the pericardium (and for some applications, further provides at least part of the reflective region). Portion 124 of inflation fluid 122 may be disposed at various locations within the pericardium, including posterior to the heart (e.g., adjacent to inflatable element 22. Typically, at least part of portion 124 is disposed more anteriorly than element 22, such as between and/or anterior to pulmonary veins 162. For some applications, at least part of portion 124 is disposed inferior to the heart of the subject.

For some applications, an embodiment of reflection-facilitation element 20 is selected according to the position of the outlet thereof, thereby at least in part directing the delivery of portion 124. Typically, the anatomy of the pericardium at least in part restricts movement of portion 124 of the inflation fluid. For example, anatomical structures, such as pericardial reflections typically trap the inflation fluid. For some applications, structures (e.g., flaps and/or pockets) on the exterior of inflatable element 22 facilitate the trapping of the inflation fluid.

Reference is made to FIGS. 5A-I, which are schematic illustrations of inflatable element 22, in accordance with respective applications of the invention. FIGS. 5A-I show some embodiments of element 22, each embodiment having (e.g., defining) an inlet and an outlet, as described hereinabove. An example flow path for portion 124 of inflation fluid 122 (FIG. 2E) is shown on each embodiment as a dash-dot line. The inlets and outlets in FIGS. 5A-I are solely illustrative, may be interchanged, and/or may be disposed at any site on the inflatable element. Furthermore, for some applications of the invention, the outlet is defined solely by introducer 24, and thereby inflatable element 22 comprises only an inlet (e.g., as described with reference to FIG. 1C). For some applications, the embodiments of inflatable element 22 described with reference to FIGS. 5A-I may have (e.g., may comprise and/or define) any of the inlets and/or outlets described with reference to FIGS. 1A-C. Therefore, the inlets and outlets are not labeled in FIGS. 5A-I.

FIG. 5A shows inflatable element 22, embodied as an inflatable element 200, in accordance with some applications of the invention. Element 200 is shaped to define at least one concave portion 202, and one or more protruding portions 204. Typically, element 200 defines two protruding portions 204a and 204b. Typically, inflatable element 200 is positioned within the pericardial cavity, toward the left side of heart 10, such that (1) at least part of left common ostium 163a is disposed within the concavity of concave portion 202, (2) one of the protruding portions is disposed posterior to the left common ostium, and (3) another protruding portion is disposed anterior to the left common ostium. For some applications, inflatable element 200 is positioned such that at least part of one or more of the left pulmonary veins is disposed within the concavity of concave portion 202.

FIG. 5B shows inflatable element 22, embodied as an inflatable element 210, in accordance with some applications of the invention. Element 210 is shaped to define a bulbous portion 212 and at least one protruding portion 214. Typically, element 210 defines a concavity 216 where the protruding portion meets the bulbous portion. Typically, inflatable element 210 is positioned within the pericardial cavity, toward the left side of heart 10, such that (1) at least part of left common ostium 163a is disposed within concavity 116, (2) bulbous portion 212 is disposed posterior to the left common ostium, and (3) protruding portion 214 is disposed anterior to the left common ostium. For some applications, inflatable element 200 is positioned such that at least part of one or more of the left pulmonary veins is disposed within concavity 216.

FIGS. 5C-D show inflatable element 22, embodied respectively as inflatable elements 220 and 230, in accordance with some applications of the invention. Inflatable elements 220 and 230 are each typically positioned within the pericardial cavity posterior to the left atrium.

FIGS. 5E-F show inflatable element 22, embodied respectively as inflatable elements 240 and 250, in accordance with some applications of the invention. Inflatable elements 220 and 230 are each shaped to define bulbous portions 242 and 252, respectively, and tail portions 244 and 254, respectively. Typically, inflatable elements 240 and 250 are positioned within the pericardial cavity such that (1) the bulbous portion is disposed posterior to the left atrium, and (2) the tail portion extends around the left side of the heart (e.g., inferior to, or between, the left pulmonary veins). For some applications, inflatable elements 240 and 250 comprise one or more supports 246 and 256, respectively. The supports typically support elements 240 and 250 in a pre-selected configuration. The supports may comprise regions of thickened and/or strengthened material, and/or an additional material, such as a metallic wire.

FIGS. 5G-I show inflatable element 22, embodied respectively as inflatable elements 260, 270 and 280, in accordance with some applications of the invention. Elements 260, 270 and 280 are each shaped to define central portions 262, 272 and 282, respectively, and two extended portions 264, 272 and 284, respectively. Typically, inflatable elements 260, 270 and 280 are positioned within the pericardial cavity such that (1) the central portion is disposed posterior to the left atrium, and (2) each extended portion is disposed posterior to a respective common ostia. For some applications, the inflatable elements are positioned such that each extended portion is disposed posterior to one or more pulmonary veins.

Figure 6:
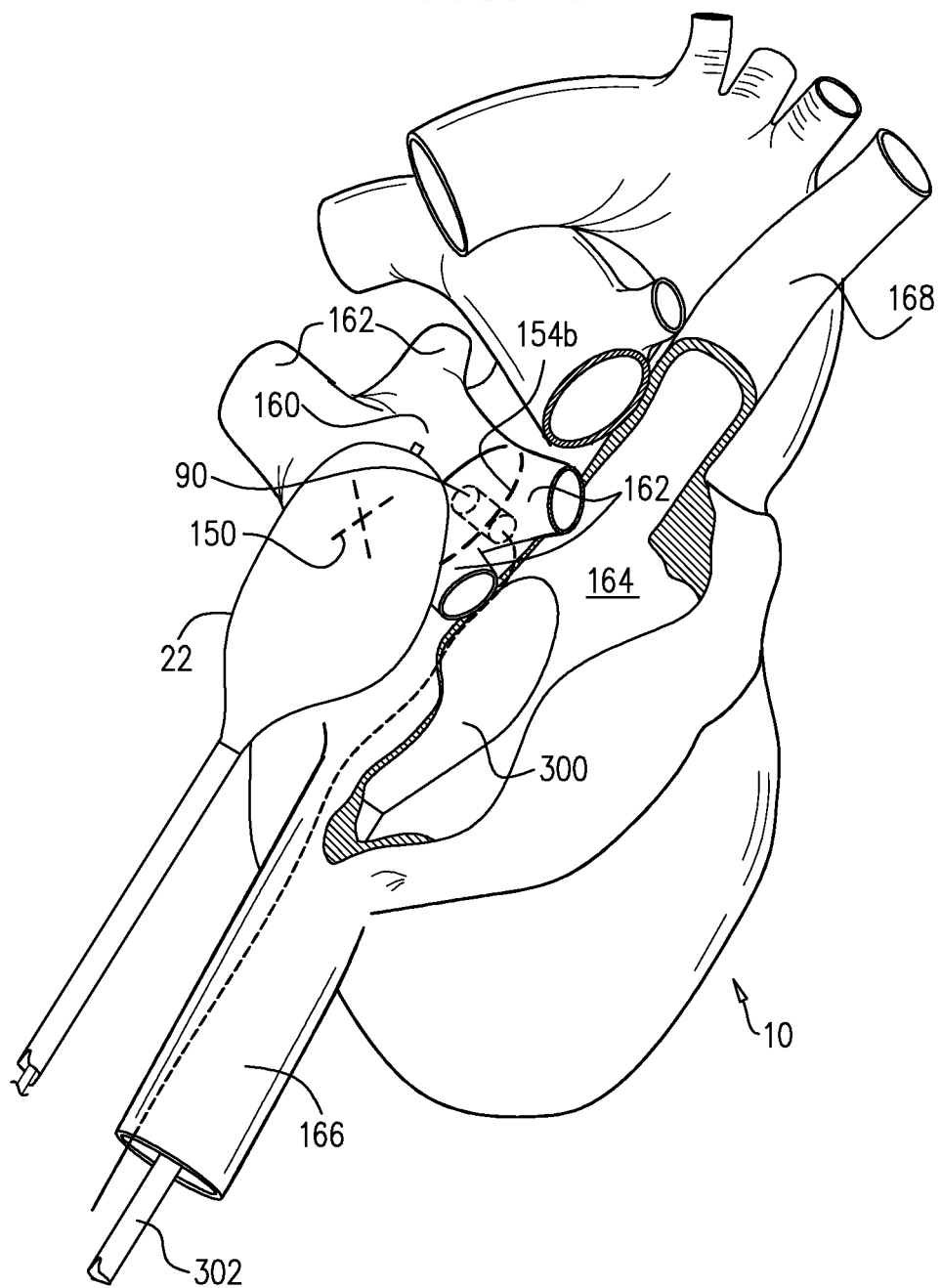
FIG. 6 is a schematic illustration of the reflection-facilitation element and the ultrasound tool being used in combination with an additional inflatable element, in accordance with some applications of the invention.

Reference is made to FIG. 6, which is a schematic illustration of reflection-facilitation element 20 and ultrasound tool 90 being used in combination with an additional inflatable element 300, in accordance with some applications of the invention. FIG. 6 shows heart 10 from the posterior right side. For clarity, the pericardium is not shown in FIG. 6. Tool 90 is advanced into left atrium 160, and reflection-facilitation element 20 is advanced into the pericardial cavity such that inflatable element 22 is disposed posterior to the left atrium. That is, tool 90 and element 20 are positioned so as to ablate tissue, as described hereinabove. Typically, tool 90 and element 20 are positioned so as to ablate tissue at one or more ablation sites adjacent to a right common ostium and/or one or more right pulmonary arteries. FIG. 6 shows tool 90 and element 20 positioned so as to ablate tissue at ablation site 154b, as described hereinabove.

Additional inflatable element 300 is delivered to right atrium 164 of the subject. Typically, additional inflatable element 300 is delivered transluminally, such as by advancing the inflatable element through inferior vena cava (IVC) 166 or superior vena cava (SVC) 168. However, the scope of the invention includes delivering element 300 to the right atrium using any suitable means. Additional inflatable element 300 is inflated (e.g., with inflation fluid 122) via an introducer 302.

As described hereinabove, reflection-facilitation element 20 provides at least one reflective region on the other side of the target tissue from tool 90. At least one region of ablation site 154b includes part of the interatrial septum (not shown). Thereby, for at least one region of ablation site 154b, the other side of the target tissue is within the right atrium. Additional inflatable element 300 provides a reflective region at the right-atrial surface of the interatrial septum, thereby facilitating ablation of the region of ablation site 154b that includes part of the interatrial septum, thereby facilitating the generation of a 360-degree ablation site, and thereby facilitating the electrical isolation of at least one pulmonary vein from the left atrium.

Although FIG. 6 shows additional inflatable element 300 being used to facilitate ablation at ablation site 154b, it is noted that element 300 may be used to facilitate ablation at other ablation sites described herein, such as one or more ablation sites 152. It is further noted that additional inflatable element 300 may be used to provide a reflective region so as to facilitate ablation of any cardiac tissue, either with ultrasound tool 90 alone, or in combination with reflection-facilitation element 20. For example, element 300 may be placed in the left atrium and/or in a ventricle of the heart of the subject.

Figure 7:
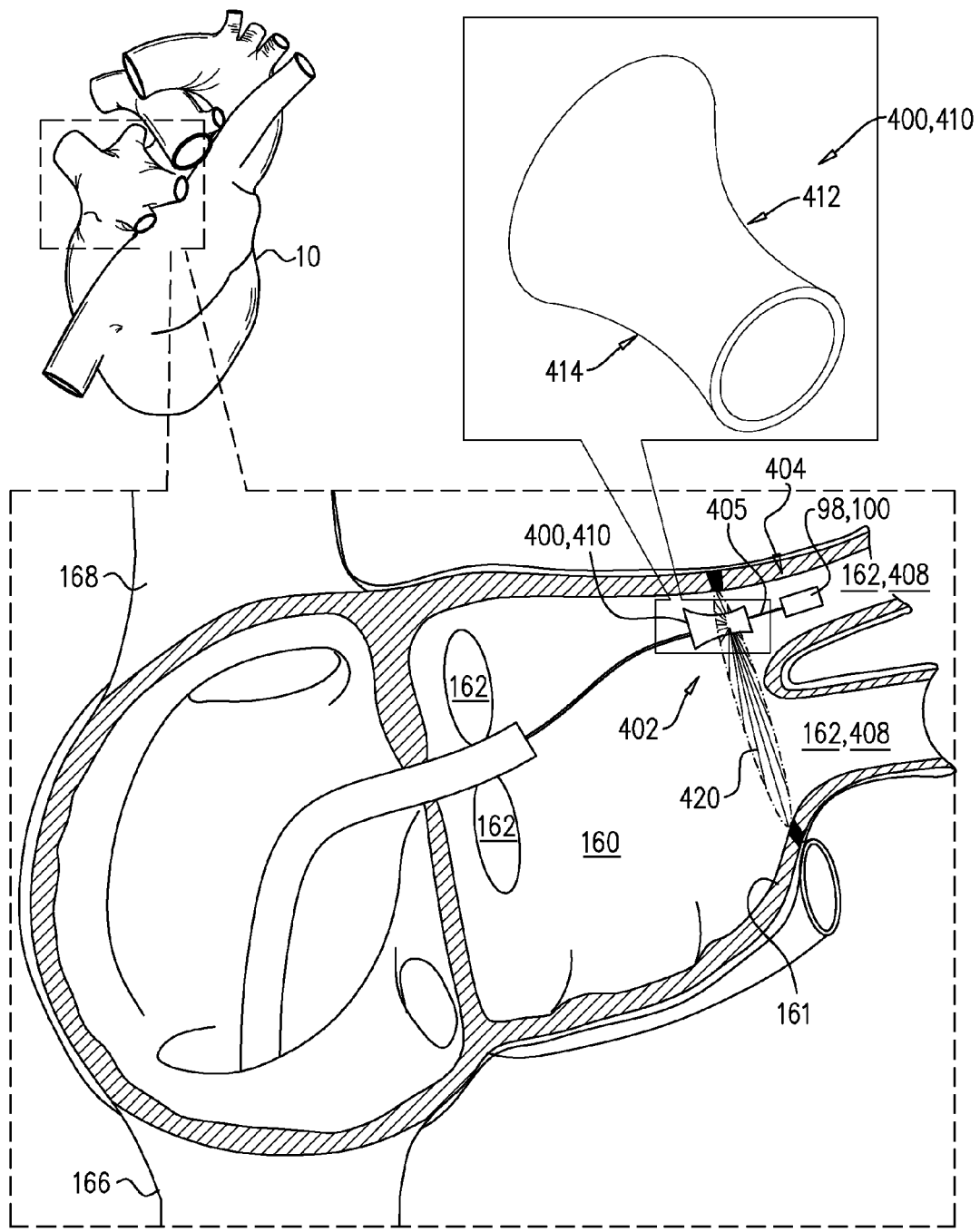
FIG. 7 is a schematic illustration of pulmonary vein isolation by generation of an annular lesion in heart tissue, using an ultrasound transducer that has a non-circular 360-degree focal pattern, in accordance with some applications of the invention.

Reference is made to FIG. 7, which is a schematic illustration of pulmonary vein isolation by generation of an annular lesion in heart tissue, using an ultrasound transducer 400 that has a non-circular 360-degree focal pattern, in accordance with some applications of the invention.

Ultrasound transducer 400 is advanced into left atrium 160 of the subject, and is positioned in a vicinity of a pulmonary vein 162, such as a first pulmonary vein 406. Typically, a tool 402, comprising transducer 400 and a guiding element 404 is advanced into atrium 160, and the transducer is positioned by placing the guiding element within the pulmonary vein. The guiding element thereby stabilizes transducer 400 in the vicinity of the pulmonary vein (e.g., the ostium thereof). For some applications, guiding element 404 comprises a guidewire 405. For some applications, guiding element 404 comprises an anchoring element, and is anchored (e.g., coupled) to the pulmonary vein. For some such applications, guiding element 404 comprises anchoring element 98 and/or inflatable element 100, and is anchored to the pulmonary vein by inflating the inflatable element (e.g., as described hereinabove with reference to FIGS. 2A-F, mutatis mutandis). For some applications, transducer 400 is slidably coupled to guiding element 404, and tool 402 is configured such that transducer 400 is advanceable along the guiding element (e.g., along guidewire 405) after the guiding element is positioned within pulmonary vein 406. Alternatively, transducer 400 may be fixedly coupled to the guiding element, and is advanced simultaneously with the guiding element.

While ultrasound transducer 400 is in the vicinity of first pulmonary vein 406, the transducer is driven to apply ultrasound energy having a non-circular 360-degree focal pattern 420. For example, the focal pattern and lesion may be generally oval (e.g., elliptical). The non-circular focal pattern of the ultrasound energy facilitates the generation of an annular lesion while the transducer is disposed at a site that is not at the center of the lesion (e.g., a site that is not equidistant from all parts of the lesion). Transducer 400 is configured and/or oriented such that the non-circular 360-degree focal pattern generates an annular lesion that circumscribes more than one pulmonary vein ostium. Typically, the lesion circumscribes the ostium of first pulmonary vein 406 and the ostium of an ipsilateral second pulmonary vein 408. For example, the lesion may be similar to ablation sites 154*a* and 154*b*, described with reference to FIG. 3B, mutatis mutandis.

Typically, transducer 400 generates the ultrasound energy from a lateral surface thereof. For some applications of the invention, transducer 400 comprises a rotationally asymmetric ultrasound transducer 410, as shown in FIG. 7. Transducer 410 is configured such that a focal length of ultrasound energy from a first portion 412 (e.g., a first side) thereof, is shorter than a focal length of ultrasound energy from a second portion 414 (e.g., a second side) thereof. Typically, transducer 410 has an asymmetric hourglass shape, and the lateral surface thereof is concave such that a concavity at first portion 412 is greater (e.g., deeper) than a concavity at second portion 414. It is to be noted that, although the configuration of transducer 410 is described with reference to first and second portions (e.g., sides), the lateral surface of the transducer is typically curved such that a concavity of progressively-changing depth circumscribes the lateral surface of the transducer, so as to generate non-circular 360-degree focal pattern 420.

For some such applications, transducer 410 comprises a piezoelectric transducer (e.g., one or more piezoelectric transducers). For some such applications, transducer 410 comprises a Capacitive Micromachined Ultrasonic Transducer (CMUT) (e.g., an array of CMUTs).

Figure 27B:
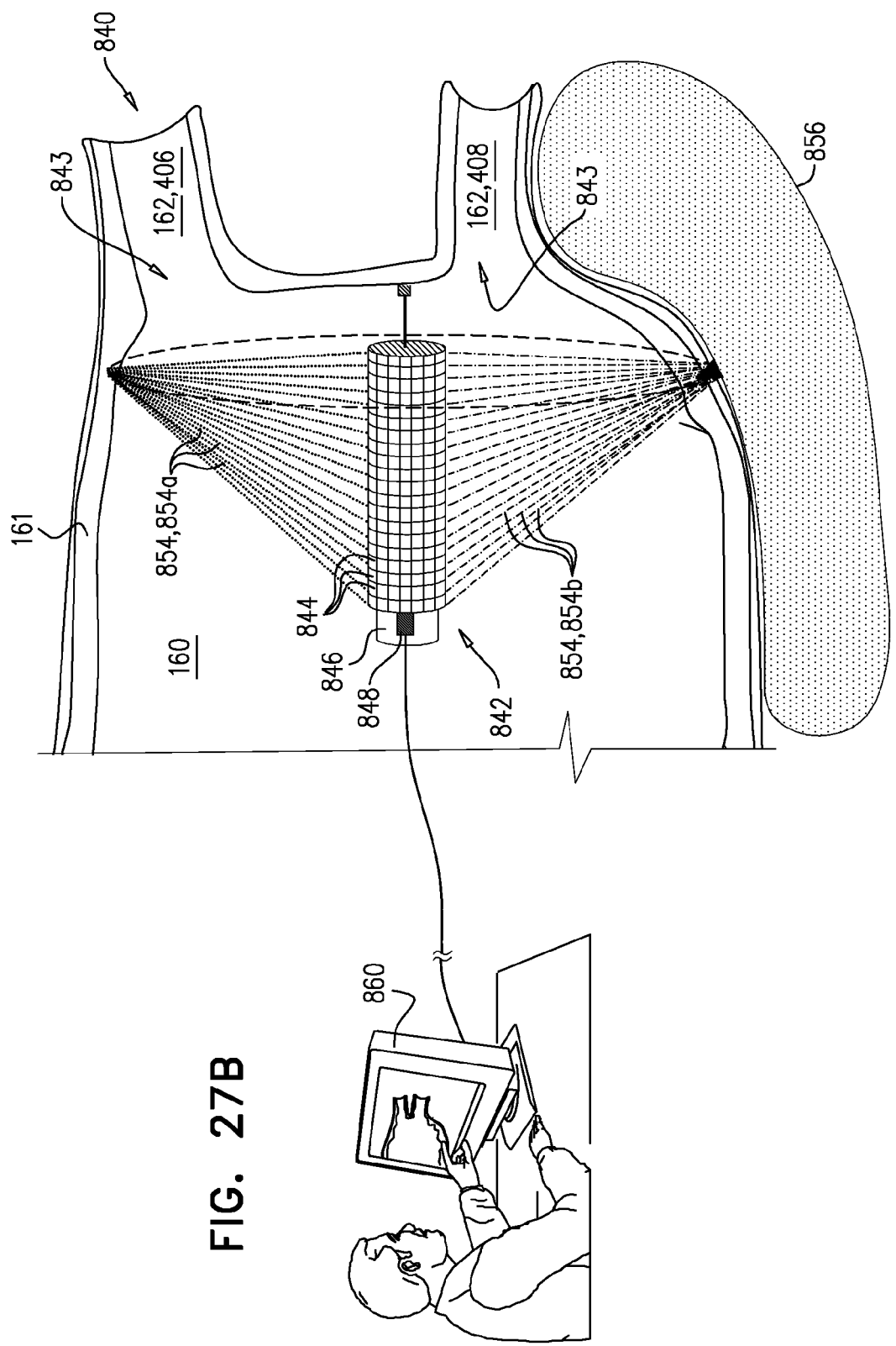

For some applications, transducer 400 and/or transducer 410 comprises a phased array of transducers (e.g., CMUTs), configured to apply the ultrasound energy in the non-circular 360-degree focal pattern. For some such applications, transducer 400 is not necessarily rotationally asymmetric. For example, transducer 400 may comprise a generally cylindrical array of CMUT (e.g., as shown in FIGS. 27A-B, mutatis mutandis), and the array of transducers is configured to generate the ultrasound energy in non-circular 360-degree focal pattern 420. Similarly, for some such applications, the transducer is not necessarily tubular. For example, transducer 400 may be generally flat (e.g., disc-shaped), and the phased array of transducers may be configured to generate the ultrasound energy in the non-circular 360-degree focal pattern.

For some applications, transducer 400 comprises a unidirectional transducer with variable focal length, and the annular lesion is generated by rotating the transducer around a longitudinal axis of tool 402 (e.g., by rotating tool 402), and varying the focal length of the transducer as appropriate.

Reference is made to FIG. 8, which is a schematic illustration of a transducer unit 440, in accordance with some applications of the invention. Transducer unit 440 comprises at least two transducers 442 and 444, and is manufactured by fixedly coupling the two transducers together (e.g., back to back). It is hypothesized that manufacturing transducer unit 440 in this way is advantageously simpler and/or cheaper than manufacturing a 360-degree transducer. For example, powder sintering may be used, rather than grinding.

For some applications, transducers 442 and 444 are configured to apply ultrasound energy simultaneously, e.g., such that transducer unit 440 acts as a single transducer that applies ultrasound energy radially in 360 degrees. For some applications, transducer unit 440 is configured to apply ultrasound energy using transducers 442 and 444 independently of each other, e.g., each applying ultrasound energy radially in 180 degrees. For some applications, transducers 442 and 444 have different focal lengths from each other, and are used to facilitate the generation of an asymmetrical lesion, such as, or similar to, the non-circular 360-degree lesion described with reference to FIG. 7. For some applications, transducer 442 is configured to apply ultrasound energy that has at least one property (e.g., amplitude and/or frequency) that is different from that applied by transducer 444. Similarly, transducer unit 440 may comprise, or be coupled to, a control unit (not shown) that drives and/or configures transducer 442 to apply ultrasound energy that has at least one property that is different from that applied by transducer 444.

For some applications, transducer unit 440 is used to generate a 360-degree lesion using both transducers and also (e.g., beforehand and/or subsequently) to generate a 180-degree lesion using one transducer. For some applications, such techniques are used to generate a "Cox Maze", as is known in the art, for treating atrial fibrillation.

It is to be noted that transducers 442 and 444 are shown as identical, purely for illustration, and that the scope of the invention includes other configurations (e.g., shapes) of the transducers and/or transducer unit 440. For example, one transducer may have a longer focal distance than the other, so as to generate a non-circular 360-degree lesion (e.g., as described hereinabove with reference to FIGS. 7A-C, mutatis mutandis). Alternatively or additionally, one transducer may be configured to apply ultrasound energy at a different frequency than the other.

Reference is made to FIGS. 9A-B, which are schematic illustrations of a transducer unit 460, comprising an ultrasound transducer 462 and a camera unit 470, in accordance with respective applications of the invention. Camera unit 470 comprises a camera 464, which is configured (e.g., positioned) to acquire images of a target site 472 at which a lesion will be, is being, and/or has been generated by transducer 462. For example, camera unit 470 may be used to facilitate intracorporeal navigation and/or positioning of the transducer unit, and/or to detect a change (e.g., an image change, such as a color change) in target site 472 that is at least in part indicative of a degree of ablation at the target site (e.g., of the target tissue). For example, camera 464 may comprise a visible color camera and/or infra-red camera.

Typically, and as shown in FIGS. 9A-B, transducer 462 is generally hourglass-shaped, and is configured to apply ultrasound energy in an annular focal pattern, disposed radially outward from midway along the longitudinal axis of the transducer (e.g., disposed radially outward from the narrowest point of the transducer along the longitudinal axis thereof).

For some applications, camera unit 470 is configured to control, or to facilitate control of, transducer 462 (e.g., to act as a control unit of unit 460). For example, in response to detecting a degree of ablation (e.g., a desired degree of ablation) of target site 472, camera unit 470 may be configured to reduce the amplitude of ultrasound energy applied by transducer 462 (e.g., to stop the transducer from applying ultrasound energy).

FIG. 9A shows transducer unit 460 comprising a transducer unit 460a, and camera unit 470 comprising a camera unit 470a. The focal point of transducer 462 (e.g., at least part of the focal pattern of the transducer) is located at target site 472, generally radially outward from midway along a longitudinal axis of the transducer. Camera unit 470a is disposed generally midway along a longitudinal axis of transducer 462, such that camera 464 faces laterally outward from the transducer. Thereby, camera 464 is disposed generally opposite target site 472, and faces the target site.

FIG. 9B shows transducer unit 460 comprising a transducer unit 460b, and camera unit 470 comprising a camera unit 470b. The focal point of transducer 462 is located at target site 472, disposed generally radially outward from midway along a longitudinal axis of the transducer. Camera unit 470b is disposed at one end of transducer 462 and camera 464 is angled to face target site 472. It is to be noted that the scope of the present invention includes any suitable position of camera unit 470.

For some applications, camera unit 470 comprises (e.g., camera units 470a and 470b comprise) a movable mount 466 on which camera 464 is mounted, such that the camera is movable, e.g., so as to facilitate acquisition of images of more than one portion of the target site. For example, and as shown in FIGS. 9A-B, movable mount 466 may comprise a rotatable mount, such as a rotatable ring, configured to facilitate revolving of camera 464 around the longitudinal axis of transducer 462.

For some applications, and as shown in FIG. 9A, camera unit 470 comprises a transparent element 468, configured to facilitate acquisition of images by camera 464. Transparent element 468 provides a window through which camera unit 470 may acquire the images. Typically, transparent element 468 is configured to exclude a body fluid (e.g., blood), so as to provide a space within the body fluid (e.g., an area between camera 464 and focal point (i.e., target site) 472), and thereby to provide a clear line-of-sight for camera 464. For some applications, transparent element 468 is reversibly expandable (e.g., reversibly inflatable), so as to reversibly increase the size of the space within the body fluid, such as by expanding until the transparent element makes contact with target site 472.

It is to be noted that camera unit 470 is shown as a component of transducer unit 460 purely for example, and that the camera unit may be used in combination with other transducers and/or transducer units described herein.

Figure 10C:
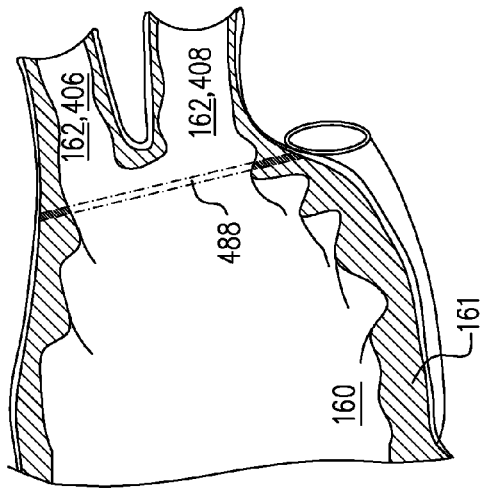
FIGS. 10A-C are schematic illustrations of a system for ablating tissue, in accordance with some applications of the invention.
Figure 10B:
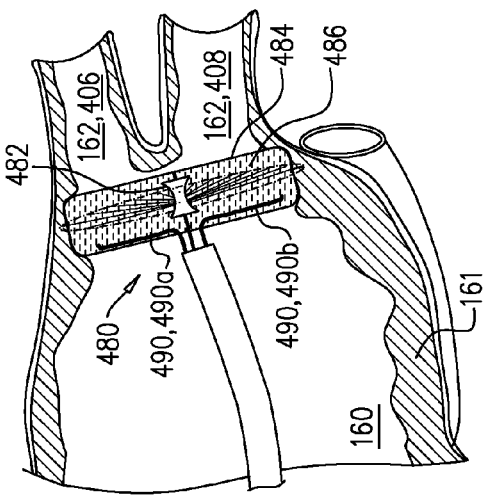
Figure 10A:
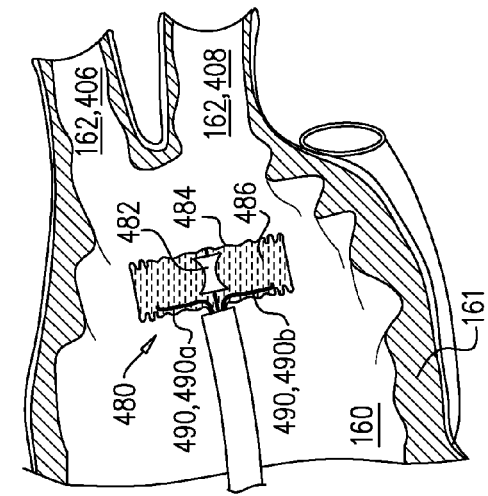

Reference is made to FIGS. 10A-C, which are schematic illustrations of a system 480 for ablating tissue, in accordance with some applications of the invention. System 480 comprises an inflatable element 484 and an ultrasound transducer 482, disposed within the inflatable element. Inflatable element 484 is inflated with a liquid 486 that facilitates transmission of ultrasound energy therethrough, and thereby facilitates the generation of a lesion 488. Typically, liquid 486 has an acoustic impedance that is similar to that of the tissue that is to be ablated, and is further typically acoustically transparent. Thereby, inflatable element 484, when inflated, is configured to conduct ultrasound energy from transducer 482 to the tissue.

System 480 is delivered (e.g., percutaneously) into left atrium 160 of the subject, and inflatable element 184 is inflated with liquid 486, such that the inflatable element contacts wall 161 of the atrium (FIGS. 10A-B). Typically, inflatable element 484 is dimensioned such that, when inflated, the inflatable element fits snugly within left atrium 160, and/or within a specific part of the atrium. Inflatable element 484 thereby typically facilitates positioning of system 480 (and thereby of transducer 482) within atrium 160 by anchoring the transducer at a given site within the atrium. Transducer 482 subsequently applies ultrasound energy, via liquid 486, to wall 161 (FIG. 10B).

For some applications, transducer 482 is configured to have a circular focal pattern, and thereby to generate a circular ablation pattern. For some such applications, inflatable element 484 has a generally circular cross-section, and is configured, when inflated, to press against wall 161 of the atrium, and to temporarily (e.g., reversibly) reshape the wall to have a generally circular cross-section (e.g., a more circular cross-section), so as to "match" the focal pattern of the transducer (i.e., so as to become more similar in size and/or shape to the focal pattern) (FIG. 10B). This thereby facilitates the generation of a 360-degree lesion in a normally non-circular tissue, using a transducer with a circular focal pattern (FIG. 10C). It is to be noted that, although transducer 482 is shown as a rotationally-symmetrical hourglass-shaped ultrasound transducer, transducer 482 may alternatively comprise another transducer (e.g., another transducer described herein), mutatis mutandis.

System 480 comprises at least one inflation tube 490, in fluid communication with inflatable element 484, for inflating the inflatable element. For some applications, inflatable element comprises two or more inflation tubes 490 (e.g., inflation tubes 490a and 490b), so as to facilitate circulation of liquid 486, e.g., to cool transducer 482 and/or wall 161. For example, one inflation tube (e.g., inflation tube 490a) may be used to introduce relatively cool liquid 486 into inflatable element 484, and the other inflation tube (e.g., inflation tube 490b) may be used to remove relatively warm liquid 486 from the inflatable element. For such applications, liquid 486 is typically acoustically and/or optically transparent.

For some applications of the invention, system 480 further comprises a camera, coupled to transducer 482, and configured (e.g., positioned) to acquire images of the target site at which a lesion will be, is being, and/or has been generated by the transducer (e.g., as described for camera 464 with reference to FIGS. 9A-B, mutatis mutandis). For some such applications, the camera is disposed within inflatable element 484, and the inflatable element facilitates acquisition of images by the camera unit, such as by excluding a body fluid (e.g., blood), so as to provide a clear line-of-sight for the camera. For example, inflatable element 484 may act as, or comprise, transparent element 468, described with reference to FIG. 9A.

System 480 may be used in combination with one or more of the reflection-facilitation elements described herein, so as to increase efficacy and/or safety of the ultrasound-based ablation.

Figure 11:
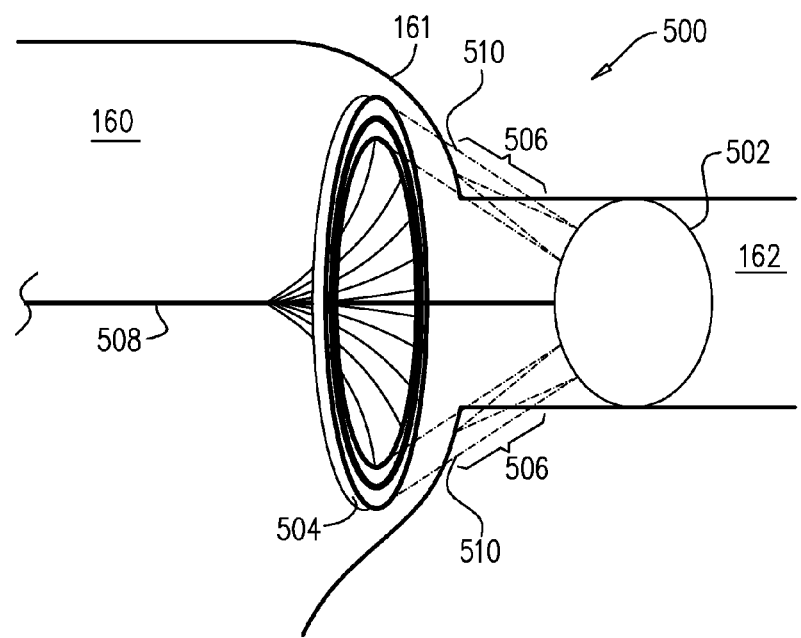
FIG. 11 is a schematic illustration of a system for ablating tissue circumscribing an ostium of a pulmonary vein of a subject, in accordance with some applications of the invention.
Figure 12:
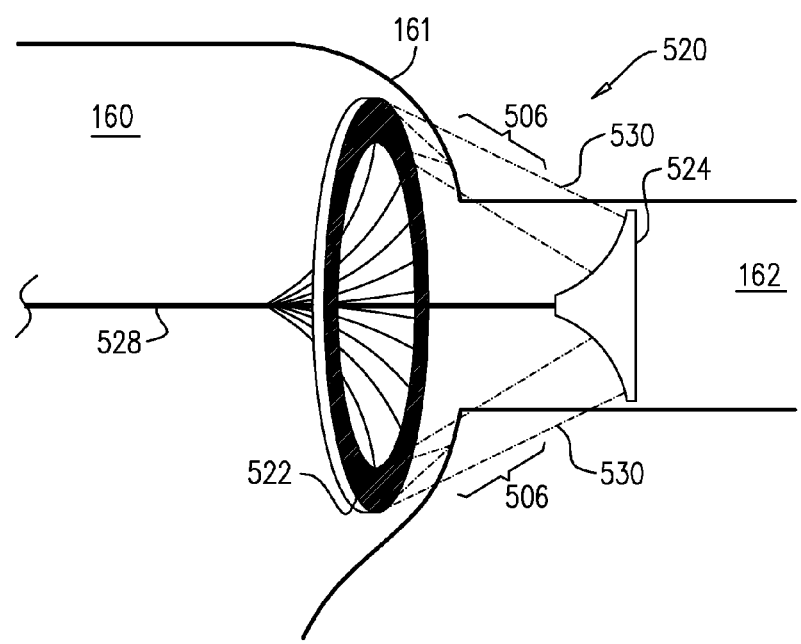
FIG. 12 is a schematic illustration of a system for ablating tissue circumscribing an ostium of a pulmonary vein of a subject, in accordance with some applications of the invention.

Reference is made to FIGS. 11-12, which are schematic illustrations of systems 500 and 520, respectively, for ablating tissue circumscribing an ostium of a pulmonary vein 162 of a subject, in accordance with some applications of the invention. Systems 500 and 520 each comprise an ultrasound transducer and a reflection-facilitation element, configured to be placed on either side of the ostium. Systems 500 and 520 are configured to form an annular lesion that circumscribes the ostium, by the transducer applying ultrasound energy to cardiac tissue at the ostium, at least part of that energy traversing the tissue and reaching the reflection-facilitation element, and the reflection-facilitation element reflecting at least part of that energy back through the cardiac tissue. This reflection typically increases efficacy and/or safety of the ultrasound-based ablation.

Reference is made to FIG. 11, which is a schematic illustration of a system 500, for ablating tissue of a subject, in accordance with some applications of the invention. System 500 comprises an inflatable reflection-facilitation element 502, and an annular ultrasound transducer 504. Typically, system 500 further comprises a control tube 508, which couples the reflection-facilitation element to the transducer, and facilitates positioning of the system, control of transducer 504, and/or inflation of element 502. For example, control tube 508 may define a lumen therethrough, in which are disposed an inflation tube and/or one or more wires.

Reflection-facilitation element 502 is configured to be placed within a pulmonary vein 162 of the subject, in a vicinity of an ostia thereof, and to be inflated with an inflation fluid (e.g., a gas), as shown in FIG. 11. As also shown in FIG. 11, system 500 is configured such that, when element 502 is thus positioned, transducer 504 is disposed within left atrium 160, in a vicinity of the ostium of the pulmonary vein. That is, ultrasound transducer 504 is coupled to reflection-facilitation element 502 such that positioning of the reflection-facilitation element within the vasculature of the subject and on a first side of the ostium of the pulmonary vein (i.e., within the pulmonary vein), positions the ultrasound transducer within the vasculature of the subject and on a second side of the ostium of the pulmonary vein (i.e., within the atrium).

Typically, inflation of element 502 secures system 500 in place by anchoring to the pulmonary vein. Thereby, element 502, when inflated on the first side of the ostium, is dimensioned to facilitates positioning of transducer 504 at the second side of the ostium. For some applications, element 502 is shaped to define a lumen therethrough, such that blood may continue to flow into the pulmonary vein during the time that element 502 is inflated.

When reflection-facilitation element 502 is disposed within pulmonary vein 162, and transducer 504 is disposed in atrium 160 in a vicinity of the pulmonary vein, cardiac tissue 506 (e.g., part of atrial wall 161) that circumscribes the ostium of the pulmonary vein is disposed between the transducer and the reflection-facilitation element. Transducer 504 applies ultrasound energy toward cardiac tissue 506 and element 502. At least part of the ultrasound energy 510 reaches element 502. Due to the difference in acoustic impedance between the gas and cardiac tissue 506, the gas acts as a reflective region, and ultrasound waves that reach the gas are reflected. Thus, at least part of the ultrasound energy that passes through cardiac tissue 506 is typically by element 502, back through the cardiac tissue, resulting in temperature elevation and enhanced ablation of the cardiac tissue, e.g., as described hereinabove, mutatis mutandis. For some applications, and as shown in FIG. 11, a focal point of transducer 504 is beyond cardiac tissue 506, such that, when reflected, the ultrasound waves are focused on the cardiac tissue. That is, for some applications, element 502 further facilitates the ablation by reflecting the focal point of the ultrasound waves to be within cardiac tissue 506.

Reference is made to FIG. 12, which is a schematic illustration of a system 520, for ablating tissue of a subject, in accordance with some applications of the invention. System 520 comprises an annular reflection-facilitation element 522, and an ultrasound transducer 524. Typically, transducer 524 (e.g., a transducer surface thereof) is also generally annular. Typically, system 520 further comprises a control tube 528, which couples the reflection-facilitation element to the transducer, and facilitates positioning of the system and/or control of transducer 524. For example, control tube 528 may define a lumen therethrough, in which is disposed one or more wires.

Reflection-facilitation element 522 is configured to be placed within atrium 160 of the subject, in a vicinity of the ostium of a pulmonary vein 162, as shown in FIG. 12. As also shown in FIG. 12, system 520 is configured such that, when element 522 is thus positioned, ultrasound transducer 524 is disposed within a pulmonary vein 162 of the subject, in a vicinity of the ostium thereof. That is, ultrasound transducer 524 is coupled to reflection-facilitation element 522 such that positioning of the reflection-facilitation element within the vasculature of the subject and on a first side of the ostium of the pulmonary vein (i.e., within the atrium), positions the ultrasound transducer within the vasculature of the subject and on a second side of the ostium of the pulmonary vein (i.e., within the pulmonary vein).

Reflection-facilitation element 522 may comprise any material that reflects ultrasound. For some applications, element 522 comprises an inflatable reflection-facilitation element. For some applications, reflection-facilitation element 522 comprises a metal, such as gold or stainless steel, to facilitate reflection of ultrasound energy. Furthermore, the metallic composition may facilitate positioning of element 522 at the ostium, using imaging techniques such as fluoroscopy. For some applications, element 522 comprises expanded polystyrene.

For some applications, system 520 is positioned by placing reflection-facilitation element 522 against atrial wall 161. That is, for some applications, element 522 is dimensioned and/or shaped such that placing the element against wall 161 such that the element circumscribes the ostium of pulmonary vein 162, facilitates placement of transducer 524 at a correct position (e.g., depth) within the pulmonary vein.

When reflection-facilitation element 522 is disposed in atrium 160 in a vicinity of the pulmonary vein, and transducer 524 is disposed within pulmonary vein 162, cardiac tissue 506 (e.g., part of atrial wall 161) that circumscribes the ostium of the pulmonary vein is disposed between the transducer and the reflection-facilitation element. Transducer 524 applies ultrasound energy toward cardiac tissue 506 and element 522. At least part of the ultrasound energy reaches element 522, and at least part of that energy is reflected by element 522, back through the cardiac tissue, resulting in temperature elevation and enhanced ablation of the cardiac tissue, e.g., as described hereinabove, mutatis mutandis. For some applications, and as shown in FIG. 12, a focal point of transducer 524 is beyond cardiac tissue 506, such that, when reflected, the ultrasound waves are focused on the cardiac tissue. That is, for some applications, element 522 further facilitates the ablation by reflecting the focal point of the ultrasound waves to be within cardiac tissue 506.

Reference is made to FIGS. 13-15D, which are schematic illustrations of systems for ablating a circumferential lesion in cardiac tissue, so as to electrically isolate all four pulmonary vein ostia from the left atrium, in accordance with some applications of the invention. The systems described with reference to FIGS. 13-15D each comprise a respective reflection-facilitation element, a respective ultrasound transducer, and a respective elongate member. The elongate member of each system is configured to be delivered to the pericardial cavity, and to form (or to be formed into) a loop that generally encompasses the four pulmonary vein ostia.

Typically, the elongate member is configured to be delivered to the pericardial cavity percutaneously.

Each system is configured to ablate cardiac tissue in the immediate vicinity of the elongate member, thereby creating a circumferential lesion that generally circumscribes the four pulmonary vein ostia. That is, the shape of the lesion is generally similar to the shape of the elongate member in the looped state. The shape of the lesion is typically similar to a "box lesion", as is known in the atrial fibrillation art, and is configured to electrically isolate all four pulmonary vein ostia from the left atrium (or a large portion thereof), so as to treat atrial fibrillation.

For each system, the ultrasound transducer is placed on one side of the tissue to be ablated, and the reflection-facilitation element is placed, and provides a reflective region, on the other side of the tissue. The reflective region increases the efficacy and/or safety of the ultrasound-based ablation, as described hereinabove.

For clarity, FIGS. 13-15D show each elongate member disposed within the pericardium, at the ablation site, with both ends of each elongate member detached from any other apparatus. Typically, at least one end of the elongate member is couplable to a control rod, which facilitates delivery, positioning and/or inflation of the elongate member. Elongate member may be delivered to the pericardium using any suitable technique known in the art, such as via a subxiphoid approach or an intercostal approach.

FIGS. 13-15D show each elongate member as a single, continuous elongate member. However, for some applications, each elongate member comprises two or more subunits, each subunit disposed in a respective portion of the pericardium. For example, for applications in which the desired location of the elongate member traverses a pericardial reflection, a first subunit may be disposed on one side of the reflection, and a second subunit may be disposed on the other side of the reflection. For some such applications, the subunits are reversibly magnetically couplable to each other (e.g., via one or more electromagnets) so as to, in effect, result in an elongate member that traverses the reflection.

FIG. 13 shows a system 540, comprising an elongate member 542 and a reflection-facilitation element 544. Elongate member 542 has a first end 550 and a second end 552, and a longitudinal axis therebetween. Elongate member 542 functions as an elongate ultrasound transducer, typically comprising a plurality of ultrasound transducers 546 disposed along at least part of the longitudinal axis of the elongate member. For some applications of the invention, each of the plurality of ultrasound transducers is configured to apply ultrasound in a pattern that overlaps ultrasound applied by an adjacent transducer. Thereby, for such applications, elongate member 542 applies a continuous line of ultrasound. Reflection-facilitation element 544 comprises an inflatable element (e.g., a balloon).

Elongate member 542 is placed pericardially such that the elongate member forms a loop that generally encompasses the ostia of all four pulmonary veins 162, as described hereinabove, and as shown in FIG. 13. Reflection-facilitation element 544 is placed in left atrium 160 and against the atrial wall, opposite elongate member 542 (i.e., on the other side of the heart tissue from the elongate member), and is subsequently inflated.

Elongate member 542 (e.g., transducers 546 thereof) are driven to apply ultrasound energy, at least some of which passes through the tissue of the atrial wall, and is reflected by element 544, thereby ablating tissue disposed between member 542 and element 544, e.g., as described with reference to FIGS. 11-12, mutatis mutandis. It is hypothesized that, because ablation is dependent on reflection-facilitated concentration of ultrasound energy, for some applications, elongate member 542 (e.g., ultrasound transducers 546 thereof) may be configured to apply ultrasound energy at an amplitude that is insufficient to ablate tissue in the absence of such reflection, and thereby advantageously insufficient to inadvertently ablate non-target tissues. Further, due to this configuration, for some applications, elongate member 542 is configured to apply ultrasound energy in 360 degrees laterally from the longitudinal axis thereof, such that positioning of the elongate member within the pericardium is generally independent of the rotational orientation of the elongate member around the longitudinal axis thereof.

For some applications, the apparatus and techniques described with reference to FIG. 13 may be combined with apparatus and techniques described in US 2005-0251125 to Pless, which is incorporated herein by reference. For example, for some applications, transducer 482 may comprise an ablation device described with reference to US 2005-0251125 to Pless (e.g., a flexible shaft having a plurality of transducers spaced apart a distance selected so that the lesions created by adjacent transducers contact or overlap one another, thereby creating a continuous, uninterrupted lesion in the tissue underlying the flexible shaft).

FIG. 14 shows a system 560, comprising an elongate member 562 and an ultrasound transducer unit 564. Elongate member 562 has a first end 570 and a second end 572, and a longitudinal axis therebetween. Elongate member 562 comprises and/or acts as an elongate reflection-facilitation element. For example, member 562 may be shaped to define an elongate chamber 566 therethrough, the elongate chamber (1) typically being pre-filled and/or inflatable with a gas, and (2) comprising and/or acting as an elongate reflection-facilitation element. Ultrasound transducer unit 564 comprises one or more ultrasound transducers, and is typically configured to apply ultrasound energy at a wide three-dimensional angle. For example, unit 564 may be configured to apply the ultrasound energy at a solid angle of greater than two steradians, e.g., greater than four steradians, e.g., greater than a hemisphere, such as generally in all directions.

Elongate member 562 is placed pericardially such that the elongate member forms a loop that generally encompasses the ostia of all four pulmonary veins 162, as described hereinabove, and as shown in FIG. 14. Ultrasound transducer unit 564 is placed in left atrium 160 (i.e., on the other side of the heart tissue from the elongate member), as shown in FIG. 14.

Ultrasound transducer unit 564 is driven to apply ultrasound energy, at least some of which passes through the tissue of the atrial wall, and is reflected by member 562, thereby ablating tissue disposed between unit 564 and member 562, e.g., as described with reference to FIGS. 11-12, mutatis mutandis. It is hypothesized that, because ablation is dependent on reflection-facilitated concentration of ultrasound energy, ultrasound transducer unit 564 may be configured to apply ultrasound energy at an amplitude that is insufficient to ablate tissue in the absence of such reflection, and thereby advantageously insufficient to inadvertently ablate non-target tissues. Further, due to this configuration, and due to the wide angle of ultrasound energy applied by transducer unit 564, for some applications, positioning of the transducer unit within atrium 160 is generally independent of the rotational orientation of the transducer unit.

FIGS. 15A-D shows a system 580, comprising an elongate member 582 and a reflection-facilitation element 584.

Elongate member 582 has a first end 590 and a second end 592, and a longitudinal axis therebetween. Elongate member 582 comprises an ultrasound transducer 586, slidable along the longitudinal axis of the elongate member (e.g., using a control rod 587 that extends to outside the body of the subject). Typically, elongate member 582 is shaped to define an elongate chamber 583 therethrough, and transducer 586 is slidable through at least part of the elongate chamber. Thereby, member 582 is configured to apply a continuous line of ultrasound by sliding transducer 586 along member 582. Reflection-facilitation element 584 typically comprises an inflatable element (e.g., a balloon).

Transducer 586 and element 584 are configured to be magnetically coupled to each other (e.g., reversibly magnetically coupled to each other). For example transducer 586 and/or element 584 may comprise a magnetically-attractable element such as an electromagnet and/or a metallic element.

Elongate member 582 is placed pericardially such that the elongate member forms a loop that generally encompasses the ostia of all four pulmonary veins 162, as described hereinabove, and as shown in FIGS. 15A-D. Reflection-facilitation element 584 is placed in left atrium 160 (i.e., on the other side of the heart tissue from the elongate member), and is subsequently inflated.

Figure 15A:
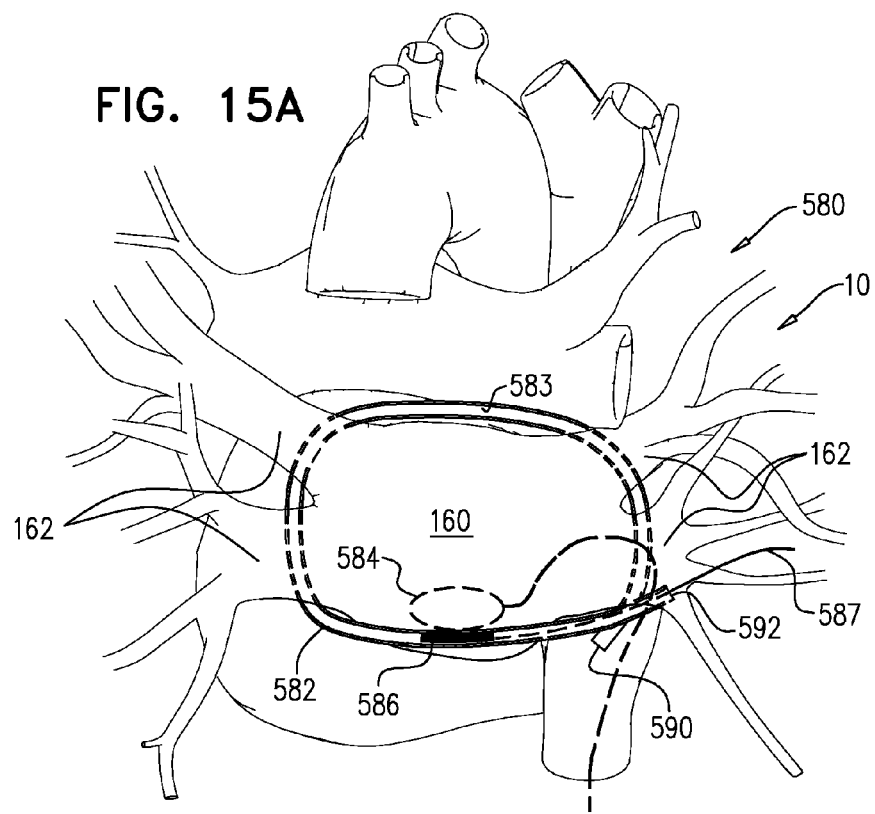
Figure 15B:
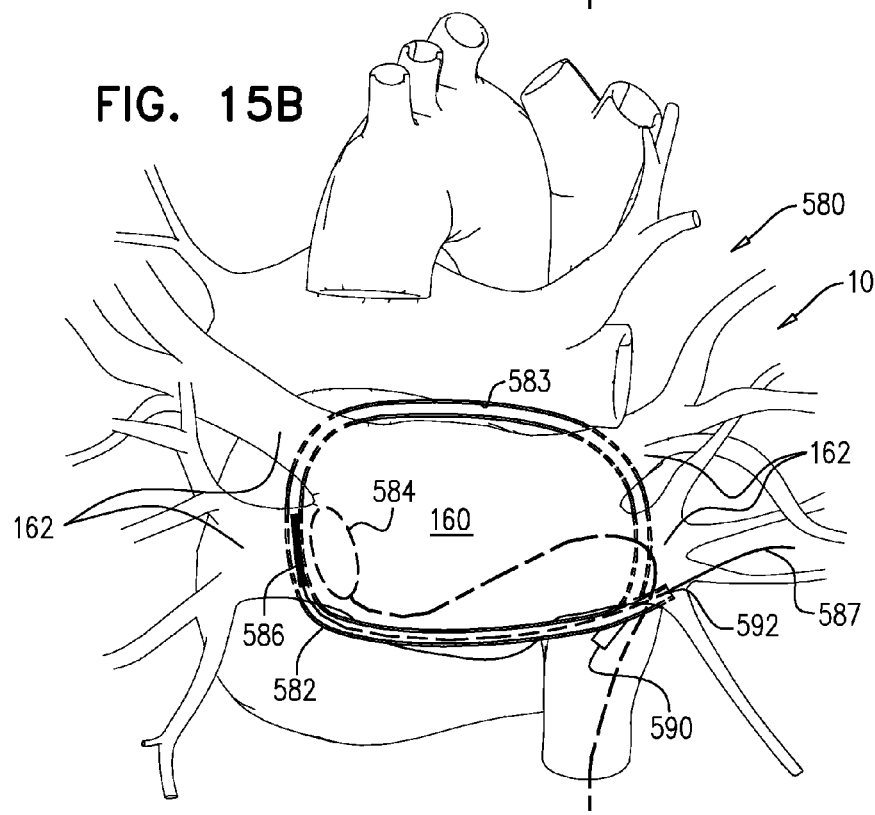

The magnetic coupling draws transducer 586 and element 584 toward each other on either side of the wall of left atrium 160 (FIG. 15A). While transducer 586 and element 584 are magnetically coupled, the transducer is driven to apply ultrasound energy, at least some of which passes through the tissue of the atrial wall, and is reflected by element 584, thereby ablating tissue disposed between member 582 and element 584, e.g., as described with reference to FIGS. 11-12, mutatis mutandis. Transducer 586 is slid along elongate member 582, so as to ablate tissue along the longitudinal axis of the elongate member (FIGS. 15B-C) For some applications, application of ultrasound energy and sliding of the transducer are performed stepwise along the length of the elongate member. For some applications, ultrasound energy is applied continuously while the transducer is simultaneously slid along the length of the elongate member.

It is to be noted that the scope of the invention includes the transducer and the reflection-facilitation element in reverse positions. That is, for some applications of the invention, elongate member 582 comprises the reflection-facilitation element, and the transducer is configured to be disposed in atrium 160.

It is hypothesized that, because ablation is dependent on reflection-facilitated concentration of ultrasound energy, for some applications, ultrasound transducer 586 may be configured to apply ultrasound energy at an amplitude that is insufficient to ablate tissue in the absence of such reflection, and thereby advantageously insufficient to inadvertently ablate non-target tissues. Further, due to this configuration, for some applications, transducer 586 is configured to apply ultrasound energy in 360 degrees laterally from the longitudinal axis of longitudinal member 582, such that positioning of the elongate member within the pericardium is generally independent of the rotational orientation of the elongate member around the longitudinal axis thereof.

Figure 16A:
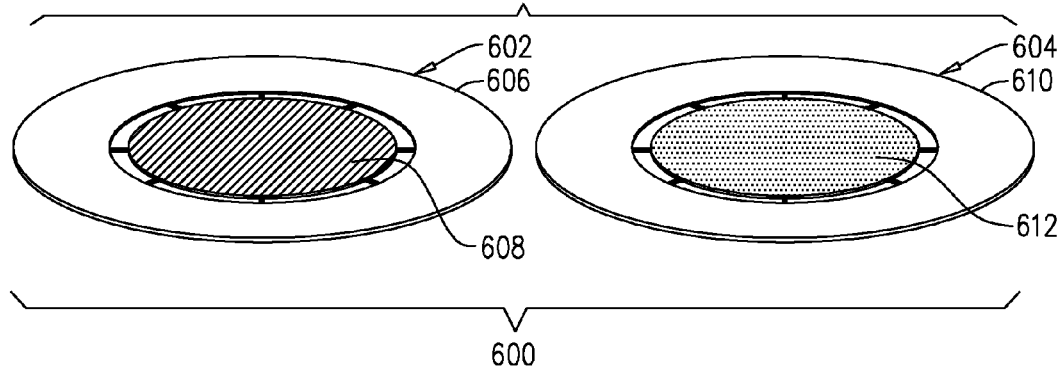
FIGS. 16A-B are schematic illustrations of a tissue ablation system, comprising a reflection-facilitation element and an ultrasound transducer unit that is magnetically couplable to the reflection-facilitation element, in accordance with some applications of the invention.
Figure 16B:
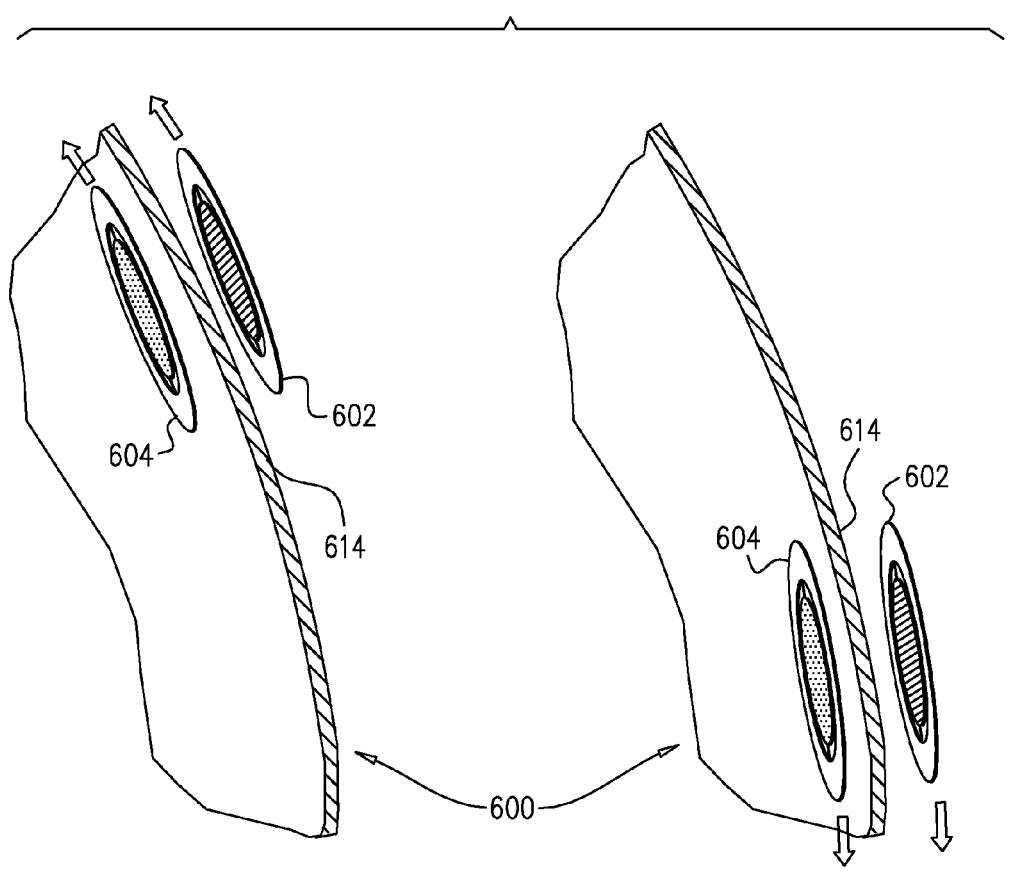

Reference is made to FIGS. 16A-B, which are schematic illustrations of a tissue ablation system 600, comprising a reflection-facilitation element 602 and an ultrasound transducer unit 604 that is magnetically couplable to the reflection-facilitation element, in accordance with some applications of the invention. Reflection-facilitation element 602 comprises a magnetically-attractable element 606, shaped to defined an opening therethrough, and a reflector 608, disposed in the opening. Reflection-facilitation element 602 (e.g., reflector 608 thereof) provides a reflective region for ultrasound. For example, element 606 may be a toroid (e.g., annular; as shown in FIGS. 16A-B) or a toroidal polyhedron (e.g., a hollow square). Transducer unit 604 comprises a magnetically-attractable element 610, shaped to defined an opening therethrough, and an ultrasound transducer 612, disposed in the opening, and configured to apply ultrasound energy. For example, element 610 may be a toroid (e.g., annular; as shown in FIGS. 16A-B) or a toroidal polyhedron. The magnetically-attractable elements are configured to be magnetically-coupled to each other (e.g., reversibly magnetically-coupled to each other), such that reflector 608 is held opposite transducer 612 and thereby in the sound field of the ultrasound energy applied by the transducer.

Typically, at least one of the magnetically-attractable elements comprises a magnet (e.g., an electromagnet). For some applications, both magnetically-attractable elements comprise magnets (e.g., electromagnets). For some applications, one of the magnetically-attractable elements comprises a metallic element that is not itself magnetic, but is magnetically-attractable by the other magnetically-attractable element. Because transducer 612 is typically wiredly coupled to the outside of the subject, for some applications, it is advantageous that transducer unit 604 comprise the electromagnet, FIG. 16B shows reflection-facilitation element 602 and transducer unit 604, magnetically coupled to each other on either side of a tissue 614 of the subject, such that movement of element 602 moves unit 604 and vice versa. For some applications, tissue 614 comprises cardiac tissue, such as atrial wall 161 (described hereinabove). For some applications, system 600 is used to ablate cardiac tissue in the vicinity of pulmonary vein ostia so as to treat atrial fibrillation. The reflective region provided by the reflection-facilitation element typically increases efficacy and/or safety of the ultrasound-based ablation, as described hereinabove.

For some applications, the techniques described with reference to FIGS. 16A-B may be combined with those described with reference to FIG. 15. For example, transducer 586 (FIG. 15) may comprise transducer 612 of transducer unit 604 (FIGS. 16A-B), and reflection-facilitation element 584 (FIG. 15) may comprise reflection-facilitation element 602 (FIGS. 16A-B).

Reference is made to FIG. 17A-B, which are schematic illustrations of intravascular inflatable reflection-facilitation elements 620 and 630, respectively, in accordance with some applications of the invention. FIG. 17A shows intravascular inflatable reflection-facilitation element 620, shaped to define a longitudinal lumen 622 therethrough. Element 620 is (1) generally tubular, (2) configured to be transluminally delivered to, and disposed within, SVC 168, and (3) in an inflated state thereof, configured to fit snugly within the SVC and to maintain fluid communication between SVC 168 and right atrium 164 via lumen 622. FIG. 17B shows intravascular inflatable reflection-facilitation element 630, shaped to define a longitudinal lumen 632 therethrough, and a lateral opening 634 that extends laterally out of lumen 632, and that provides fluid communication between lumen 632 and a lateral side of element 630. Element 630 is (1) generally tubular, (2) configured to be transluminally delivered to, and disposed within SVC 168 and IVC 166, and (3) in an inflated state thereof, configured to fit snugly within the SVC and IVC, and to maintain fluid communication between SVC 168, IVC 166, and right atrium 164 via lumen 632 and lateral opening 634.

Elements 620 and 630 are typically configured, when inflated, provide respective reflective regions for ultrasound energy, and to thereby increases efficacy and/or safety of the ultrasound-based ablation, as described hereinabove. Elements 620 and 630 may be used in combination with other reflection-facilitation elements described herein.

Reference is now made to FIG. 18, which is a schematic illustration of an anterior view of pericardium 640 (e.g., the fibrous and/or parietal pericardium) that surrounds the heart of the subject, showing placement sites 642 and 644 for inflatable reflection-facilitation elements, in accordance with some applications of the invention. It is typically desirable to provide the reflective region adjacent to as much as possible of the tissue to be ablated, so as to increase, as much as possible, the efficacy and safety of ultrasound-based ablation. For ablation of left atrial tissue of a supine subject, it is further typically desirable to increase the distance between the atrium 160 and tissue posterior to the atrium (e.g., the esophagus).

Placement site 642 (marked with an X) is within oblique sinus 646 of the pericardial cavity, between pulmonary veins 162 (e.g., ostia thereof), and inferior to sinus reflections 170. Placement site 644 (marked with an X) is within transverse sinus 648 of the pericardial cavity, superior to sinus reflections 170. It is hypothesized that placement of one or more inflatable reflection-facilitation elements at the placement sites at least in part provides the reflective region and distancing described in the previous paragraph.

Figure 19A:
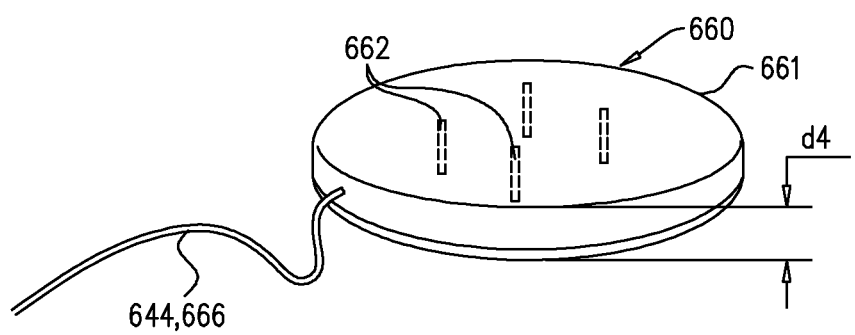
FIGS. 19A-B are schematic illustrations of inflatable reflection-facilitation elements, in accordance with some applications of the invention.
Figure 19B:
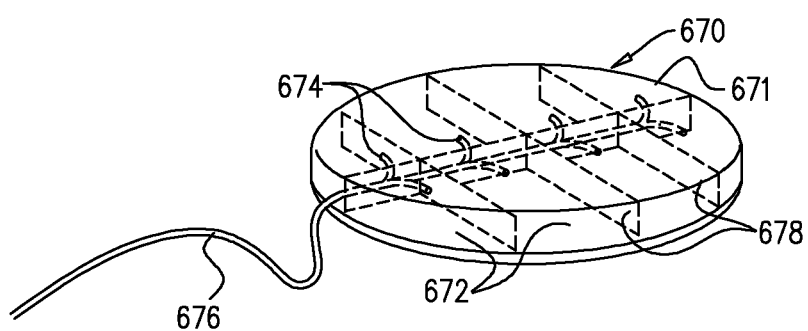

Reference is made to FIGS. 19A-B, which are schematic illustrations of inflatable reflection-facilitation elements 660 and 670, respectively, in accordance with some applications of the invention. Elements 660 and 670 comprise inflatable portions 661 and 671, respectively, each inflatable portion typically having a generally round (e.g., circular or oval) shape. Alternatively, portions 661 and/or 671 may have other shapes (e.g., shapes described with reference to FIGS. 5A-I, mutatis mutandis). Typically, when inflated and not externally constrained (e.g., if inflated while sitting on a table), inflatable portions 661 and 671 have a flattened shape (i.e., having a thickness d4 that is smaller than a length or a width of the inflatable portion), such as described for inflatable element 22 with reference to FIGS. 1A-C, mutatis mutandis. Similarly, inflatable element 22 may comprise restricting elements, as described with reference to FIGS. 19A-B, mutatis mutandis).

Element 660 (FIG. 19A) comprises an inflation tube 664 that is typically disposed within and/or integral with a steerable catheter 666. Inflatable portion 661 comprises one or more restricting elements 662, configured to limit a maximum thickness of portion 661, such as to prevent portion 661 from becoming generally spherical when inflated.

Inflatable portion 671 (FIG. 19B) defines a plurality of independently-inflatable compartments 672. Element 670 comprises a plurality of inflation tubes 674, each inflation tube extending through a steerable catheter 676, and into a respective compartment 672. Element 670 is configured such that a physician may inflate each compartment according to a specific application and/or position of the element. For some applications, dividers 678 separate compartments 672. For some such applications, dividers 678 act as restricting elements 662, described with reference to FIG. 19A.

Typically, inflatable reflection-facilitation elements 660 and 670 (e.g., inflatable portions thereof) are each configured to be disposed at placement site 642 (FIG. 18), and to provide a reflective region at the oblique sinus and/or increase the distance between the left atrium and tissues posterior thereto. The reflective region provided by each reflection-facilitation element typically increases efficacy and/or safety of the ultrasound-based ablation, as described hereinabove.

For some applications, elements 660 and 670 comprise an ablation element (e.g., an ultrasound, RF or cryogenic element; not shown), disposed on one side of the inflatable portion. For such applications, the reflection-facilitation elements are configured to be used as integrally-insulated ablation tools in which the gas used to inflate the inflatable portion insulates and/or distances tissues on one side of the inflatable portion from the ablation element on the other side of the inflatable portion.

Figure 20:
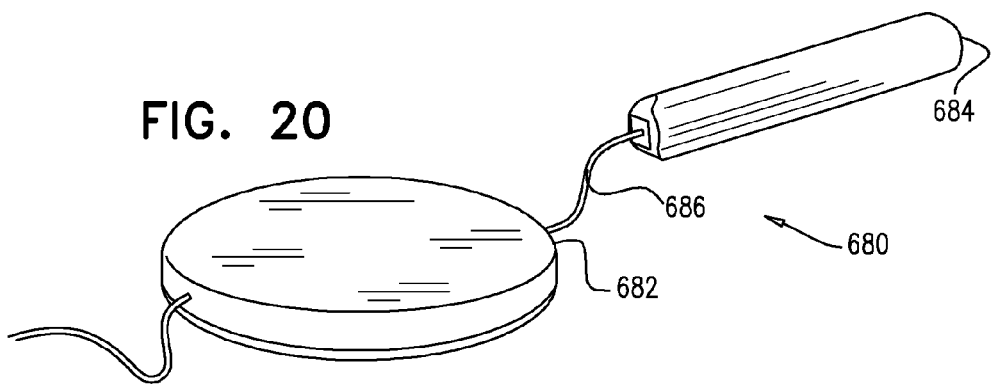
FIG. 20 is a schematic illustration of an inflatable reflection-facilitation element, comprising two inflatable members, in accordance with some applications of the invention.

Reference is made to FIG. 20, which is a schematic illustration of inflatable reflection-facilitation element 680, in accordance with some applications of the invention. Element 680 comprises two inflatable members 682 and 684, connected by a longitudinal element 686. Typically, inflatable member 682 is generally similar in shape to inflatable reflection-facilitation element 660, described with reference to FIG. 19A, and is configured to be disposed at placement site 642 (FIG. 18), and to provide a first reflective region there.

Typically, inflatable member 682 is elongate (e.g., sausage-shaped), and is configured to be disposed at placement site 644 (FIG. 18), and to provide a second reflective region there. The reflective regions provided by the reflection-facilitation element typically increases efficacy and/or safety of the ultrasound-based ablation, as described hereinabove.

For some applications, element 680 is configured to be delivered within a steerable catheter (not shown), and each inflatable member is deployed from the catheter at its respective placement site. For such applications, longitudinal element 686 typically comprises at least part of an inflation tube. Alternatively or additionally, longitudinal element 686 may itself be steerable.

Figure 21A:
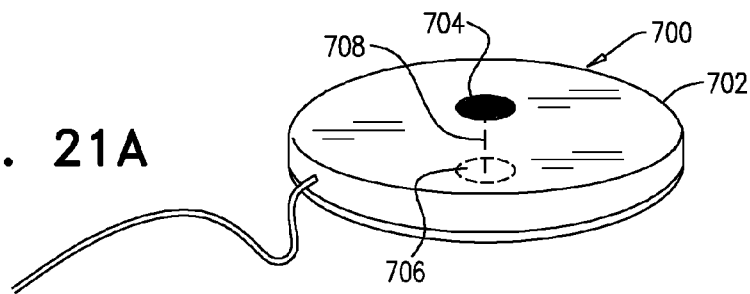
FIGS. 21A-C are schematic illustrations of inflatable reflection-facilitation elements comprising electrodes, in accordance with some applications of the invention.
Figure 21B:
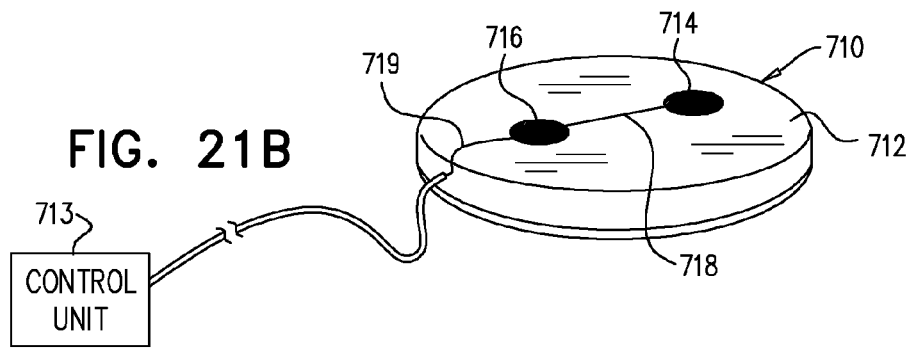

Reference is made to FIGS. 21A-B, which are schematic illustrations of inflatable reflection-facilitation elements comprising electrodes, in accordance with some applications of the invention. During cardiac procedures, such as ablation of heart tissue and inflation of the pericardium, it is occasionally necessary to defibrillate the heart of the subject. The inflatable reflection-facilitation elements described with reference to FIGS. 21A-B are configured to increase efficacy and/or safety of ultrasound-based ablation, as described throughout this patent application, and to facilitate defibrillation during such ablation procedures.

FIG. 21A shows an inflatable reflection-facilitation element 700, comprising an inflatable member 702, a first electrode 704 disposed on a first side of the inflatable member, and a second electrode 706 disposed on a second (e.g., opposite) side of the inflatable member, and electrically coupled to the first electrode (e.g., by a wire 708). As well as being configured to provide a reflective region, element 700 is further configured to facilitate defibrillation of the heart (e.g., using "paddle" electrodes), by conducting electricity (e.g., the defibrillating current) through inflatable member 702 (i.e., from the first side to the second side of the inflatable member) via electrodes 704 and 706.

FIG. 21B shows an inflatable reflection-facilitation element 710, comprising an inflatable member 712, a first electrode 714 disposed on one side of the inflatable member, and a second electrode 716 disposed on the same side of the inflatable member. Electrodes 714 and 716 are typically electrically coupled to a control unit 713, e.g., disposed outside the subject, the control unit being configured to drive the electrodes to apply a defibrillating current to the heart of the subject. Typically, electrodes 714 and 716 are independently electrically coupled to control unit 713 (e.g., via a cable 719). (For some applications, electrode 714 is electrically coupled by a wire 718 to the control unit and/or to electrode 716.) As well as being configured to provide a reflective region, element 700 is configured to facilitate defibrillation of the heart by intracorporeally applying a current to the heart via electrodes 714 and 716.

For some applications, elements 700 and 710 are further configured to facilitate navigation thereof toward the placement sites thereof. For example, the electrodes of the elements are typically radiopaque, and may facilitate navigation using imaging techniques such as fluoroscopy. Alternatively or additionally, the electrodes may be electrically coupled to an extracorporeal monitor (e.g., control unit 713 may comprise or serve as an extracorporeal monitor), and facilitate navigation by detecting electrical signals of the heart (e.g., ECG signals). It is to be noted that such navigation techniques may be combined with any of the other reflection-facilitation elements described herein. For example, other reflection-facilitation elements may comprise electrodes that facilitate navigation by detecting electrical signals of the heart.

Figure 21C:
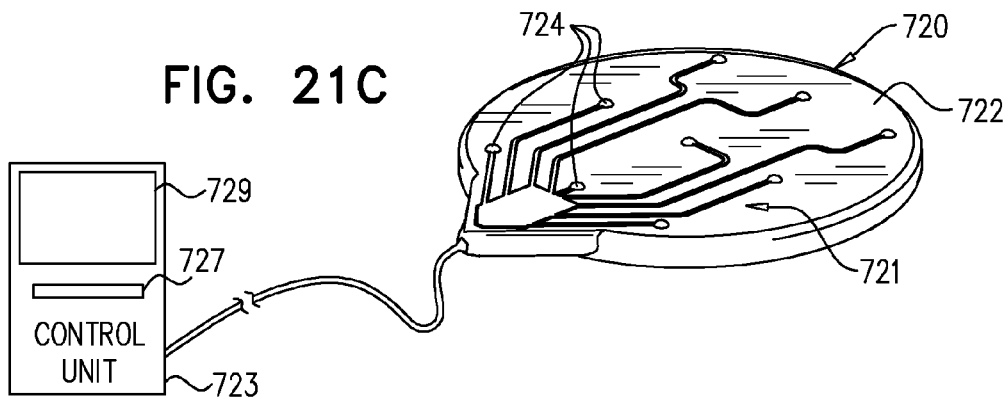

Reference is now made to FIG. 21C, which is a schematic illustration of an inflatable reflection-facilitating element 720, comprising an inflatable member 722 and an electrode array 721 comprising a plurality of electrodes 724 disposed on the inflatable member, in accordance with some applications of the invention. As described with reference to FIGS. 21A-B, for some applications, electrodes disposed on an inflatable member of a reflection-facilitation element may be used to facilitate navigation of the reflection-facilitation element by detecting electrical signals of the heart. Array 721 facilitates such navigation, as described above, mutatis mutandis. For some applications, the relatively large number of electrodes 724 in array 721 provide higher resolution navigation than the two electrodes of elements 700 and 710. For some applications, and as shown in FIG. 21C, array 721 is generally two-dimensional (i.e., electrodes 724 are disposed generally in two dimensions on a plane defined by a surface of element 720). For some applications, electrodes 724 are about 1 mm in diameter and are disposed about 2 mm from adjacent electrodes. For some applications, array 721 comprises at least 16 electrodes. For some applications, array 721 comprises at least 16 electrodes and/or less than 64 electrodes, e.g., at least 16 electrodes and/or less than 32 electrodes, e.g., 16-32 electrodes.

For some applications, when inflated, member 722 has the general appearance of a disc. For some applications, when inflated, member 722 has a thickness that is less than 20 mm (e.g., less than 10 mm, such as less than 5 mm). For some applications, when inflated, member 722 has a width (e.g., a diameter), orthogonal to the thickness, that is greater than 20 mm and/or less than 100 mm, such as between 20 and 100 mm, e.g., between 20 and 60 mm, such as between 40 and 60 mm. For some applications, when inflated, the thickness of member 722 is less than 20% (e.g., less than 10%, such as less than 5%) of its width.

Each electrode 724 is placeable in independent communication with an extracorporeal control unit 723, e.g., directly or via a multiplexer. Control unit 723 comprises a monitor 727, configured to receive signals from the electrodes, and to responsively provide information relating to the position and/or orientation of element 720 with respect to the anatomy of the subject, e.g., via a display 729. For some applications, monitor 727 displays one or more ECG readings (e.g., in the form of ECG graphs). For some applications, monitor 727 displays a graphical representation of the position and/or orientation of element 720 with respect to the anatomy of the subject.

For some applications, the signals received by monitor 727 are physiological electrical signals (e.g., ECG signals), and the position and/or orientation of element 720 with respect to the anatomy is determined by identifying signals from one or more of the electrodes that are indicative of a particular anatomical position. For example, the timing and/or magnitude of a signal (e.g., a feature of an electrocardiogram) at an electrode may be used to derive the anatomical position of the electrode, e.g., using reference timings and/or magnitudes. Similarly, differences in the timing and/or magnitude of such signals between different electrodes may be used to derive the anatomical position of each electrode, and thereby the orientation of element 720. For some applications, the signals received by monitor 727 are artificially provided by another electrode. For example, a signal (i.e., a current) applied by one of the electrodes of array 721 may be detected by one or more other electrodes of the array, and timing and/or magnitude of the signal (e.g., due to impedance) may be used to derive anatomical position and/or orientation. Alternatively or additionally the signal may be applied and/or detected by an electrode that is not part of array 721 (e.g., a reference electrode, such as an electrode elsewhere on inflatable member 722, or an extracorporeal electrode).

For some applications, the reference timings and/or magnitudes used to facilitate derivation of the anatomical position of an electrode are the same for more than one subject (e.g., are the same for all subjects, or for a subset of subjects). Alternatively or additionally, mapping of the subject to be treated is performed so as to provide reference timings for that particular subject. For some applications, element 720 is used to facilitate mapping of the anatomy of the subject. For example, the physiological and/or artificial signals described above with regard to navigation may be used to facilitate mapping, e.g., by moving element 720 around one or more regions of the pericardial cavity so as to obtain relatively large numbers of readings that may be used as reference signals for facilitating navigation. For some applications, the reference signals are used to build a virtual map, which may be displayed on display 729.

For some applications, mapping of the subject comprises mapping of the target tissue (e.g., identifying the target tissue and/or locating the target tissue with respect to other anatomical sites, e.g., by placing the target tissue on the virtual map). For example, the target tissue may be identified due to an electrical abnormality at the target tissue (e.g., electrical interference, such as interference that causes the pathology being treated). For some applications in which the target tissue is identified due to the interference that causes the pathology being treated, the progress and/or success of the treating ablation may be monitored based on a reduction in the observed interference.

For some applications, a sudden spatial change in impedance (i.e., a large difference in impedance between two close sites) is indicative of a lesion.

For some applications, in accordance with mapping techniques described hereinabove, element 720 is used to facilitate mapping of the target tissue, e.g., the pericardium, based on a desired parameter or feature. For example, information derived from sensed electrical activity signals may be used to construct a virtual two-dimensional map of the target tissue, which is displayed to the physician. Electrical signals indicating (a) time delay and/or (b) signal amplitude and/or (c) changes in electrode impedance between electrodes and/or impedance between one or more electrodes and an electrode at a common reference site, are used to map the tissue and to locate lesions and scarred tissue.

For some applications, additional information is derived from analyzing the virtual map e.g., determining the direction of signal propagation (e.g., left to right, or diagonally along the map).

For some applications, in addition to sensing electrical activity by element 720 which is placed in the pericardium, electrical activity is also detected by electrodes that are located inside the heart, for example on a catheter carrying an ablation transducer (e.g., a transducer described herein, such as transducers 92 or 524). For such applications, mapping and identifying the location of cardiac abnormalities by element 720 is further verified by corresponding electrical signals that are sensed by the electrodes inside the heart. Typically, the electrodes on the catheter carrying the ablation transducer are radiopaque (or another element on the catheter is radiopaque), and may facilitate proper positioning of the transducer using imaging techniques such as fluoroscopy. Additionally, or alternatively to fluoroscopy, proper positioning of the transducer, e.g., aiming the transducer at a target site, is verified by sensing electrical activity by the electrodes on the catheter carrying the transducer. Comparing similar electrical signals (e.g., electrical signals indicative of a source of cardiac arrhythmias) that are detected by both element 720 and the electrodes on the catheter carrying the transducer, are used to verify proper locating of the transducer.

For some applications, a test signal is applied by the electrode located on the catheter carrying the transducer inside the heart. The test signal passes through cardiac tissue and is received by electrodes on element 720 located in the pericardium. The test signal that is received by element 720 can typically provide information regarding the cardiac tissue. For example, sensing changes in the test signal can indicate the presence of electrical interference inside the tissue of the heart. The test signal that is applied by the electrode inside the heart may be applied at a single frequency (e.g., as a sinusoid) or as a combination of frequencies or signals. In the latter case, a control unit (e.g., a computer processor) may compare the different frequency components of the received test signal, and identify electrical interference due to the comparison.

For some applications, the elements shown in FIG. 21C define, or are components of, a mapping tool that may be used to map tissue as described hereinabove, mutatis mutandis, independently of ablation techniques.

For some applications, element 720 (e.g., electrodes 724 thereof) may be used to facilitate defibrillation of the heart of the subject, e.g., as described with respect to FIGS. 21A-B, mutatis mutandis.

Reference is made to FIGS. 22A-B, 23A-B, and 24A-B, which are schematic illustrations of systems and techniques for magnetically facilitating delivery of a reflection-facilitation element, and thereby for providing and/or positioning a reflective region, in accordance with some applications of the invention. The systems described with reference to FIGS. 22A-B, 23A-B, and 24A-B each comprise a magnetically-attractable reflection-facilitation element, and a magnetic guiding member, configured to magnetically guide the reflection-facilitation element toward the placement site thereof. Typically, the magnetically-attractable reflection-facilitation element are used to increase the efficacy and/or safety of ultrasound-based ablation, e.g., as described throughout this patent application. Typically, the magnetic guiding member is placed in, and moved through, a body lumen that is anatomically separate from the pericardium (e.g., the body lumen is not in fluid communication with the pericardial cavity, and the magnetic guiding member remains outside of the pericardial cavity). The body lumen may, for example, include a blood vessel or a lumen of the gastrointestinal system of the subject. From within the body lumen, and without directly touching the reflection-facilitation element, the magnetic guiding member facilitates delivery and/or positioning of the reflection-facilitation element within the pericardial cavity, by magnetically moving the reflection-facilitation element. For clarity, the pericardium is not shown in FIGS. 22A-24B.

Figure 22B:
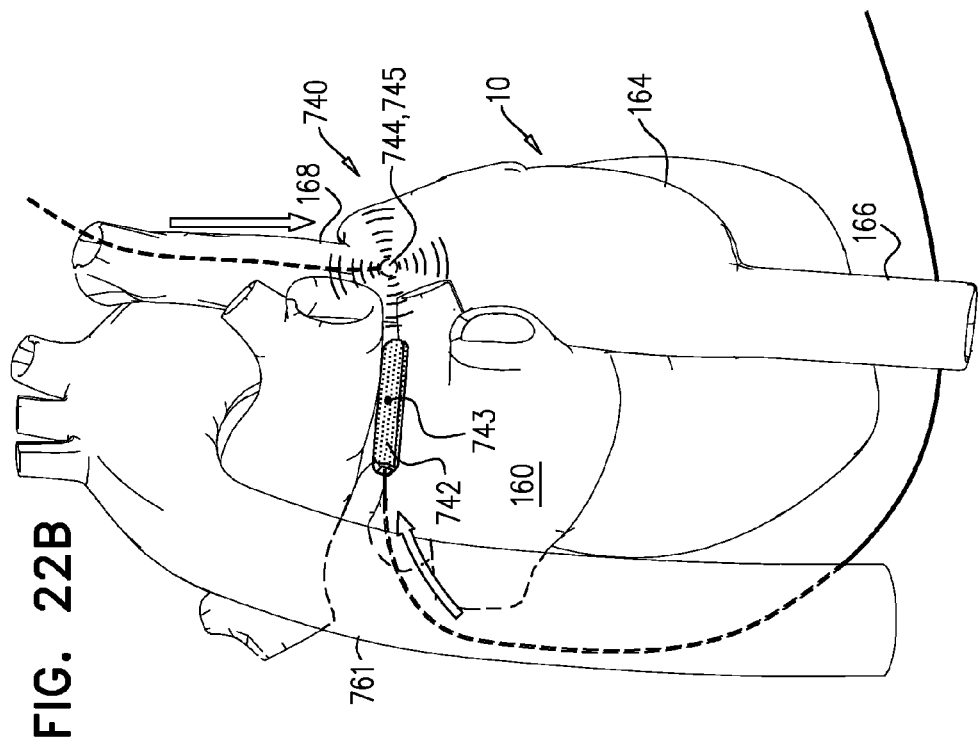
FIGS. 22A-B are schematic illustrations of systems and techniques for magnetically facilitating delivery of a reflection-facilitation element, in accordance with some applications of the invention.
Figure 22A:
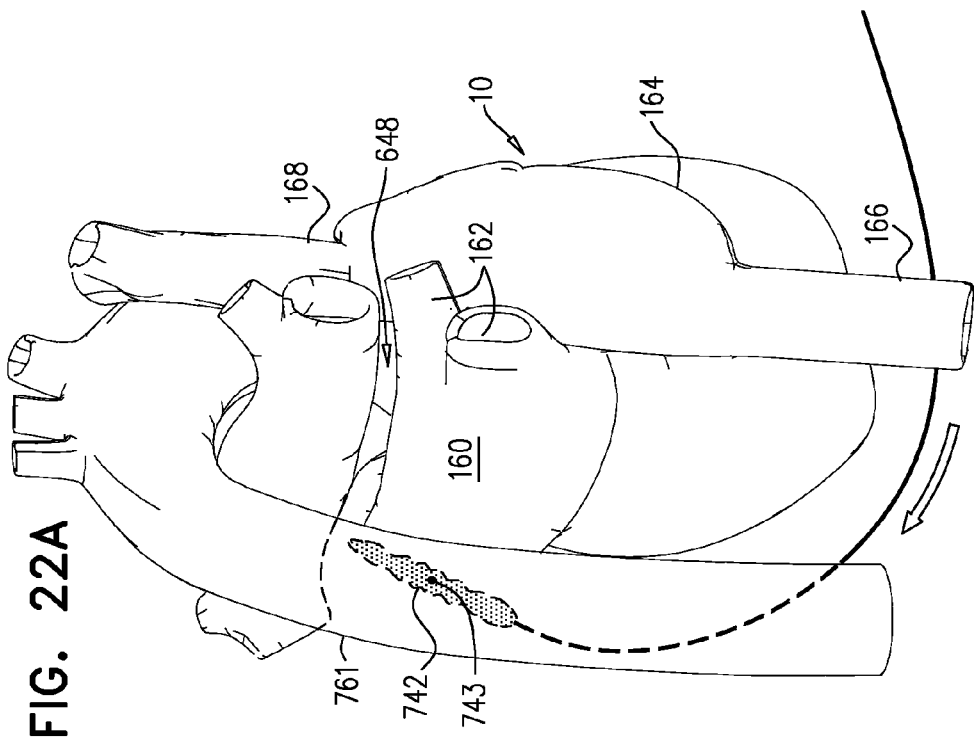

FIGS. 22A-B show a system 740, comprising a magnetically-attractable reflection-facilitation element 742 and a magnetic guiding member 744. Element 742 typically comprises a magnetically-attractable element 743, such as a metallic element. Member 744 typically comprises an electromagnet 745, controllable from outside the body of the subject. Element 742 is delivered to the pericardium of the subject, typically in a deflated state, and typically percutaneously (FIG. 22A). Typically, delivery is achieved via a subxiphoid approach, as is known in the art. For some applications, delivery is achieved via an intercostal approach. Typically, element 742 is delivered to a superior portion of the pericardium, such as to the vicinity of transverse sinus 648.

Magnetic guiding member 744 is percutaneously (e.g., transluminally) delivered to SVC 168, and electromagnet 745 is energized, thereby magnetically coupling member 744 to element 742. The magnetic field of electromagnet 745 draws element 742 into (e.g., deeper into) the transverse sinus (FIG. 22B). Element 742 is typically inflated subsequent to delivery thereof to the transverse sinus.

FIGS. 23A-B show a system 760, comprising a magnetically-attractable reflection-facilitation element 762 and a magnetic guiding member 764. Element 762 typically comprises a magnetically-attractable element 763, such as a metallic element. Member 764 typically comprises an electromagnet 765, controllable from outside the body of the subject. Element 762 is delivered to the pericardium of the subject, typically in a deflated state (FIG. 23A). Typically, delivery is achieved via a subxiphoid approach, as is known in the art. For some applications, delivery is achieved via an intercostal approach. Typically, element 762 is delivered to a superior portion of the pericardium.

Magnetic guiding member 764 is percutaneously (e.g., transluminally, such as transfemorally) delivered to a portion of aorta 761 of the subject that is in the vicinity of element 762. Electromagnet 765 is energized, thereby magnetically coupling member 764 to element 762. Member 764 is subsequently moved upstream through aorta 761. The magnetic field of electromagnet 765 draws element 762 along with member 764 (but in the pericardium; outside of the aorta), and into transverse sinus 648 (FIG. 23B). Element 762 is typically inflated (not shown) subsequent to delivery thereof to the transverse sinus.

Figure 24A:
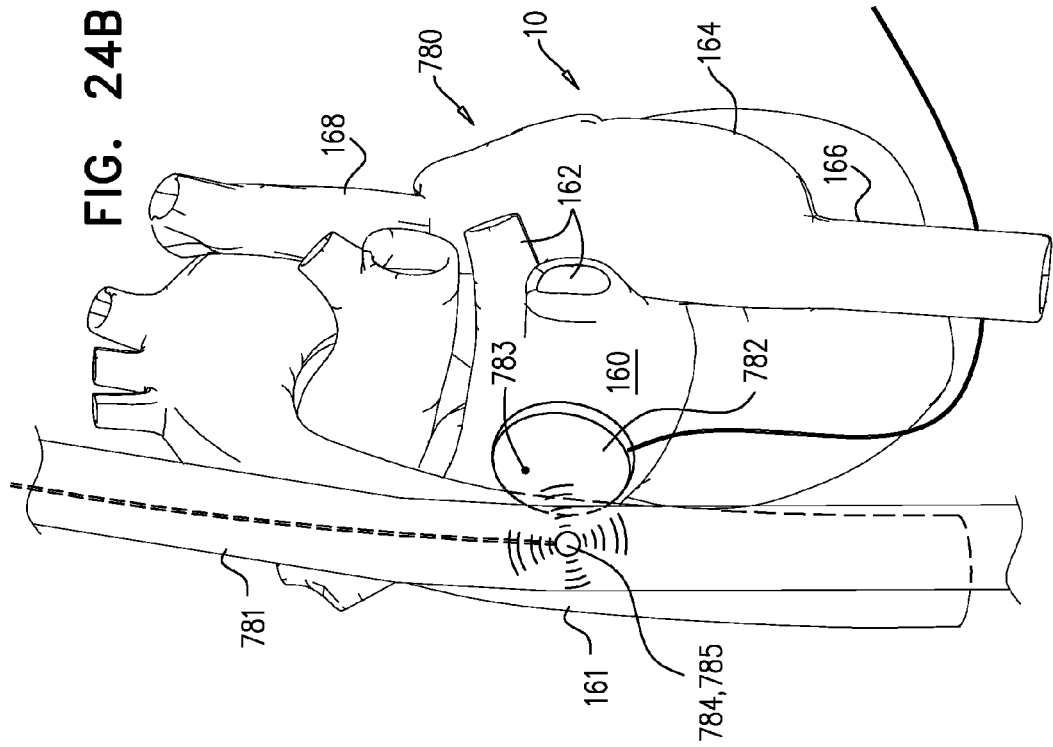
FIGS. 24A-B are schematic illustrations of systems and techniques for magnetically facilitating delivery of a reflection-facilitation element, in accordance with some applications of the invention.
Figure 24B:
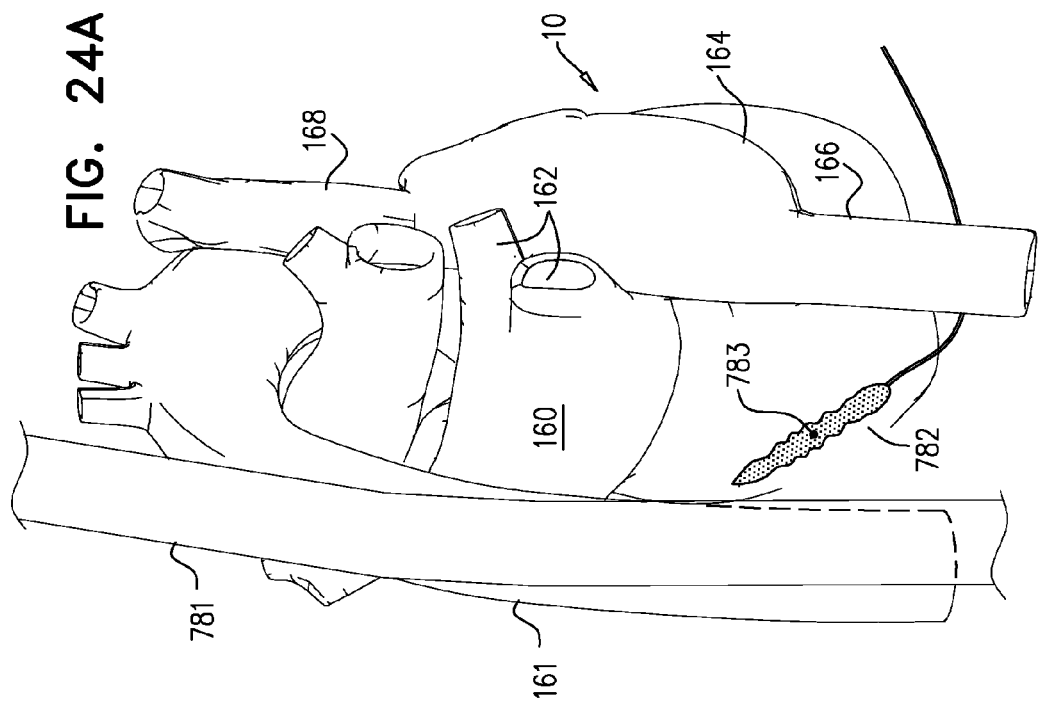

FIGS. 24A-B show a system 780, comprising a magnetically-attractable reflection-facilitation element 782 and a magnetic guiding member 784. Element 782 typically comprises a magnetically-attractable element 783, such as a metallic element. Member 784 typically comprises an electromagnet 785, controllable from outside the body of the subject. Element 782 is delivered to the pericardium of the subject, typically in a deflated state (FIG. 23A). Typically, delivery is achieved via a subxiphoid approach, as is known in the art. For some applications, delivery is achieved via an intercostal approach.

Magnetic guiding member 784 is delivered to a portion of esophagus 781 of the subject that is in the vicinity of element 782. (For clarity, esophagus 781 is not shown in FIGS. 22A-22B.) Electromagnet 785 is energized, thereby magnetically coupling member 784 to element 782. Member 784 is subsequently moved (e.g., superiorly) within esophagus 781, so as to draw element 782 along with member 784 (but outside of the esophagus), and into oblique sinus 646 (FIG. 24B). Element 782 is typically inflated (not shown) subsequent to delivery thereof to the transverse sinus.

FIGS. 22A-B, 23A-B, and 24A-B show each magnetically-attractable reflection-facilitation element as an inflatable reflection-facilitation element. It is to be noted, however, that other reflection-facilitation elements, and indeed other medical devices entirely, may be magnetically guided using the techniques described with reference to FIGS. 22A-B, 23A-B, and/or 24A-B, mutatis mutandis.

Figure 25:
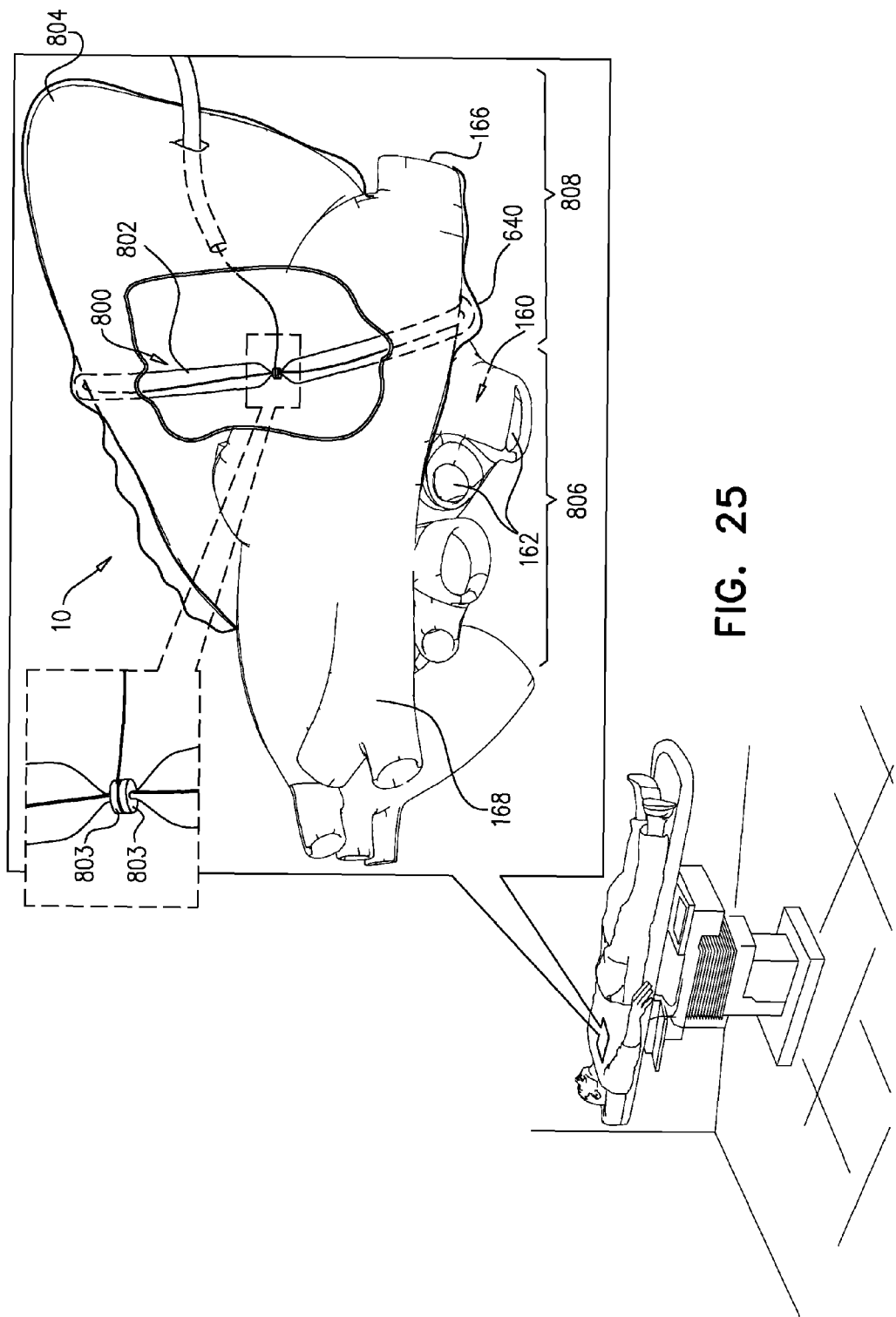
FIG. 25 is a schematic illustration of a reflection-facilitation element for facilitating delivery of a gas to the pericardium of the subject, in accordance with some applications of the invention.

Reference is made to FIG. 25, which is a schematic illustration of a reflection-facilitation element 800, for facilitating delivery of a gas to pericardium 640 of the subject, in accordance with some applications of the invention. As described hereinabove, during a typical cardiac tissue ablation procedure, the subject is in a supine position, and the weight of heart 10 rests on the posterior portion of the pericardium. For some applications, it is desirable to introduce free gas (e.g., gas that is not within an inflatable element) into the pericardium (e.g., instead of, or in addition to, an inflatable reflection-facilitation element), e.g., as described with reference to FIGS. 1A-6. For example, the free gas may provide a reflective region that increases efficacy and/or safety of the ultrasound-based ablation, as described hereinabove. In the supine position, the superior portion of the heart (including the left atrium and pulmonary vein ostia) are disposed below the inferior portion of the heart (including apex 804). Free gas introduced into superior portion 806 of the pericardial cavity (e.g., so as to facilitate ablation of tissue of the atrial wall), is thereby typically displaced by the weight of the heart, into inferior portion 808 of the pericardial cavity (e.g., toward apex 804), and thereby does not facilitate ablation of atrial wall tissue.

Reflection-facilitation element 800 comprises a longitudinal inflatable member 802, which is introduced to the pericardium and is positioned so as to circumscribe heart 10, generally around a superior-inferior axis of the heart. For some applications, and as shown in FIG. 25, portions (e.g., ends) of member 802 are reversibly coupled electromagnetically. For example, one or both ends of member 802 may be coupled to an electromagnet 803. Member 802 is subsequently inflated and thereby becomes wider, thereby reducing (e.g., eliminating) fluid communication between superior portion 806 and inferior portion 808 of the pericardium. That is, member 802, when inflated, divides the pericardial cavity into two portions (e.g., defines portions 806 and 808). Free gas is subsequently delivered to superior portion 806 of the pericardium (e.g., using an introducer), and is inhibited from moving toward inferior portion 808 by element 800 (e.g., by member 802 thereof). The gas thereby provides a reflective region in superior portion 806 of the pericardium, and thereby typically increases efficacy and/or safety of ultrasound-based ablation of adjacent tissue, as described hereinabove.

Reference is made to FIGS. 26A-D, which are schematic illustrations of an inflatable, tissue-separating reflection-facilitation element 820, and use thereof, in accordance with some applications of the invention. For some applications (e.g., in some subjects and/or in some anatomical locations) it is difficult to advance a reflection-facilitation element (e.g., an inflatable reflection-facilitation element) within the pericardium. For example, some portions of the pericardium are narrow and/or closed by a reflection (e.g., a sinus reflection 170; FIG. 18). Reflection-facilitation element 820 is configured to be used in some such applications.

Element 820 has an outer surface that is configured to grip and/or adhere to tissues. For example, the outer surface may comprise a hydrophobic material, such as polycaprolactone (PCL), polyethylene oxide (PEO), and/or TPRE. Element 820 has a deflated state in which the element is generally concave, such that a distal end 821 of element 820 is disposed within the concavity (FIG. 26A).

Figure 26A:
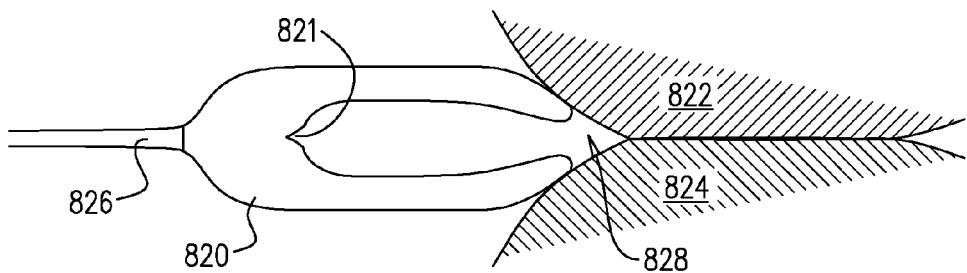
FIGS. 26A-D are schematic illustrations of an inflatable, tissue-separating reflection-facilitation element, and use thereof, in accordance with some applications of the invention.
Figure 26B:
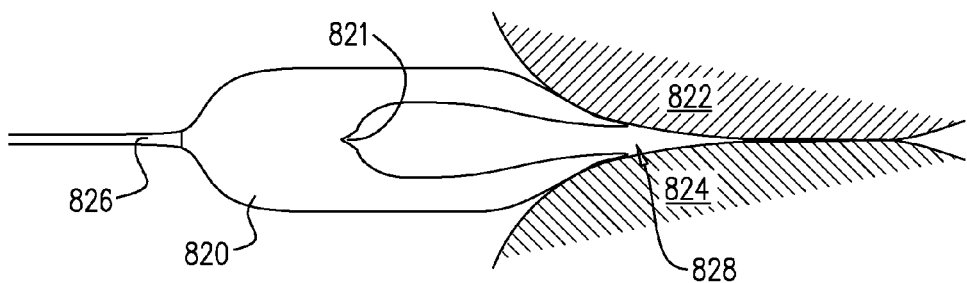
Figure 26C:
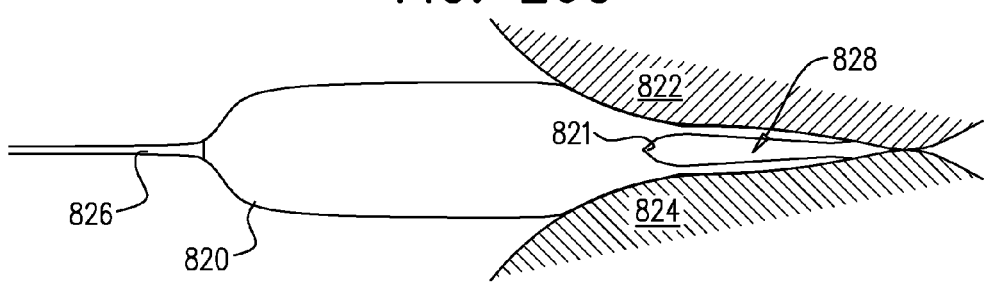
Figure 26D:
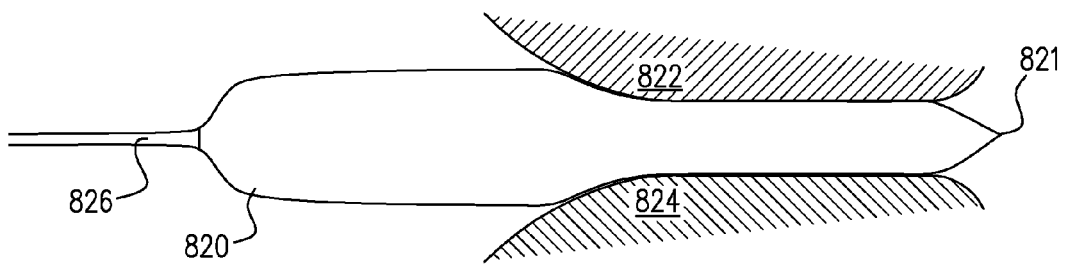

FIGS. 26A-D show a first tissue 822 and a second tissue 824, which are generally in close contact and/or are loosely connected with each other. For example, tissue 822 may comprise the parietal pericardium and tissue 824 may comprise the visceral pericardium. Element 820 is placed, in the deflated state thereof, at a site 828 at which the interface between tissues 822 and 824 is accessible, and is placed in contact with the interface such that (1) a portion (e.g., a first portion) of element 820 that is outside the concavity on one side of the concavity is in contact with tissue 822, and (2) a portion (e.g., a second portion) of the inflatable member that is outside the concavity on the other side of the concavity is in contact with tissue 824 (FIG. 26A). Element 820 is subsequently inflated (e.g., using a control tube 826), typically while at least gently pressing element 820 against the tissues, so as to maintain contact (FIGS. 26B-C) As element 820 is progressively inflated, element 820 inverts by progressive portions of element 820 emerging from the concavity. The progressive portions of element 820 grip and/or adhere to respective progressive portions of the tissues, until distal end 821 becomes the distal-most portion of element 820 (FIG. 26D). Inflation of element 820 thereby moves distally between tissues 822 and 824. Furthermore, element 820 typically separates tissues 822 and 824 by pulling the tissues apart.

For some medical procedures, separation of adjacent tissues without cutting (known as "blunt dissection") is a useful technique for gaining access to the target site. For some applications, element 820 may be used as a blunt dissection tool, mutatis mutandis, in addition to, or instead of, as a reflection-facilitation element.

Reference is made to FIGS. 27A-B, which are schematic illustrations of a system 840 for facilitating ablation of heart tissue, in accordance with some applications of the invention. System 840 comprises a transducer unit 842, comprising a plurality of ultrasound transducers 844, arranged in a three-dimensional array. For example, and as shown in FIGS. 27A-B, transducer unit 842 may be generally cylindrical, with transducers 844 disposed (e.g., circumferentially disposed) on the lateral sides of the transducer unit. Alternatively, transducers 844 may be arranged in one or more sheets (e.g., two-dimensional arrays). Typically, transducers 844 comprise CMUTs.

System 840 further comprises a control unit 846, configured to drive the transducers to apply ultrasound. Typically, and as shown in FIGS. 27A-B, control unit 846 is fixedly coupled to transducer unit 842 (e.g., the control unit and transducer unit are integrated). Alternatively, control unit 846 may be separate from the transducer unit. For example, the control unit may be extracorporeal, and wirelessly or wiredly coupled to the transducer unit.

Transducer unit 842 is introduced to the vicinity of the tissue to be ablated. For example, unit 842 may be configured to be placed within a chamber of the heart of the subject, so as to ablate tissue of the wall of the chamber. For example, as shown in FIGS. 27A-B, unit 842 may be configured to be placed within, and ablate tissue of, left atrium 160 of the subject, so as to treat atrial fibrillation.

Control unit 846 drives transducer unit 842 (e.g., transducers 844 thereof) to apply a first application 850 of ultrasound energy to the tissue (FIG. 27A; represented by concentric rings). Typically, first application 850 is configured to be non-ablating. At least part of the ultrasound energy of application 850 is reflected by the tissue as one or more echoes 852 (e.g., echoes 852a, 852b, and 852c); features of the echoes being dependent on features (e.g., anatomy and/or composition) of the tissue. For example, echo 852a is characteristic and/or indicative of atrial wall 161, and echo 852b is characteristic and/or indicative of an ostium 843. Transducer unit 842 detects echoes 852, and responsively generates a signal. Typically, each transducer 844 comprises a transceiver. That is, each transducer is configured to detect, as well as to apply, ultrasound energy. Alternatively, transducer unit 842 may comprise a plurality of dedicated ultrasound receivers.

Control unit 846 receives the signal generated by unit 842. Typically, control unit 846 determines the location of anatomical features (e.g., atrial wall 161 and pulmonary vein ostia 843) in response to receiving the signal. For example, control unit 846 may comprise a mapping unit 848, which generates a map of the anatomy. For some applications, the map is entirely internal and is used solely by system 840. For some applications, the map is displayed on an extracorporeal display 860, e.g., such that a physician may view the map during and/or after the procedure.

In response to the signal, control unit 846 drives transducer unit 842 (e.g., transducers 844 thereof) to apply a second application 854 (e.g., portions 854a and 854b thereof) of ultrasound energy, configured to ablate the tissue (FIG. 27B). For example, control unit 846 may configure the transducers to direct, focus, and/or otherwise configure second application 854 of ultrasound energy (e.g., at least portion 854a thereof) to ablate the tissue as desired. In the example shown in FIG. 27B, system 840 is shown ablating tissue that circumscribes ostia 843 of two pulmonary veins 162 (e.g., in a manner similar to that described with reference to FIG. 7, mutatis mutandis) in response to receiving echoes 852. Similarly, system 840 may be used to perform other ablations of tissue of atrium 160, e.g., ablation of a Cox maze.

Thereby, system 840 is configured to perform acoustic location (e.g., mapping) of anatomical features relative to transducer unit 842, and to subsequently direct and/or configure ultrasound to ablate tissue in the desired location and/or manner.

As described hereinabove, a reflective region may be provided by providing a reflection-facilitation element on the other side of the target tissue to an ultrasound transducer, thereby typically increasing efficacy and/or safety of ultrasound-based ablation. FIGS. 27A-B show a reflection-facilitation element 856 having been placed pericardially around a portion of left atrium 160. First application 850 of ultrasound energy is reflected by element 856 as echo 852c (FIG. 27A), which is characteristic and/or indicative of element 856. Echo 852c is received by transducer unit 842, and is distinguishable by control unit 846 from other echoes 852 (e.g., echo 852a and/or echo 852b). Thereby, for some applications, in addition to acoustically locating (e.g., mapping) anatomical features, system 840 (e.g., control unit 846 and/or mapping unit 848) acoustically locates (e.g., maps) reflection-facilitation elements.

For applications in which a reflection-facilitation element is used, control unit 846 typically configures the second application of ultrasound energy in response to locating element 856. At portions of the target site that are determined to be backed by a reflective region (e.g., a reflection-facilitation element), the second application of ultrasound energy (e.g., at least a portion 854b thereof) is configured to utilize the reflective region, e.g., so as to increase safety and/or efficiency of the ultrasound-based ablation.

Reference is made to FIG. 28, which is a schematic illustration of a pericardial access tool 880, comprising a helical needle 882 and a sensor 884, in accordance with some applications of the invention. The needle 882 is shaped to define a space along the longitudinal axis thereof (e.g., of the helix), and sensor 884 is disposed in that space. Typically, a distal end 886 (e.g., a tip) of needle 882 is disposed slightly distal to a distal end 888 (e.g., a tip) of sensor 884. Tool 880 is configured to facilitate access to the pericardial cavity by facilitating penetration of the fibrous pericardium and parietal pericardium, and reducing a likelihood of penetrating the visceral pericardium.

Sensor 884 may comprise an electrical sensor, an ultrasound sensor, and/or an imaging device, and is configured to sense the location of at least the sensor (e.g., a location of tool 880) with respect to the tissue being penetrated. For example, sensor 884 may be configured to sense a distance to and/or a depth within a tissue (e.g., the fibrous pericardium), by detecting changes in color and/or brightness of light, electrical impedance, and/or reflection of ultrasound energy. For some applications, sensor 884 comprises an ultrasound transducer, configured to apply the ultrasound energy that is detected (i.e., sensor 884 is an ultrasound transceiver).

Tool 880 is advanced to the pericardium of the subject, and at least needle 882 is rotated, such that the needle penetrates the fibrous pericardium, in a manner similar to that of a corkscrew. When sensor 884 determines that a desired depth of penetration has been achieved, the rotation is stopped. For example, a control unit 890 may receive, from sensor 884, a signal indicative of the depth of penetration, and display information indicative of the depth of penetration (e.g., indicative of penetration of the parietal pericardium), such that a physician may control rotation and/or advancement of needle 882. For some applications, the control unit controls rotation and/or advancement of needle 882, and automatically stops the rotation when the desired depth of penetration has been achieved.

For some applications, needle 882 is shaped to define a lumen therethrough. A guidewire 892 is disposed within, and/or is slidable through, the lumen. While distal end 886 of the needle is disposed within the pericardial cavity, the guidewire is advanced distally from the distal end of the needle, and into the pericardial cavity. Needle 882 is subsequently removed from the pericardium, leaving behind guidewire 892, to be used for facilitating further pericardial access.

It is to be noted that tool 880 may be used to facilitate access other cavities of the body of the subject, other than the pericardial cavity.

Reference is made to FIGS. 29A-B, which are schematic illustrations of an inflatable reflection-facilitation element 910, in accordance with some applications of the invention. Element 910 comprises an inflatable portion 912, and an inflation tube 914, in fluid communication with the inflatable portion, and typically disposed within and/or integral with a steerable catheter 916. Typically, and as shown in FIGS. 29A-B, portion 912 has a generally round (e.g., circular or oval) shape. Alternatively, portion 912 may have another shape (e.g., a shape described with reference to FIGS. 5A-I, mutatis mutandis).

Element 910 further comprises one or more adjustable restricting elements 918, configured to limit expansion of portion 912 in a given dimension when inflated, such that the expansion in the given dimension is controllable from outside the body of the subject. FIG. 29A shows portion 912 having been inflated to have a first length in a given dimension. Restricting element 918 comprises a longitudinal member 920 (e.g., a wire or thread) that is coupled to an inner surface of inflatable portion 912, and extends to outside of the inflatable portion (e.g., to outside the body of the subject). A maximum length of inflatable portion 912 in the given dimension is controllable by adjusting tension on member 920. For example, and as shown in FIGS. 29A-B, inflatable portion 912 may define two or more coupling sites 922 on the inner surface of portion 912, and member 920 is slidably coupled to at least one (e.g., both) of the coupling sites. At least one end of member 920 extends through catheter 916, such that increasing tension (e.g., pulling) on member 920 reduces a maximum distance between the coupling sites, and thereby reduces the maximum length of the inflatable member in the dimension between the coupling sites (FIG. 29B).

For some applications, element 910 comprises a plurality of adjustable restricting elements 918, each element 918 being configured to control a maximum length of the inflatable portion in a respective dimension. Thereby, the shape of inflatable portion 912 is adjustable in more than one dimension. For example, a maximum length in one dimension may be reduced, and a maximum length in another dimension may be increased. Thereby, for some such applications, inflatable portion 912 is configured such that the shape thereof is controllable while the inflatable portion is disposed within the body of the subject.

Typically, inflatable reflection-facilitation element 910 (e.g., inflatable portion 912 thereof) is configured to be disposed at placement site 642 within the pericardial cavity (FIG. 18), and to provide a reflective region at the oblique sinus and/or increase the distance between the left atrium and tissues posterior thereto. For some applications, element 910 comprises an ablation element (e.g., an ultrasound, RF or cryogenic element; not shown), disposed on one side of inflatable portion 912. For such applications, the reflection-facilitation element is configured to be used as an integrally-insulated ablation tool in which the gas used to inflate the inflatable portion 912 insulates and/or distances tissues on one side of the inflatable portion from the ablation element on the other side of the inflatable portion.

Figure 30:
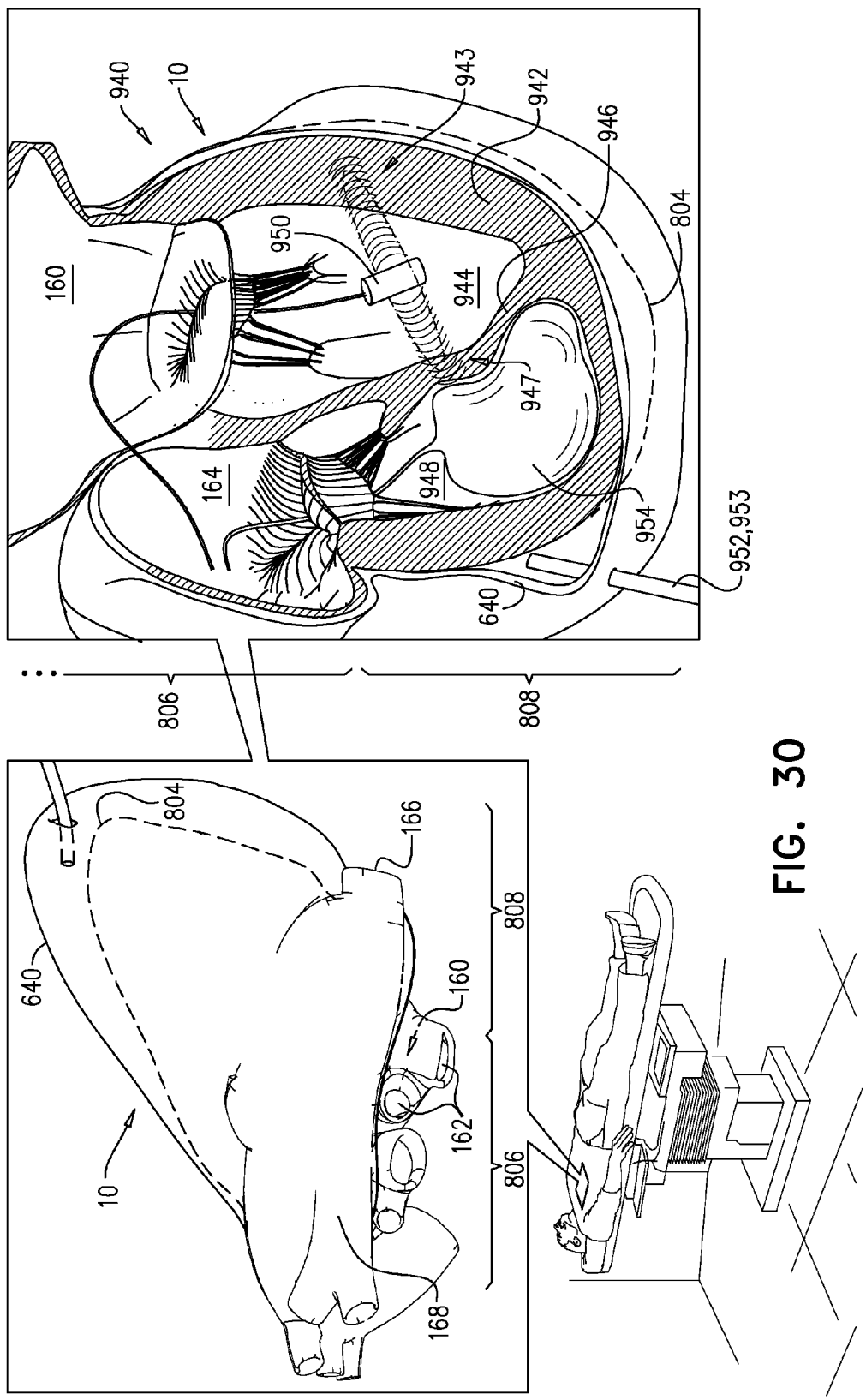
FIG. 30 is a schematic illustration of a system for ablating tissue of heart of a subject, in accordance with some applications of the invention.

Reference is made to FIG. 30, which is a schematic illustration of a system 940 for ablating tissue of heart 10 of a subject, in accordance with some applications of the invention. System 940 is typically used to ablate tissue of a ventricle (i.e., tissue defining the ventricle) of a subject, e.g., to treat ventricular tachycardia. For example, system 940 may be used to ablate tissue of wall 942 of left ventricle 944 and/or of interventricular septum 946 of the subject. System 940 comprises an ultrasound transducer unit 950, comprising at least one ultrasound transducer, and at least one (e.g., a first) reflection-facilitation element 952, configured to provide a reflective region within pericardium 640 that surrounds the heart.

As described hereinabove, during a typical cardiac tissue ablation procedure, the subject is in a supine position, and the weight of heart 10 rests on the posterior portion of the pericardium. For some applications, it is desirable to introduce free gas (e.g., gas that is not within an inflatable element) into the pericardium (e.g., instead of, or in addition to, an inflatable reflection-facilitation element), such as described with reference to FIGS. 1A-6, mutatis mutandis. In the supine position, superior portion 806 of the heart (including the left atrium and pulmonary vein ostia) are disposed below inferior portion 808 of the heart (including apex 804). Free gas introduced into the pericardial cavity (e.g., so as to facilitate ablation of tissue of the atrial wall), would thereby typically move to and/or remain in inferior portion 808 of the pericardial cavity, due to displacement by the weight of the heart. For some applications in which ventricular tissue is to be ablated, this displacement is advantageous, because a reflective region is thereby provided in the vicinity of (e.g., around) the ventricle(s).

Reflection-facilitation element 952 thereby typically comprises an introducer 953 (e.g., a needle or a tube), and provides a reflective region by facilitating delivery of free gas into the pericardial cavity. Transducer unit 950 is delivered (e.g., transluminally) to the ventricle (e.g., left ventricle 944), and reflection-facilitated ultrasound ablation is performed on ventricular wall 942, e.g., at an ablation site 943. Alternatively, reflection-facilitation element 952 may comprise an inflatable reflection-facilitation element, such as those described herein.

Typically, system 940 further comprises a second reflection-facilitation element 954, configured to be provide a reflective region in a second ventricle of the heart. For example, and as shown in FIG. 30, second reflection-facilitation element 954 comprises an inflatable reflection-facilitation element, and is configured to be placed in right ventricle 948, i.e., on the other side of septum 946. Reflection-facilitated ultrasound ablation is performed on septum 946, e.g., at an ablation site 947, by applying ultrasound energy using transducer unit 950 and reflecting the ultrasound energy using element 954. The reflective regions provided by reflection-facilitation elements 952 and 954 typically increase efficacy and/or safety of the ultrasound-based ablation, as described hereinabove.

For some applications, reflection-facilitation element 954 is used without providing a reflective region in the pericardial cavity (e.g., without using reflection-facilitation element 952). For example, for applications in which it is desirable to ablate tissue only at ablation site 947 in interventricular septum 946, element 954 is placed in right ventricle 948 and a transducer unit (e.g., unit 950) is placed in left ventricle 944, but gas is not delivered to the pericardial cavity.

For some applications of the invention, the gas used to provide the reflective regions (e.g., the gas delivered to the pericardium and/or the gas used to inflate the inflatable reflection-facilitation elements) is cooled at the start of the procedure and/or throughout the procedure, so as to reduce heating of heart tissue. For example, the free gas delivered to the pericardium may be cooled, so as to cool the coronary arteries during ablation of nearby (e.g., underlying) tissue. Similarly, cooling of inflation fluid (e.g., gas and/or liquid) may be combined with other techniques described herein. For some applications, the cooling is provided by providing the gas to the balloon under high pressure, and inflating the balloon by expanding the gas; the expansion automatically cooling the gas. For some applications, the cooling is provided by thermoelectric cooling, e.g., using a Peltier cooler, which may be provided coupled to, or as a component of, the inflatable reflection-facilitation element. For some applications, the cooling is provided by cooling the inflation fluid extracorporeally. For some applications, the inflation fluid is cooled to less than 20 degrees C. and/or more than 5 degrees C., such as 5-20 C, e.g., 5-15 degrees C., such as 5-10 degrees C. or 10-15 degrees C. The cooling typically does not damage tissue that is in contact with the inflation fluid or the inflatable element in which the fluid is disposed.

Reference is again made to FIGS. 1A-30. For some applications, the inflatable reflection-facilitation elements described hereinabove comprise an inelastic material. For example, the reflection-facilitation elements may generally have the same outer surface area when inflated as when deflated, and inflation increases the convexity of the reflection-facilitation element without the reflection-facilitation element expanding and/or stretching. For some such applications, the reflection-facilitation elements are delivered (e.g., percutaneously delivered) in a folded and/or rolled state, and unfold and/or unroll when inflated.

For some applications of the invention, the temperature of the fluid (e.g., gas) used to inflate one or more reflection-facilitation elements and/or the pericardial cavity (e.g., so as to provide a reflective region) is regulated (e.g., adjusted and/or maintained). For example, the temperature may be adjusted prior to inflation, and/or may be maintained after inflation (e.g., by circulating the intracorporeal portion of the fluid with an external supply). For some such applications, the fluid is cooled, so as to reduce undesirable heating of tissues (e.g., those outside of the target ablation site). For some such applications, the fluid is heated, so as to increase ablation at the target ablation site (e.g., by a thermal effect).

For some applications of the invention, the reflection-facilitation element comprises a temperature sensor, and is configured to sense the temperature of the tissue of the subject, such as the target tissue being treated. Typically, such temperature sensing facilitates ablation by ensuring sufficient heating and/or preventing overheating of the target tissue. For some applications of the invention, the reflection-facilitation element comprises, or is in fluid communication with, a pressure sensor, configured to prevent over-inflation of the reflection-facilitation element.

Reference is again made to FIGS. 1A-30. For some applications of the invention, the techniques described herein may be used in combination with other ablation techniques, such as cryoablation and radio frequency (RF) ablation. Typically, the inflation fluid (e.g., gas) improves efficacy of the other ablation treatment, as well as enhancing safety. For example, the inflation fluid typically isolates (e.g., insulates) the treated area such that the effects of cryoablation and/or RF ablation treatment are improved.

For some applications, apparatus described hereinabove comprise temperature-resistant materials, according to ablation techniques used. For example, reflection-facilitation elements (e.g., inflatable portions thereof) that are used to facilitate RF and/or ultrasound ablation may comprise thermoplastic polyurethane (TPU) and/or nylon 12, which are relatively heat-resistant. Conversely, reflection-facilitation elements (e.g., inflatable portions thereof) that are used to facilitate cryogenic ablation may comprise low density polyethylene (LDPE), which is relatively cold-resistant.

Reference is again made to FIGS. 1A-30. For some applications of the invention, the techniques described herein are facilitated by x-ray imaging techniques, such as fluoroscopy. For some such applications, the inflation fluid (e.g., gas), which is typically less dense than surrounding tissues, facilitates such x-ray imaging, by increasing a contrast and/or a distance between tissues.

For some applications, the techniques described herein are facilitated by a three-dimensional electromagnetic tracking system, such as the Aurora EM Tracking System provided by Northern Digital Inc. For example, a three-dimensional electromagnetic sensor may be coupled to a reflection-facilitation element and/or a transducer, the sensor providing location and/or orientation information based on detecting an electromagnetic field provided by an extracorporeal field generator.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use in a pericardial cavity proximate to a heart of a subject, the apparatus comprising:
 a reflection-facilitation element, configured to be disposed in the pericardial cavity and on a first side of a tissue of the subject, and comprising:
  an inflatable member, having a first side and a second side, and configured to be inflated while disposed in the pericardial cavity; and
  a plurality of electrodes, comprising at least a first electrode and a second electrode, the first electrode being disposed on the first side of the inflatable member; and
 an ultrasound transducer, configured to be placed on a second side of the tissue of the subject, and to apply ultrasound energy to the tissue of the subject such that at least a portion of the energy reaches the inflatable member, the inflatable member being configured to reflect at least a portion of the ultrasound energy that reaches the inflatable member,
 wherein the second electrode is disposed on the second side of the inflatable member, and is electrically coupled to the first electrode via a wire configured to conduct electricity from the first side to the second side of the inflatable member.

2. The apparatus according to claim 1, wherein the plurality of electrodes are configured to facilitate navigation of the inflatable member towards the heart of the subject.

3. The apparatus according to claim 1, further comprising a control unit, electrically coupled to the plurality of electrodes.

4. The apparatus according to claim 3, wherein each one of the plurality of electrodes is independently electrically coupled to the control unit.

5. The apparatus according to claim 3, wherein the control unit is configured to drive the plurality of electrodes to apply a defibrillating current to the heart of the subject.

6. The apparatus according to claim 3, wherein the plurality of electrodes comprises at least 16 electrodes.

7. The apparatus according to claim 3, wherein the control unit comprises a monitor, configured to detect, via the electrodes, an electrical signal of the heart of the subject.

8. The apparatus according to claim 7, wherein the control unit comprises an extracorporeal display, configured to provide information relating to a position of the inflatable member with respect to anatomy of the subject, based on the detected electrical signal of the heart.

9. The apparatus according to claim 8, wherein the display is configured to display a graphical representation of the position of the inflatable member with respect to anatomy of the subject.

10. The apparatus according to claim 8, wherein the display is configured to display a graphical representation of anatomy of the subject.

11. The apparatus according to claim 7, wherein the control unit is configured to identify a target for ablation in the tissue of the subject, by detecting an electrical abnormality in the electrical signal of the heart of the subject.

12. A method for use with a subject, the method comprising:
- delivering a reflection-facilitation element to a pericardial cavity of the subject, the reflection-facilitation element having (a) an inflatable member, having a first side and a second side, and (b) a plurality of electrodes, having at least a first electrode and a second electrode, the first electrode being disposed on the first side of the inflatable member;
- while the inflatable member is disposed in the pericardial cavity of the subject, inflating the inflatable member by delivering a fluid to the inflatable member;
- placing an ultrasound transducer in a chamber of a heart of the subject;
- ablating cardiac tissue by activating the ultrasound transducer to apply ultrasound energy, such that at least part of the ultrasound energy is reflected by the inflatable member;
- providing an extracorporeal monitor electrically coupled to the plurality of electrodes, and facilitating detecting, via the electrodes, of an electrical signal of the heart of the subject; and
- monitoring progression of the ablation of the cardiac tissue by the detecting of the electrical signal of the heart of the subject.

13. The method according to claim 12, wherein detecting comprises detecting timing of the electrical signal.

14. The method according to claim 12, wherein detecting comprises detecting a magnitude of the electrical signal.

15. The method according to claim 12, wherein monitoring the progression of the ablation of the cardiac tissue comprises monitoring the progression of the ablation of the cardiac tissue by detecting a reduction of an electrical abnormality in the electrical signal.

16. The method according to claim 12, wherein the extracorporeal monitor includes an extracorporeal display, and the method further comprises displaying on the extracorporeal display a graphical representation of a position of the inflatable member with respect to anatomy of the subject, based on detecting the electrical signal of the heart.

17. The method according to claim 12, wherein the extracorporeal monitor includes an extracorporeal display, and the method further comprises displaying on the extracorporeal display a graphical representation of an anatomy of the subject, based on detecting the electrical signal of the heart.

18. A method for use with a subject, the method comprising:
- delivering a reflection-facilitation element to a pericardial cavity of the subject, the reflection-facilitation element having (a) an inflatable member, having a first side and a second side, and (b) a plurality of electrodes, having at least a first electrode and a second electrode, the first electrode being disposed on the first side of the inflatable member;
- while the inflatable member is disposed in the pericardial cavity of the subject, inflating the inflatable member by delivering a fluid to the inflatable member;
- placing an ultrasound transducer in a chamber of a heart of the subject;
- ablating cardiac tissue by activating the ultrasound transducer to apply ultrasound energy, such that at least part of the ultrasound energy is reflected by the inflatable member;
- providing an extracorporeal monitor electrically coupled to the plurality of electrodes, and facilitating detecting, via the electrodes, of an electrical signal of the heart of the subject; and
- identifying the cardiac tissue for ablation by the detecting of an electrical abnormality in the electrical signal of the heart of the subject.

* * * * *